(12) United States Patent
Havenga et al.

(10) Patent No.: US 7,968,286 B2
(45) Date of Patent: Jun. 28, 2011

(54) SETTINGS FOR RECOMBINANT ADENOVIRAL-BASED VACCINES

(75) Inventors: Menzo J. E. Havenga, Alphen a/d Rijn (NL); Stefan Kostense, Den Haag (NL)

(73) Assignee: Crucell Holland B.V., Leiden (NL)

(*) Notice: Subject to any disclaimer, the term of this patent is extended or adjusted under 35 U.S.C. 154(b) by 0 days.

(21) Appl. No.: 12/930,661

(22) Filed: Jan. 12, 2011

(65) Prior Publication Data

US 2011/0130301 A1 Jun. 2, 2011

Related U.S. Application Data

(60) Continuation of application No. 11/978,043, filed on Oct. 25, 2007, now abandoned, which is a division of application No. 11/105,725, filed on Apr. 14, 2005, now Pat. No. 7,598,078, which is a continuation of application No. PCT/EP03/50748, filed on Oct. 23, 2003.

(30) Foreign Application Priority Data

Oct. 23, 2002 (NL) .................. PCT/NL02/00671

(51) Int. Cl.
*C12Q 1/70* (2006.01)
*C12Q 1/66* (2006.01)
(52) U.S. Cl. ............................................. 435/5; 435/8
(58) Field of Classification Search .................. None
See application file for complete search history.

(56) References Cited

U.S. PATENT DOCUMENTS

| | | | |
|---|---|---|---|
| 5,922,315 A | 7/1999 | Roy |
| 5,994,128 A | 11/1999 | Fallaux et al. |
| 6,492,169 B1 | 12/2002 | Vogels et al. |
| 6,670,188 B1 | 12/2003 | Vogels et al. |
| 6,733,993 B2 | 5/2004 | Emini et al. |
| 6,913,922 B1 | 7/2005 | Bout et al. |
| 2003/0044421 A1 | 3/2003 | Emini et al. |

FOREIGN PATENT DOCUMENTS

| | | |
|---|---|---|
| EP | 99201545.3 | 5/1999 |
| EP | 0 978 566 | 2/2000 |
| WO | WO 96/26281 | 8/1996 |
| WO | WO 98/32842 | 7/1998 |
| WO | WO 98/50053 | 11/1998 |
| WO | WO 99/64582 | 12/1999 |
| WO | WO 00/03029 | 1/2000 |
| WO | WO 00/52186 | 9/2000 |
| WO | WO 00/60106 | 10/2000 |
| WO | WO 00/70071 | 11/2000 |
| WO | WO 01/02607 | 1/2001 |
| WO | WO 01/21201 | 3/2001 |
| WO | WO 02/22080 | 3/2002 |
| WO | WO 02/24730 | 3/2002 |
| WO | WO 02/053759 | 7/2002 |
| WO | WO 2004/028478 | 4/2004 |

OTHER PUBLICATIONS

Anderson, et al.; A simple method for the rapid generation of recombinant adenovirus vectors; Gene Ther., Jun. 8, 2000; 7 (12); pp. 1034-1038.
Basler. et al.; Sequence of the immunoregulatory early region 3 and flanking sequences of adenovirus type 35, Gene, 1996 pp. 249-254, vol. 170.
Bostic. et al., Quantitative Analysis of Neutralizing Immune Response to Human Parvovirus BI9 Using a Novel Reverse Transcriptase-Polymerase Chain Reaction-Based Assay, Journal of Infectious Disease, 1999, pp. 619-626, vol. 179, Chicago, IL, US.
European Search Report, EP 03 780 172, dated Dec. 6, 2007.
Flomenberg, et al.; Sequence and genetic Organization of Adenovirus Type 35 Early Region 3; Journal of Virology. Nov. 1988, pp. 4431-4437, vol. 62, No. 11.
Flomenberg, et al; Molecular Epidemiololgy of Adenovirus Type 35 Infections in Immunocompromised Hosts; The Journal of Infectious Diseases, Jun. 1987, pp. 1127-1134, vol. 155, No. 6.
Gaher Y-Segard, et al.; Immune response to recombinant Capsid Proteins of Adenovirus in Humans: Antifiber and Anti-Penton Base Antibodies Have Synergistic Effect on Neutralizing Activity; Journal of Virology. Mar. 1998, pp. 2388-2397, vol. 72, No. 3.
Hsu, et al., Immunogenicity of Recombinant Adenovirus-Respiratory Syncytial Virus Vaccines with Adenovirus Types 4, 5, and 7 Vectors in Dogs and a chimpanzee; Journal of Infectious Diseases, Oct. 1, 1992, pp. 769-775, vol. 166, No. 4.
Kang, et al.; Molecular Cloning and Physical Mapping of the DNA of Human Adenovirus Type 35, Acta Microbiologica Hungarica 1999, pp. 67-75, vol. 36, No. 1.
Kass-Eisler. et al.: Circumventing the immune response to adenovirus-mediated gene therapy; Gene Therapy, Feb. 1, 1996, pp. 154-162, vol. 2. No. 3.
Klein, et al.; Accurate estimation of transduction efficiency necessitates a multiplex real-time PCT, Gene Therapy, 2000, pp. 458-463, vol. 7.
Krasnykh, et al.; Generation of Recombinant Adenovirus Vectors with modified Fibers for Altering Viral Tropism. Journal of Virology. Oct. 1996. pp. 6839-6846, vol. 70. No. 10.
Liu, et al., Is Green Fluorescent Protein Toxic to the Living Cells? Biochemical and Biophysical Research Communication, 1999. pp. 712-717, vol. 260.
Lubeck, et al., Immunogenicity and efficacy testing in chimpanzees of an oral hepatitis B vaccine based on live recombinant adenovirus, Proc. Natl. Acad. Sci. USA, 1989, pp. 6763-6767, vol. 86, No. 17.
Mack, et al.; Circumvention of Anti-Adenovirus Neutralizing Immunity by Administration of an Adenoviral Vector of an Alternate Serotype; Human Gene Therapy, 1997, pp. 99.109, vol. 8, No. 1.
Mastrangeli, et al., Sero-Switch Adenovirus—Mediated in Vivo Gene Transfer: Circumvention of Anti-Adenovirus Humoral Immune Defenses Against Repeat Adenovirus Vector Administration by Changing the Adenovirus Serotype; Human Gene Therapy, 1996, pp. 79-87, vol. 7, No, 1.
Moffatt, et al.; Circumvention of Vector-Specific Neutralizing Antibody Response by Alternating Use of Human and Non Human Adenoviruses: Implications in Gene Therapy, Virology, Jun. 30, 2000, pp. 159-167, vol. 272, No. 1.
Natuk, et al.; Adenovirus Vectored Vaccines, Developments in Biological Standardization, 1994, pp. 71-77, vol. 82.

(Continued)

*Primary Examiner* — Bo Peng
(74) *Attorney, Agent, or Firm* — TraskBritt

(57) ABSTRACT

Described are of recombinant adenoviral vectors in vaccination regimens, such as prime/boost set-ups and subsequent vaccinations and applications for gene therapy. Moreover, described are assays to determine the best regimen for applying the most suitable recombinant viral vector in a vaccination or gene therapy setting.

8 Claims, 37 Drawing Sheets

OTHER PUBLICATIONS

Natuk, et al.; Adenovirus-human deficiency virus (HIV) envelope recombinant vaccines elicit high-titered HIV-neutralizing antibodies in the dog model, Proc. Natl. Acad. Sci. USA, Aug. 1992, pp. 7777-7781, vol. 89, No. 16.

Natuk, et al.; Immunogenicity of Recombinant Human Adenovirus—Human Immunodeficiency Virus Vaccines in Chimpanzees, AIDS Research and Human Retroviruses, 1993, pp. 395-404, vol. 9, No. 5.

Nishimura, et al., Determination of a Statistically Valid Neutralization Titer in Plasma That Confers Protection against Simian-Human Immunodeficiency Virus Challenge following Passive Transfer of High-Titered Neutralizing Antibodies, Journal of Virology, Mar. 2002, pp. 2123-2130. vol. 76, No. 5.

Notice of Opposition to a European Patent, Patent No. 1054064, by Cell Genesys Inc., dated Jul. 5, 2005.

Parks, et al.; Use of a helper-dependent adenoviral vectors of alternative serotype permits repeat vector administration; Gene Therapy, Sep. 1999, pp. 1565-1573, vol. 6, No. 1.

PCT International Preliminary Examination Report, PCT/EP03/50748, dated Feb. 14, 2005.

Reynolds, et al.; A targetable, injectable adenoviral vector for selective gene delivery to pulmonary endothelium in vivo; Molecular Therapy, 2(6); pp. 562-578. 2000.

Rodrigues, et al.; Single immunizing dose of recombinant adenovirus efficiently induces CD8+ T cell-mediated protective immunity against malaria, J. Immunol., Feb. 1, 1997; pp. 1268-1274, vol. 158, No. 3.

Rosenfeld, et al.; Adenovirus-Mediated Transfer of a recombinant alpha-1-Antitrypsin Gene to the Lung Epithelium in Vivo; Science, Apr. 19, 1991; pp. 431-434, vol. 252.

Roy, et al.; Circumvention of Immunity to the Adenovirus Major Coat Protein Hexon, Journal of Virology, Aug. 1998, pp. 6875-6879, vol. 72, No. 8.

Schroter, et al.; Quantitative Detection of Hepatitis C Virus RNA by Light Cycler PCR and Comparison with Two Different PCR Assays, Journal of Clinical Microbiology, Feb. 2001, pp. 765-768, vol. 39. No. 2.

Shiver, et al. ; Replication-incompetent adenoviral vaccine vector elicits effective anti-immunodeficiency-virus immunity, Nature, 2002. pp. 331-335. vol. 415, No. 6869.

Spenlehauer, et al.; A Luciferase-Reporter Gene-Expressing T-Cell Line Facilitates Neutralization and Drug-Sensitivity Assays That Use Either R5 or X4 Strains of Human Immunodeficiency Virus Type I, Virology. 2001, pp. 292-300, vol. 280.

Sprangers, et al.; Quantifying Adenovirus-Neutralizing Antibodies by Luciferase Transgene Detection: Addressing Preexisting Immunity to Vaccine and Gene Therapy Vectors, Journal of Clinical Microbiology, Nov. 2003, pp. 5046-5052, vol. 41, No. 11.

Stallwood, et al.; Neutralisation of adenovirus infectivity by ascetic fluid from ovarian cancer patients: Gene Ther. Apr. 2000; 7(8): pp. 637-643.

Stevenson. et al.; Human Adenovirus Serotypes 3 and 5 Bind to Two Different Cellular receptors via the Fiber Head Domain: Journal of Virology. May 1995, pp. 2850-2857, vol. 69, No. 5.

Stratford-Perricaudet. et al., Evaluation of the Transfer and Expression in Mice of an Enzyme-Encoding Gene Using a Human Adenovirus Vector. Human Gene Therapy, 1990, pp. 241-256, vol. 1.

Sullivan, et al.; Development of a preventive vaccine for Ebola virus infection in primates, Nature, 2000, pp. 605-609, vol. 408, No. 6812.

Taghizadeh, et al., CRF and YFP, but Not GFP, Provide Stable Fluorescent Marking of Rat Hepatic Adult Stem Cells, Journal of Biomedicine and Biotechnology, 2008, pp. 1-9, vol. 2008, Hindawi Publishing Corporation.

Tetteh, et al.; Progress and challenges towards the development of malaria vaccines, Biogruds, 2007, pp. 357-373, vol. 21, No. 6.

Vogels, et al.; Replication-Deficient Human Adenovirus Type 35 Vectors for Gene Transfer and Vaccination: Efficient Human Cell Infection and Bypass of Preexisting Adenovirus Immunity. Journal of Virology, Aug. 2003, pp. 8263-8271. vol. 77, No. 15.

Notice of Allowance for U.S. Appl. No. 11/105,725, dated Jun. 17, 2009.

| GROUP | Pre-Immunization | | Vaccination | Read-out |
|---|---|---|---|---|
| | week 0 | week 2 | week 4 | week 6 |
| 1 | Ad5ΔE3-empty | Ad5ΔE3-empty | Ad5ΔE3.mvH | Elispot/Elisa |
| 2 | Ad5ΔE3-empty | Ad5ΔE3-empty | Ad35ΔE3.mvH | Elispot/Elisa |
| 3 | PBS | PBS | Ad5ΔE3.mvH | Elispot/Elisa |
| 4 | PBS | PBS | Ad35ΔE3.mvH | Elispot/Elisa |
| 5 | PBS | PBS | PBS | Elispot/Elisa |

FIG. 8

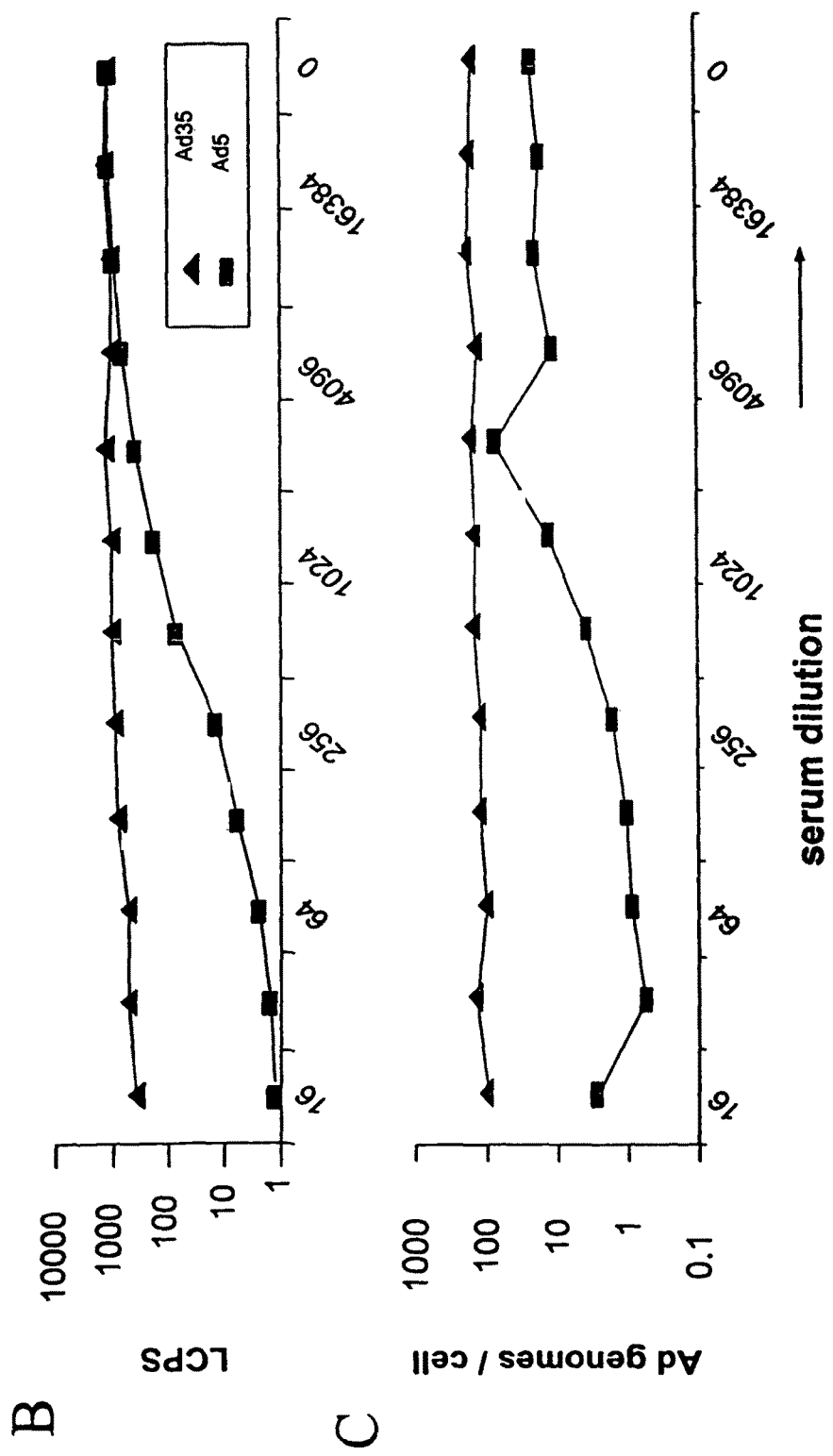
FIG. 34B/C

SETTINGS FOR RECOMBINANT ADENOVIRAL-BASED VACCINES

CROSS-REFERENCE TO RELATED APPLICATIONS

This application is a continuation of U.S. patent application Ser. No. 11/978,043, filed Oct. 25, 2007, now abandoned, which application is a divisional of U.S. patent application Ser. No. 11/105,725, filed Apr. 14, 2005, now U.S. Pat. No. 7,598,078issued Oct. 6, 2009, which is a continuation of International Patent Application No. PCT/EP03/050748, filed on Oct. 23, 2003, designating the United States of America, and published, in English, as PCT International Publication No. WO 2004/037294 A2 on May 6, 2004, which claims priority under Article 8 of the PCT to International Patent Application No. PCT NL02/00671, filed Oct. 23, 2002, the entire disclosure of each of which is incorporated herein by this reference.

TECHNICAL FIELD

The invention relates generally to the field of biotechnology, and more particularly to the field of medicine, in particular to the field of vaccination using recombinant adenoviral vectors. The invention specifically relates to the production and controlled use of vaccines based on adenoviruses derived from different serotypes.

BACKGROUND

Many different kinds of vaccines are being employed to prevent pathogenic entities to enter the body or to prevent the pathogenic entities to spread and cause illnesses. Vaccines that are being applied nowadays and/or vaccines that are being tested in different stages of development include whole-inactivated viruses, (live-) attenuated viruses, peptide vaccines, (naked) DNA vaccines, sub-unit vaccines and vaccines that are based on (relatively) harmless viruses that harbor an antigenic determinant from the pathogenic entity towards which the vaccine is directed. Examples of such "vaccine carriers" are influenza virus, alphaviruses such as Semliki Forest Virus or Sindbis virus, and adenoviruses. Wild-type adenoviruses are known to cause relatively mild diseases such as common colds. To date, over 50 different adenovirus serotypes have been identified, subdivided into six subgroups based on their sequence homologies and hemagglutination abilities. Recombinant adenoviruses are being extensively tested in HIV vaccine clinical trials and in vaccines against malaria (WO 01/02607; WO 02/22080; WO 01/21201; Sullivan et al. 2000; Shiver et al. 2002). The results that were obtained in these studies clearly show that adenoviruses provide an excellent tool for delivery of the antigen to the host. One could envision an endless list of other pathogens that could be targeted by using the adenovirus as an antigen carrier providing proper protection. Such pathogens include, but are not limited to, viruses, bacteria, yeasts, fungi, etc.

However, a few important drawbacks exist when the most common and probably the best-studied adenovirus serotype, Adenovirus 5 (Ad5) is used. As has been described extensively elsewhere (PCT International Publication WO 00/70071), it is known that most people across the world have encountered an Ad5 infection at least once in their life. This results in a level of neutralizing antibodies that is relatively high and causes a rapid clearance from the system. Moreover, it is known that almost all Ad5-derived recombinant vectors end up in the liver. This phenomenon presumably prevents the recombinant vector (based on Ad5) from very efficiently entering the antigen-presenting cells such as dendritic cells. The art has recognized that there was a need for alternative adenoviruses that would not home to the liver, but rather would be targeted to the cells involved in the immune system. One way of triggering this was by employing the receptor- or cell-binding moiety of the adenovirus. This moiety was swapped from certain adenoviruses not having a tropism for liver cells to Ad5. An example of such a recombinant adenovirus is Ad5fib16, which is a recombinant adenovirus based on Ad5, but carrying the tropism-determining part of the fiber of adenovirus serotype 16 in its capsid (see PCT International Publications WO 00/03029 and WO 02/24730).

Nevertheless, significant problems remain to be solved. Many of these are based on the finding that an infection (and injection) with a specific adenovirus elicits a significant immune response in humans and thereby hampers different kinds of vaccinations, using that same specific adenovirus serotype. Thus, if an individual has encountered a specific serotype, it is in general hard to obtain an immune response by using a vaccine based on that particular serotype. This would, therefore, limit the possible use of recombinant adenovirus as an antigen carrier for vaccination purposes.

SUMMARY OF THE INVENTION

Disclosed are methods and means for vaccination purposes utilizing recombinant adenoviral vectors. Provided is a use of a recombinant adenovirus vector of a first serotype for the preparation of a medicament for the treatment or prevention of a disease in a human or animal treated with a recombinant adenovirus vector of a second serotype, wherein the first serotype is different from the second serotype. Also described is a use of a recombinant adenovirus vector of a first serotype for the preparation of a medicament for the treatment or prevention of a disease in a human or animal having an antibody titer against an adenovirus of a second serotype, wherein the first serotype is different from the second serotype. Also provided is a kit of parts comprising a priming composition and a boosting composition, both compositions comprising: a recombinant adenovirus vector; a heterologous nucleic acid of interest present in the vector; and a pharmaceutically acceptable carrier, wherein the recombinant adenovirus vector of the priming composition is from a different serotype than the recombinant adenovirus vector of the boosting composition. Also provided is a method for determining the titer of neutralizing antibodies in a blood sample, wherein the neutralizing antibodies are directed against a virus, comprising the steps of: obtaining a sample; culturing host cells; infecting the host cells with recombinant viral vectors comprising a transgene, in the presence of the sample; and determining the activity of a protein encoded by the transgene. In another embodiment, provided is a method for determining the titer of neutralizing antibodies in a blood sample, wherein the neutralizing antibodies are directed against a virus, comprising the steps of: obtaining a sample; culturing host cells; infecting the host cells with recombinant viral vectors in the presence of the sample; and determining the number of viral genomes per cell.

Provided are methods and means that solve problems in the field of vaccination. Provided is the use of a recombinant adenovirus vector of a first serotype for the preparation of a medicament for the treatment or prevention of a disease in a human or animal treated with a recombinant adenovirus vector of a second serotype, wherein the first serotype is different from the second serotype. Also described is the use of a recombinant adenovirus vector of a first serotype for the preparation of a medicament for the treatment or prevention of a disease in a human or animal having an antibody titer against an adenovirus of a second serotype, wherein the first serotype is different from the second serotype. Preferably, the second serotype is selected from the group consisting of Ad11, Ad26, Ad34, Ad35, Ad46 and Ad49, and wherein the first serotype is selected from the group consisting of Ad11, Ad26, Ad34, Ad35, Ad46 and Ad49. Preferred are embodiments in which the first serotype according to the invention is comprised in a vaccine composition (normally a boost composition), while the second serotype is part of a priming composition. It is to be understood that it is part of the invention that if an individual does not have a high titer of neutralizing antibodies against an adenovirus serotype that is known in the art, such as Ad5, Ad2, Ad3, Ad4, Ad7 and Ad12, that the priming composition may comprise a vaccine based on such known adenovirus serotype, preferably Ad5, while the following composition (boost) should comprise another adenovirus serotype for which the individual also does not have significantly high levels of neutralizing antibodies in its serum. Of course, such following compositions may comprise an adenovirus vector selected from the same groups, as long as the first and second serotypes are different. If the human or animal has a significantly high titer to a second adenovirus (obtained through a general infection, or through active vaccination, or through a gene therapy application) the vector of choice for the first adenovirus serotype should be different from the second adenovirus serotype. "Significantly high" in this context means that such titers hamper the immune response elicited by the vector being applied, due to neutralization of the vector, hence, leading to the choice of a serotype that would not encounter titers of neutralizing antibodies that cause the immune response to be so low that a protective effect of the vaccine is not accomplished. Moreover, it is also to be understood that if a vaccine regimen requires more than two shots (prime/boost), but rather extra subsequent shots (prime/boost/boost, etc.), that this is also part of the invention: the subsequent boost compositions should always (if they comprise an adenovirus vector) comprise an adenovirus vector that is different from the adenovirus vectors that have been used previously, at least as long as the titers of neutralizing antibodies hamper the immune response required.

"Based on" or "derived from" as used herein means that a gene delivery vehicle, such as a recombinant adenovirus vector, originates from a certain wild-type adenovirus serotype as they have been recognized in the art. This means in general that certain parts of the genome are deleted to prevent replication (such as a deletion of the E1 region), but it also means that other mutations, deletions, naturally occurring chimeras, additions of nucleic acid, etc., may or may not be present in the recombinant adenoviral vector, as long as the capsid proteins towards which the neutralizing antibodies present in the serum from infected or vaccinated individuals are sufficiently different from one composition to the other. For example, if the backbone of the recombinant vector (this means generally all elements except the immunogenic and tropism-determining parts of the capsid) is identical between prime and boost compositions, this is still considered part of the invention, since the immune response towards such vectors having the same or similar backbone is still different.

In certain embodiments, the recombinant adenovirus vector of the first and second serotypes comprise essentially the same heterologous nucleic acid of interest. For vaccination purposes, it is generally required that the same antigen, or the nucleic acid encoding that antigen, is administered several times. "Essentially" as used herein refers to the idea that the antigen might be slightly different, but should still elicit an immune response that would fully (or at least sufficiently) protect the vaccinated individual from the pathogen. Generally, recombinant adenoviruses harbor the nucleic acid encoding the heterologous protein in the E1 region that is normally deleted from the genome.

In certain embodiments, the heterologous nucleic acid encodes a viral antigen. More preferably, the viral antigen is an Ebola virus antigen, a measles virus antigen or a West Nile virus antigen. Such antigens can be obtained by sequencing the genomes of the wild-type strains of the different viruses, subcloning the nucleic acids encoding the antigenic determinants from such genomes, and cloning them into the adenoviral genomic sequence.

In another embodiment, the viral antigen as described herein is an antigen from a retrovirus such as Human Immunodeficiency Virus (HIV) or a Simian Immunodeficiency Virus (SIV). Also preferred are antigens derived from Feline Immunodeficiency Virus (FIV). More preferred are embodiments wherein the HIV, SIV or FIV antigen is gag, env, nef, pol and/or combinations thereof.

In another embodiment, the heterologous nucleic acid present in the first and second serotype encodes a malaria antigen, such as the circumsporozoite (CS) or LSA-1 antigen from *Plasmodium yoelii* or *Plasmodium falciparum*, or functional equivalents or antigenic determinants/parts or derivatives thereof.

Further provided is a kit of parts comprising a priming composition and a boosting composition, both compositions comprising: a recombinant adenovirus vector; a heterologous nucleic acid of interest present in the vector; and a pharmaceutically acceptable carrier, wherein the recombinant adenovirus vector of the priming composition is from a different serotype than the recombinant adenovirus vector of the boosting composition. The recombinant adenovirus vector of the priming composition may be of a serotype selected from the group consisting of Ad11, Ad26, Ad34, Ad35, Ad46 and Ad49. Also preferred is a kit of parts according to the invention, wherein the recombinant adenovirus vector of the boosting composition is of a serotype selected from the group consisting of Ad11, Ad26, Ad34, Ad35, Ad46 and Ad49. It is still to be understood that other adenovirus serotypes may be comprised in the kit of parts according to the invention as long as the individual that is to be treated does not carry neutralizing antibodies to significantly high titers against that particular adenovirus serotype and as long as the second and first serotypes are different.

In a specific aspect of the invention, also provided is the use of a recombinant adenovirus vector derived from Ad11 for the preparation of a medicament in the treatment of a human or animal suffering from, or at risk of, a disease caused by a virus. Besides Ad35, Ad11 is a highly preferred serotype since most people in the world do not carry neutralizing antibodies against Ad11.

Also provided is a method for determining the titer of neutralizing antibodies in a human- or animal-derived blood sample, wherein the neutralizing antibodies are directed against a virus, comprising the steps of: obtaining a sample; culturing host cells; infecting the host cells with recombinant viral vectors comprising a transgene, in the presence of the sample; and determining the activity of a protein encoded by the transgene. The determined activity may be compared to a standard value. Even more preferred are methods wherein the transgene encodes a protein selected from the group consisting of luciferase, Green Fluorescent Protein (GFP) and LacZ. Also provided is a method for determining the titer of neutralizing antibodies in a blood sample, wherein the neutralizing antibodies are directed against a virus, comprising the steps of: obtaining a sample; culturing host cells; infecting the host cells with recombinant viral vectors in the presence of the sample; and determining the number of viral genomes per cell. Preferably, the number of viral genomes is compared to a standard value. Also preferred are methods, wherein the number of viral genomes per cell is determined by Quantitative-PCR (Q-PCR).

In certain embodiments, the methods are applied for determining the titer of neutralizing antibodies that are directed against an adenovirus. These antibodies might have been raised during previous vaccinations, prime and/or boost injections or through natural occurring infections. For determining the titer of neutralizing antibodies against an adenovirus, it is preferred to use a recombinant adenoviral vector in the methods of the invention. The host cells used in the method of the invention should be receptive for viral infection, preferably for adenoviral infection. A preferred cell line is the A549 cell line. Since titers may be very high, it is useful to make a curve of serial dilutions of the sample and to compare this with a standard curve.

It is very useful to know what titers of neutralizing antibodies are present in the serum of the individual to be treated. The methods known in the art are not considered accurate and useful for high throughput use. The method described herein ensures an easy way of determining the presence of neutralizing antibodies against all different adenovirus serotypes known in the art. This can then be followed by a regimen as provided by the invention in which adenovirus vectors based on different serotypes are used in subsequent vaccine applications, such as prime/boosts. It is to be understood that the method is not limited to the transgenes as described in the present disclosure, or to the materials such as antibodies as described in the provided example. The method can be executed by using a kit of parts comprising a plate, a standard curve of diluted antibodies for possibly all serotypes known and possibly materials such as buffers and antisera for detection.

Also described are methods and means to overcome at least part of the limitations of adenovirus-based vaccines. It has been recognized in the art that a series of vaccine applications would render a better and more potent immune response towards a certain immunogenic antigen. In the HIV vaccine studies (WO 01/02607; WO 02/22080), several regimens were tested, including the use of naked DNA encoding the antigen, as a priming composition, after which a boosting composition comprising a recombinant Ad5 vector was applied. Similar regimens were followed in obtaining a specific response against malaria antigens in other studies (WO 01/21201). It has been suggested in the art by several investigators to use different (low neutralized) serotypes of adenovirus in different rounds of vaccination and gene therapy applications (Parks et al. 1999; Mack et al. 1997; Hsu et al. 1992; Moffat et al. 2000; Kass-Eisler et al. 1996; Mastrangeli et al. 1996; Roy et al. 1998; Lubeck et al. 1997). However, the invention realizes that such regimens are feasible for subsequent series of vaccinations, applying different antigens directed towards different pathogens, but using the same serotype in one prime/boost setting would still render the boost immune response weaker if the same serotype would have been used in the priming composition. Settings in which different serotypes are used in a prime/boost set-up for the same vaccine have not been suggested, nor have they been used in the art. The art describes either the use of the same serotype (mostly Ad5) in prime/boost set-ups or the use of different kinds of compositions like, for instance, naked DNA encoding the antigen, and a certain serotype (being mostly Ad5) as carrier of the DNA encoding the antigen in prime/boost settings. It is now shown that pre-existing immunity against a well-known and widely used vector as Ad5 can be overcome by using a recombinant adenoviral vector that is based on an adenovirus serotype that has a low prevalence in humans and that is not neutralized by antibodies in a large percentage of the worldwide population.

Provided are methods and means for repeated vaccination applications, using different serotypes from the same subgroup. Moreover, disclosed are that, indeed, subjects that are immunized with Ad5-based vectors do not raise antibodies that are directed against a subsequent adenovirus serotype such as Ad35 or Ad11, while the titer of antibodies directed against the antigen (measles antigen H, or SIV-gag) is higher when an Ad5-Ad35 regimen is applied as compared to an Ad5-Ad5 regimen. This result strongly indicates that subsequent applications of an adenovirus of the same subgroup are not very efficient in vaccination, while subsequent applications of adenoviruses of different serotype are. These results also strongly suggest that an individual that has encountered an Ad5 infection in the past should preferably receive a priming vaccine composition comprising an adenovirus that is at least different from Ad5, while the boosting composition (if applicable) should also comprise yet another serotype that has never infected that particular individual.

Also disclosed is that cross-neutralization is not an important issue. It was widely believed that a certain extent of cross-neutralization could or may prevent the use of different adenoviruses that are extremely similar. As disclosed herein, sera that harbor neutralizing antibodies against Ad35 do not, in most cases, contain neutralizing antibodies against Ad11 and vice versa. The invention, therefore, makes it now possible to use prime/boost vaccination applications in which the priming composition comprises one adenovirus serotype, while the boosting composition comprises an adenovirus from another serotype. Disclosed are which adenovirus serotypes are suitable for such settings. Preferred serotypes that are used in prime/boost applications according to the invention are the subgroup B serotypes Ad11 and Ad35, since these serotypes encounter neutralizing antibodies in only a very limited number of human sera, while humans that have encountered Ad11 in their lifetime most likely do not contain neutralizing antibodies against Ad35, and vice versa. The chance of encountering both serotypes in one lifetime seems to be extremely slim. The use of such adenovirus serotypes, of course, would render a vaccine that needs priming and boosting compositions for a proper immune response more potent than a vaccine that is built up from serotypes that are likely to encounter neutralizing antibodies, such as Ad5.

BRIEF DESCRIPTION OF THE DRAWINGS

FIG. 8 shows the immunization schedule for the mice study.

FIGS. 34A through 34D show the different transgene activities and genomes per cell.

DETAILED DESCRIPTION OF THE INVENTION

Figure 1:
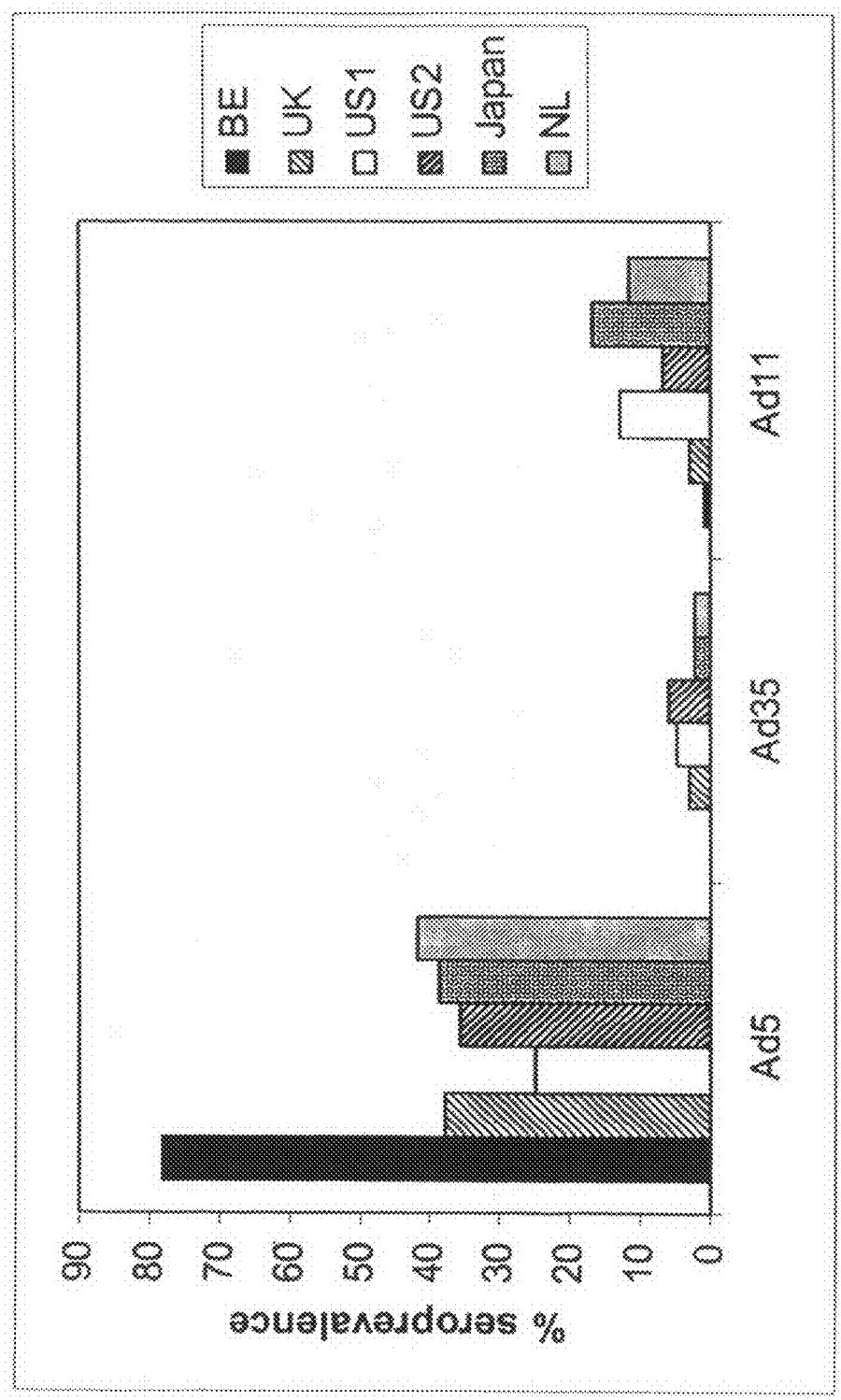
FIG. 1 is a bar graph showing the percentage of serum samples positive for neutralization (IC90 values) for Ad5, -35 and -11 in six different locations (Belgium: BE; United Kingdom: UK; United States: "US1" and "US2," Japan and The Netherlands).

Since it was found that many individuals in different populations carry neutralizing antibodies to many different serotypes, the serotype that was best suited to serve as an antigen carrier in vaccine applications or as a therapeutic/heterologous nucleic acid carrier for gene therapy applications was investigated. Only a few adenovirus serotypes encountered neutralizing antibodies in relatively few sera. The sera used in these studies were obtained from a large number of individuals from across the world, as described herein (see also, PCT International Publications WO 00/70071 and WO 02/40665 and in U.S. Pat. No. 6,492,169). Two adenoviruses of particular interest that encountered antibodies in only a few sera were Ad11 and Ad35, which are both serotypes from the B-subgroup. Generally, B-group adenovirus serotypes have a low tropism for liver cells and are capable of efficiently infecting dendritic cells in vitro. In vivo studies are hampered by the fact that mice do not seem to be a proper host for subgroup B adenoviruses. Nevertheless, Ad35 has been studied in great detail and several recombinant derivatives based on this particular adenovirus were generated (PCT International Publication WO 00/70071 and in U.S. Pat. No. 6,492,169). Since Ad5-complementing cell lines were not able to support the growth of high titers of recombinant Ad35- and Ad 11-complementing cell lines, constructs and methods were also generated to provide all necessary elements to generate batches of recombinant adenoviruses based on B-subgroup adenoviruses such as Ad35 and Ad 11 (U.S. Pat. No. 6,492, 169). The sequences of the Ad11 and Ad35 genomes were obtained in full (WO 00/70071; WO 02/53759).

Clearly, if one wants to apply a certain adenovirus serotype in a vaccine composition, one should be certain that no or a low titer of neutralizing antibodies are present in the subject that is being treated. It is known in the art that different levels of anti-adenovirus antibodies circulate in human individuals (D'Ambrosio et al. 1982) that determine the level of therapeutic preparation that should be applied. To be able to determine in vitro the anti-adenovirus antibody titers in human sera, a validated adenovirus neutralization assay is required. Such a neutralization assay is also extremely useful to monitor vaccination efficiency in experimental and clinical settings and allows standardization. Thus, one determines the titer of neutralizing antibodies against the adenovirus serotype of interest. For this, also provided is a method for determining such titers, allowing the proper adjustment of vaccine regimens suggested by the invention. In situations that such determinations are not feasible or easily accessible, for instance in mass-vaccination programs in developing countries with poor medical infrastructure or in emergency situations, the chance of success is highest by using the serotypes disclosed herein since those serotypes are unlikely to encounter neutralizing activity in most humans.

Non-limiting examples are measles, rabies virus, Ebola virus, malaria, human Metapneumovirus, etc. Antigens that could be applied are, for instance, nucleic acids encoding measles F and H, SIV-gag, Circumsporozoite (CS) protein or LSA-1 from *Plasmodium Yoelii* and *Plasmodium falciparum*, HIV-gag/pol/nef/env, and HA and NA from Influenza virus.

It is to be understood that differences in the capsid of the adenoviral vector would enable one to use the same backbone virus for subsequent vaccinations and prime/boost set ups, provided that the capsid is modified by proteins that would normally be recognized by neutralizing antibodies. For instance, an Ad5 backbone carrying a fiber and/or hexon and/or a penton protein from Ad11 could be followed by a viral vector based on Ad5 (thus, another Ad5 backbone), wherein the capsid comprises a fiber and/or hexon and/or a penton protein from Ad35 and vice versa. Such recombinant vectors are also encompassed by the invention. As long as the priming composition does not elicit an immune response that significantly hampers the infectivity of the boosting composition (as far as the adenoviral capsid proteins are concerned), then such prime and boost compositions are part of the invention.

The invention is further described with the aid of the following illustrative Examples.

EXAMPLES

Example 1

Low Prevalence of Neutralizing Activity to Ad11 and Ad35

The analysis of neutralizing activities to Adenovirus (Ad) serotypes in human sera from different geographic locations (Belgium, United Kingdom, The Netherlands, and two locations in the United States of America) has been described elsewhere (U.S. Pat. No. 6,492,169). One of the conclusions from these studies was that neutralizing activities against certain adenovirus serotypes, especially Ad35 and Ad11, were significantly lower than those directed against Ad5.

Figure 2:
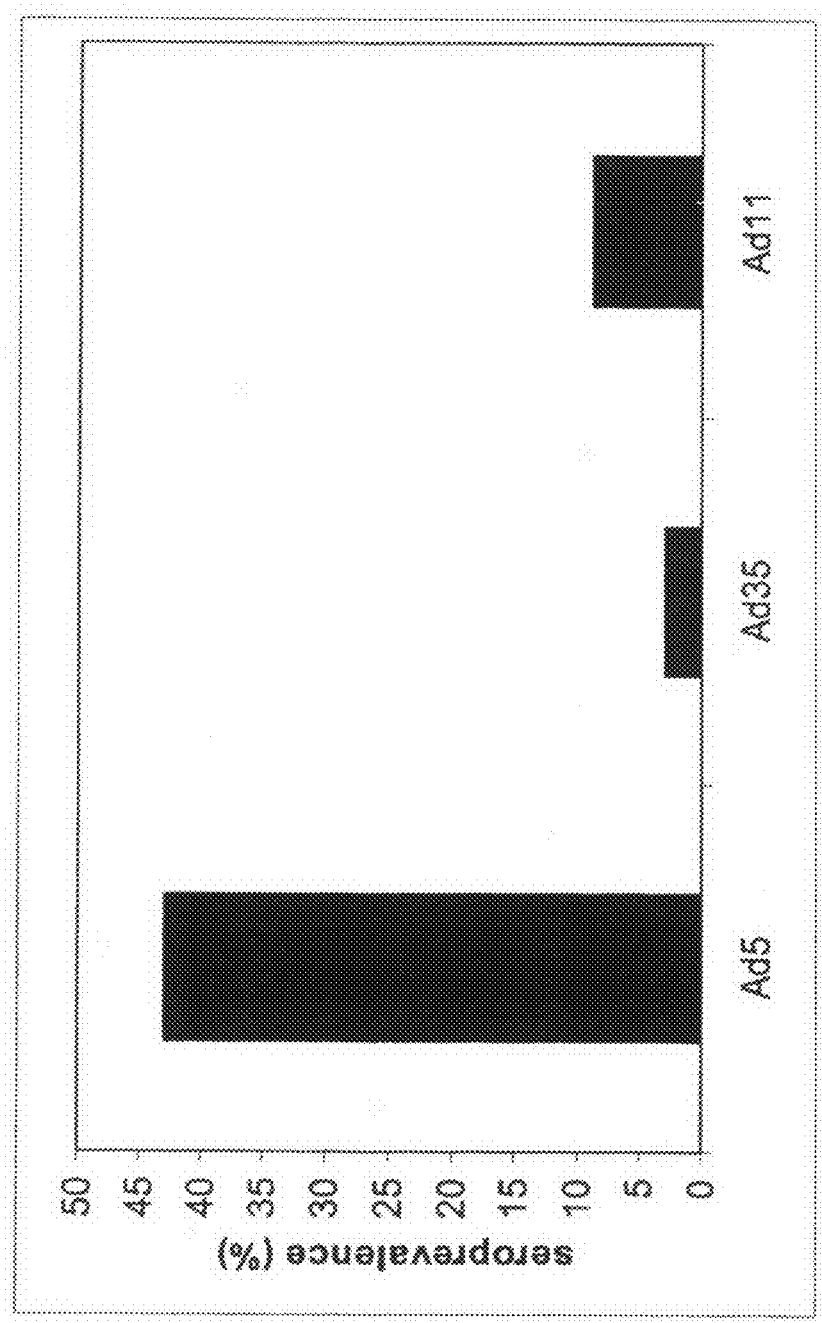
FIG. 2 is a graph showing the worldwide average percentage of serum samples positive for neutralization (IC90 values) for Ad5, -35 and -11.

For further analysis using serum from a location in the Far East, 100 serum samples were obtained from Japan. Neutralizing activities were determined by the neutralization assay described in Example 1 of U.S. Pat. No. 6,492,169. A serum was set as "non-neutralizing" when, in the well with the highest serum concentration, the protection of cyto-pathological effect (CPE) was 90% compared to the controls without serum. FIG. 1 illustrates the sero-prevalence (%) related to Ad5, Ad35 and Ad11, as determined in samples from Japan, Belgium, United Kingdom, The Netherlands and two locations in the United States of America. The average of neutralizing activities against the three different serotypes is depicted in FIG. 2. The conclusion from this comprehensive and systematic screening is that while more than 40% of the human sera contain neutralizing activity against Ad5, the prevalence of serum samples neutralizing Ad11 and Ad35 is as low as 9% and 3%, respectively. These data predict that the use of adenoviral vectors based on Ad11, as well as Ad35, will have a clear advantage over the Ad5 vectors when exploited as vaccination vectors or gene therapy vehicles in vivo or in any application where infection efficiency is hampered by neutralizing activity.

Figure 3:
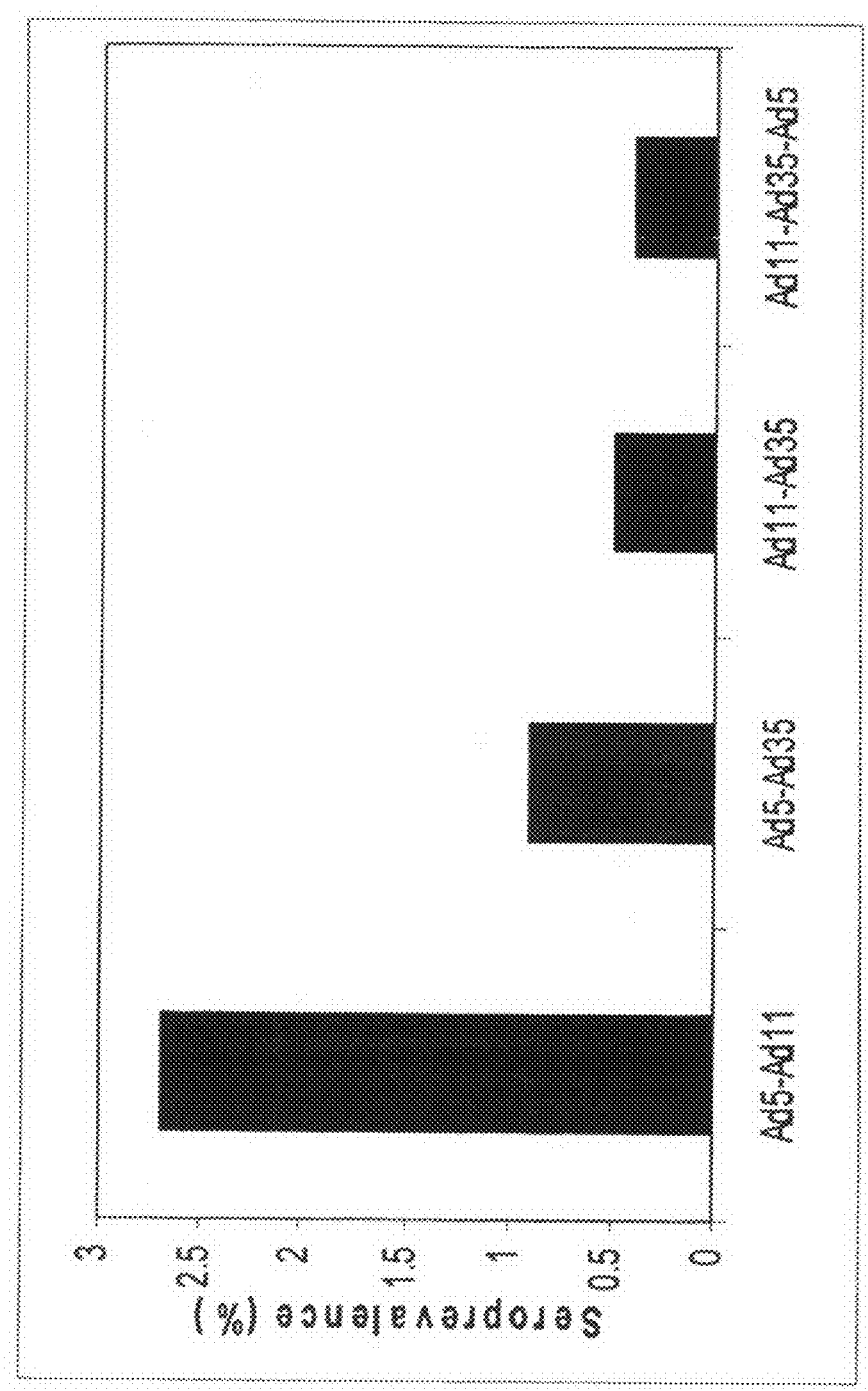
FIG. 3 is a bar graph showing the percentage of sera samples that show neutralizing activity to Ad5-Ad11, Ad5-Ad35, Ad11-Ad35 and Ad11-Ad35-Ad5.

Furthermore, data obtained from all six different geographic locations mentioned above, that were analyzed for Ad11-Ad35, Ad11-Ad5, Ad35-Ad5 and Ad11-Ad35-Ad5 neutralization activities, showed very low percentage values (FIG. 3). These results strikingly highlight the differences and clearly indicate that a serum that contains antibodies directed against a serotype from one serogroup does not necessarily contain antibodies against the other serotypes from the same subgroup. This knowledge generates the ability to exploit combinations of Ad11- and Ad35-based vectors (or other combinations of low-neutralized serotypes, within subgroups) as vaccination or gene therapy vehicles when re-administrations or distinct vaccines are required, especially in prime/boost settings. In more advanced settings one could envision screening individuals for neutralizing activity against the different serotypes and select the serotype that will encounter a low neutralizing activity and select the prime/boost set-up that suits the treated individual best.

Example 2

Generation of Recombinant Adenoviral Vaccine Vectors Based on Ad5

RCA-free recombinant adenoviruses can be generated very efficiently using adapter plasmids, such as pAdApt, and adenovirus plasmid backbones, such as pWE/Ad.AflII-rITRsp. Methods and tools have been described extensively elsewhere (U.S. Pat. Nos. 5,994,128 and 6,670,188, and International Patent Applications WO 99/55132, WO 99/64582, WO 00/70071, WO 00/03029, which references are incorporated in their entirety herein). Generally, the adapter plasmid containing the transgene of interest in the desired expression cassette is digested with suitable enzymes to free the recombinant Ad sequences from the plasmid vector backbone. Similarly, the adenoviral complementation plasmid pWE/Ad.AflII-rITRsp is digested with suitable enzymes to free the adenovirus sequences from the vector plasmid DNA.

Cloning of the Gene Encoding Hemagglutinin from Measles Virus into PiPspAdapt1.

Figure 4:
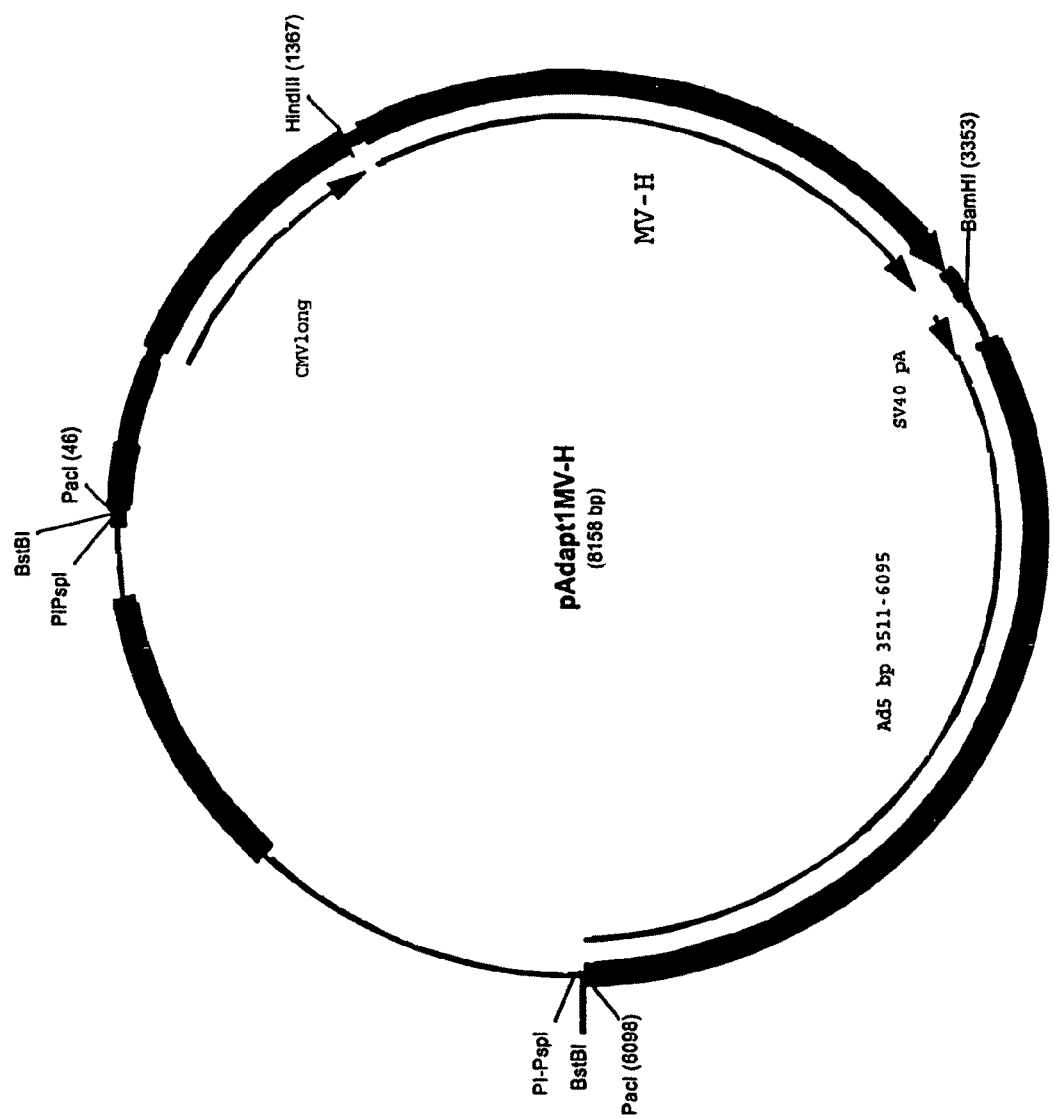
FIG. 4 is a map of pAdapt1MV-H.

The plasmid containing the gene encoding for the measles virus hemagglutinin (MV-H) protein, pECl2/Neo/HA (De Swart et al. 1998) was digested with HindIII and BamHI-restriction enzymes. The 1.6 kb fragment corresponding to the MV-H gene was isolated from agarose gel and ligated to HindIII and BamHI-digested pIPspAdapt1 vector (WO 99/64582). The resulting plasmid was named pAdapt1.MV-H and contains the MV-H gene under the transcriptional control of full-length human immediate-early (IE) cytomegalovirus (CMV) promoter and SV40 polyA(+) signal. A schematic representation of the plasmid pAdapt1.MV-His shown in FIG. 4.

Generation of Recombinant Adenovirus Ad5ΔE3.MV-H.

pAdapt1.MV-H was digested by PacI to release the left-end portion of the Ad genome. Plasmid pWE.Ad.AflII-rITR-spΔE3, containing the remaining right-end part of the Ad genome has a deletion of 1878 bp in the E3 region (XbaI deletion). This construct was also digested with PacI. Both DNAs were transfected into PER.C6™ producer cells (ECACC deposit number 96022940) using lipofectamine transfection reagent (Invitrogen) as described in WO 00/70071. Homologous recombination between overlapping sequences led to generation of recombinant Ad5ΔE3.MV-H. Ad vectors in crude lysates resulting from the transfections were plaque purified. Single plaques were analyzed for the presence of the transgene and amplified for large-scale production in triple-layer flasks (3×175 cm$^2$/flask). Cells were harvested at full CPE and the virus purified by a two-step CsCl purification procedure as routinely done by those skilled in the art of adenoviral production and generally as described in U.S. Pat. No. 6,492,169.

Cloning of SIVmac239-Gag into pAdApt.

Figure 5:
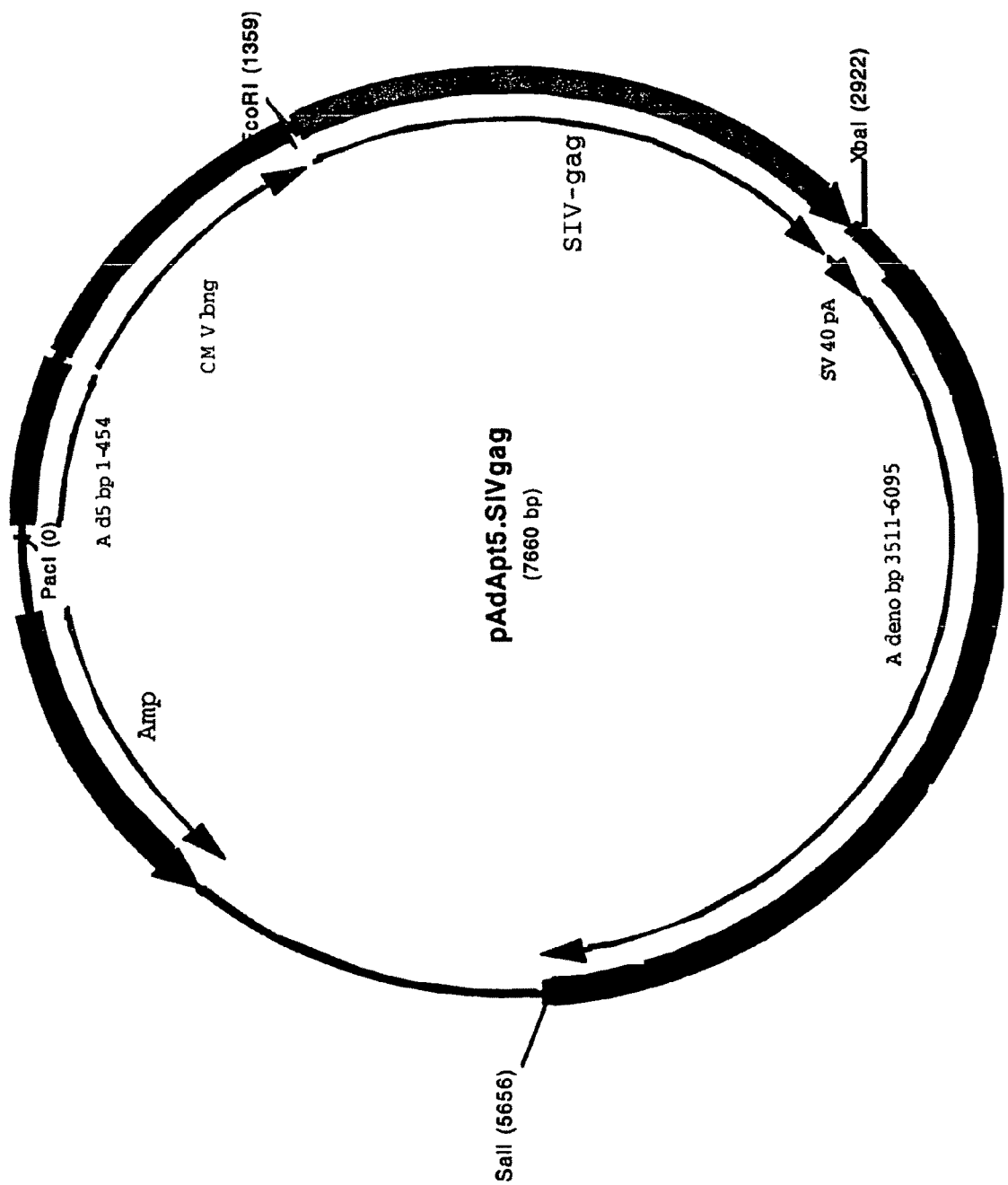
FIG. 5 is a map of pAdapt5.SIVgag.

The expression plasmid pcDNA31.51Vgag (GeneART) containing the codon optimized SIVmac239 gag gene was digested with the restriction enzymes EcoRI and XBaI. The 1.56 kb fragment corresponding to the gag gene was isolated from the agarose gel and ligated to the EcoRI and XbaI-digested pAdapt vector (WO 00/70071). The resulting plasmid that was named pAdapt-SIVgag contains the SIV-gag gene under the transcriptional control of the full-length CMV promoter and the SV40 polyA(+) signal. A schematic representation of the plasmid pAdapt5-SIVgag is shown in FIG. 5.

Generation of Recombinant Adenovirus Ad5ΔE3.SIVgag.

pAdapt5-SIVgag was digested with the restriction enzymes PacI and SalI to release the left-end portion of the Ad genome from the plasmid backbone. The plasmid pWE.Ad.AflII-rITRΔE3, containing the remaining right-end part of the Ad genome with an 1878 bp deletion in the E3 region, was digested with PacI. Both DNAs are transfected into PER-E1B55K producer cells (U.S. Pat. No. 6,492,169; also referred to as PER.C6/55K cells) using lipofectamine transfection reagent (Invitrogen). Homologous recombination between the two overlapping sequences led to generation of recombinant Ad5ΔE3.SIVgag (generally referred to as Ad5-SIVgag). Ad vectors in crude lysates resulting from this transfection were plaque purified. Single plaques were analyzed for the presence of the transgene and amplified for large-scale production in triple-layer flasks (3×175 cm²/flask). The culture was harvested at full CPE and the virus purified by a two-step CsCl purification procedure and dialyzed three times into phosphate-buffered saline (PBS) containing 5% sucrose, as routinely done for adenoviruses and generally as described in U.S. Pat. No. 6,492,169. Adenovirus titers were measured as virus particles by HPLC using methods known to persons skilled in the art. Infectivity was measured as plaque-forming units by using PER-E1B55K cells. SIVgag protein expression from the recombinant virus was determined by infection of A549 cells followed by analysis of culture supernatants using a commercial Gag ELISA kit (Murex Biotech, Ltd, UK). Generation of the recombinant adenovirus named Ad5ΔE3.empty (generally referred to as Ad5-empty) was carried out as described above, using as adapter DNA the plasmid pAdapt lacking a transgene.

Example 3

Generation of Recombinant Adenoviral Vaccine Vectors Based on Ad35

RCA-free recombinant adenoviruses based on Ad35 are generated very efficiently using adapter plasmids, such as pAdApt35Ip1 (containing Ad35 nucleotides 1-464 and 3401-4669; WO 00/70071) and pAdApt535 (see below), and adenovirus plasmid backbones, such as pWE/Ad35.pIX-rITRΔE3 (U.S. Pat. No. 6,492,169).

Cloning of the Measles Virus Hemagglutinin into pAdApt35IP1.

Figure 6:
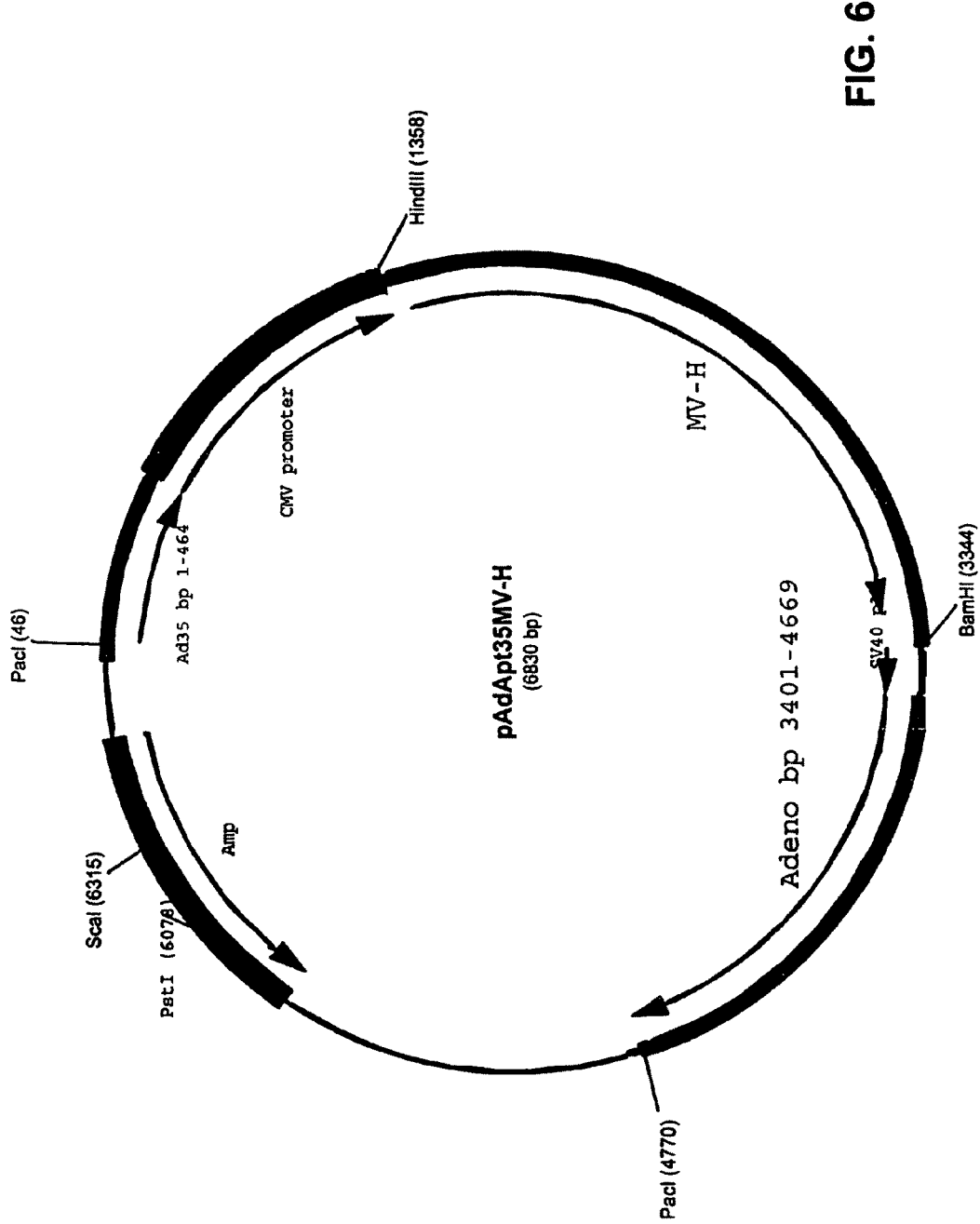
FIG. 6 is a map of pAdapt35MV-H.

The plasmid containing the gene encoding for the measles virus hemagglutinin (MV-H) protein pEC12/Neo/HA was digested with HindIII and BamHI. The 1.6 kb fragment corresponding to the MV-H gene was isolated from agarose gel and ligated to HindIII and BamHI-digested pAdApt35IP1 vector (WO 00/70071). The resulting plasmid was named pAdApt35.MV-H and contains the MV-H gene under the transcriptional control of the full-length human CMV promoter and SV40 polyA(+) signal. A schematic representation of pAdApt35.MV-H is shown in FIG. 6.

Generation of Recombinant Adenovirus Ad35ΔE3.MV-H.

pAdApt35.MV-H was digested by PacI to release the Ad sequences from the plasmid backbone. Plasmid pWE.Ad35.pIX-rITRΔE3, containing the remaining right-end part of the Ad genome with 2673 bp deletion in the E3 region, was digested with NotI. Both DNAs were transfected into PER-E1B55K producer cells using lipofectamine transfection reagent (Invitrogen). The PER-E1B55K cell line is based on PER.C6 cells that were modified by carrying an E1B 55K gene fragment of adenovirus serotype 35, thereby enabling growth of subgroup B adenoviruses to high titers on a complementing cell line such as PER.C6 (see, for details, U.S. Pat. No. 6,492,169). Homologous recombination between the two overlapping sequences led to generation of recombinant Ad35ΔE3.MV-H. Ad vectors in crude lysates resulting from the transfections were plaque purified. Single plaques were analyzed for the presence of the transgene and amplified for large-scale production in triple-layer flasks (3×175 cm²/flask). Cells were harvested at full CPE and the virus purified by a two-step CsCl purification procedure as routinely done by those skilled in the art for adenoviruses and generally described in U.S. Pat. No. 6,492,169.

Cloning of SIVmac239-gag into pAdApt535.

Figure 7:
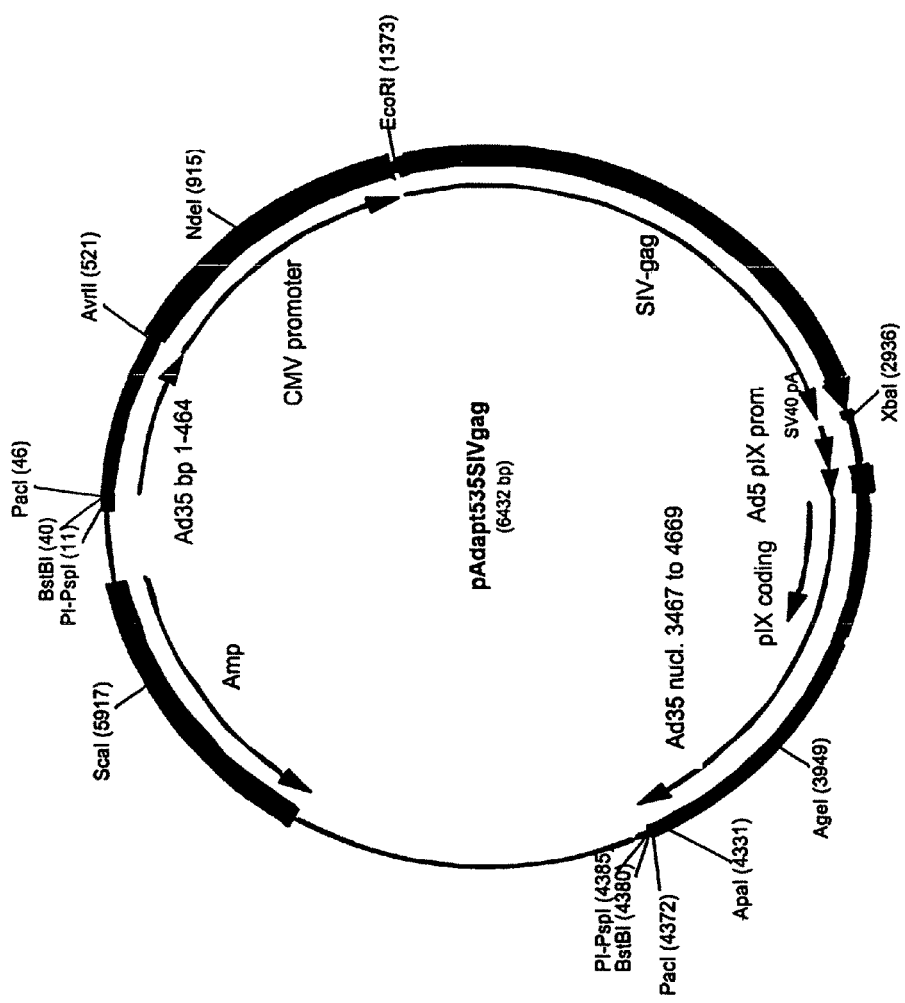
FIG. 7 is a map of pAdapt535.51Vgag.

Plasmid pcDNA31.51Vgag (GeneART) containing the codon optimized SIVmac239 gag gene was digested with the restriction enzymes EcoRI and XbaI. The 1.56 kb fragment corresponding to the gag gene was isolated over agarose gel and ligated to the EcoRI and XbaI-digested pAdApt535 vector. The resulting plasmid was named pAdApt535-SIVgag and contains the SIV-gag gene under the transcriptional control of the full-length human CMV promoter and the SV40 polyA(+) signal. A schematic representation of the plasmid pAdApt535-SIVgag is shown in FIG. 7.

Generation of Recombinant Adenovirus Ad35ΔE3.SIVgag.

DNA of pAdApt35-SIVgag was digested with the restriction enzymes PacI to release the Ad sequences from the plasmid backbone. Plasmid pWE.Ad35.pIX-rITRΔE3, containing the right-end part of the Ad genome with 2673 bp deletion in the E3 region, was digested with NotI. Both DNAs were transfected into PER-E1B55K producer cells using lipofectamine transfection reagent. Homologous recombination between the two overlapping sequences led to generation of recombinant Ad35ΔE3.SIVgag virus (generally referred to as Ad35-SIVgag). Adenovirus vectors in crude lysates resulting from this transfection were plaque purified. Single plaques were analyzed for the presence of the transgene and amplified for large-scale production in triple-layer flasks (3×175 cm²/flask). The culture was harvested at full CPE and the virus was purified by a two-step CsCl purification procedure and dialyzed three times into phosphate-buffered saline (PBS) containing 5% sucrose, as routinely done for adenoviruses and generally as described in U.S. Pat. No. 6,492,169. Adenovirus titers were measured as virus particles by HPLC using methods known to persons skilled in the art. Infectivity was measured as plaque-forming units by using PER-E1B55K cells. SIV-gag protein expression from the recombinant virus was determined by infection of A549 cells followed by analysis of culture supernatants using a commercial Gag ELISA kit (Murex Biotech, Ltd.). Generation of the recombinant adenovirus named Ad35ΔE3.empty was carried out as described above, using as adapter DNA the plasmid pAdApt35 with no transgene.

Example 4

Recombinant Ad35ΔE3.MV-H Elicits Measles-Specific Immunity in Mice Pre-Exposed to Ad5

Figure 9:
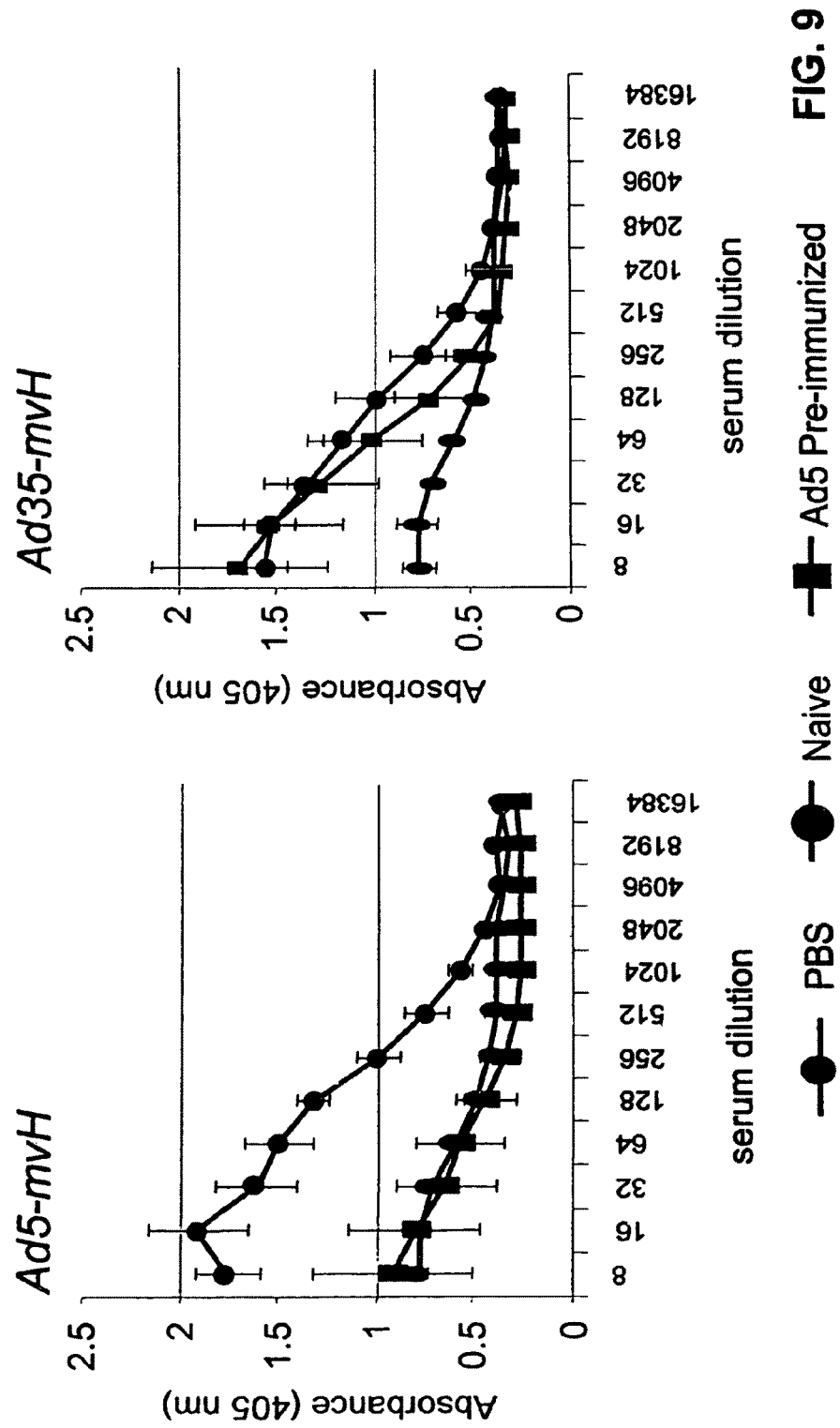
FIG. 9 shows the anti-measles IgG response in mice after Ad5.MV-H (left) and Ad35.MV-H (right) vaccination as measured by ELISA assay.
Figure 10:
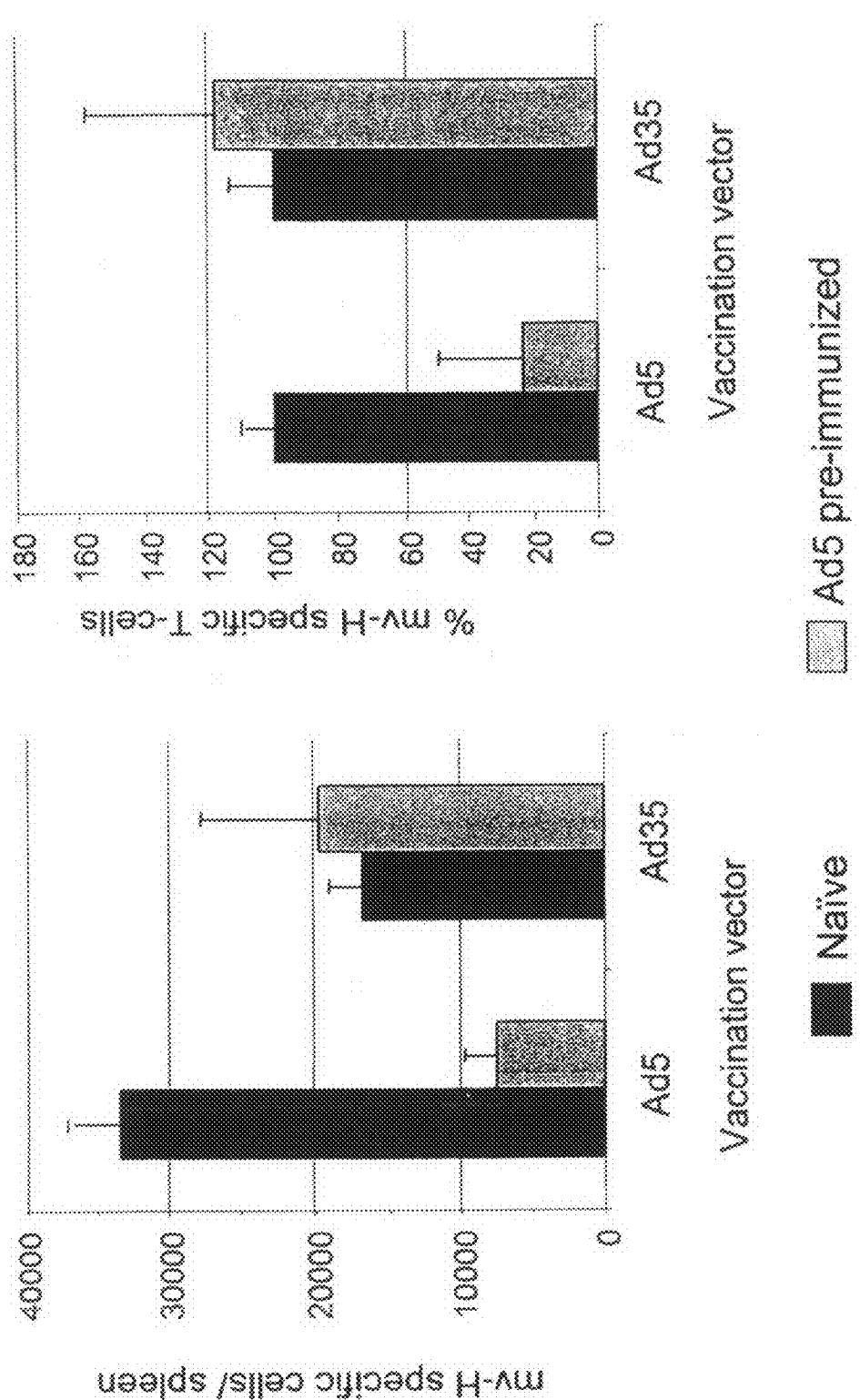
FIG. 10 shows the anti-measles T-cell response in mice after Ad5.MV-H and Ad35.MV-H vaccination as measured by ELISPOT assay. Left: a bar graph showing the values of MV-H-specific cells per spleen. Right: a bar graph showing the percentage values of MV-H-specific T-cells.

The capacity of recombinant Ad35ΔE3.MV-H vector to induce measles immunity in vivo in the presence of Ad5 antibodies was investigated. The study enrolled 25 Balb/C mice (female, 12 weeks old) distributed in five experimental groups of five mice each. At week 0 (day 0) and week 2 (day 14), mice were intravenously (i.v.) injected with either $10^{10}$ vp of Ad5Δ3-empty (groups 1 and 2) or sterile PBS (groups 3, 4 and 5) in a volume of 200 µl. Inducing pre-existing immunity may be performed through i.v. injections as described here, but also with intra-muscular (i.m.) injections, while all adenovirus priming and boosting injections for raising an immune response are all performed with i.m. injections. At week 4 (day 28), mice belonging to groups 1 and 3 were vaccinated by intra-muscular injection of $10^{10}$ vp of Ad5ΔE3.MV-H. Similarly, mice of groups 2 and 4 received $10^{10}$ vp of Ad35ΔE3.MV-H in a volume of 200 µl. Also at day 28, mice of group 5 were injected with PBS (FIG. 8). Two weeks after vaccination at day 42, cellular and humoral immunity was determined by the ELISPOT and ELISA assays, respectively. Procedures for these assays are described below. Efficient Ad35ΔE3.MV-H-mediated anti measles-H IgG response was obtained in naïve mice (group 4) as well as in mice pre-exposed to Ad5 (group 2). In contrast, Ad5ΔE3.MV-H-induced anti measles-H IgG response was observed only in naïve mice (group 3), whereas no significant levels of anti-measles antibodies were detected in mice pre-exposed to Ad5 (FIG. 9). Similarly, efficient measles-H T-cell response was observed in all animals vaccinated with Ad35ΔE3.MV-H and in the naïve mice vaccinated with Ad5ΔE3.MV-H. In contrast, measles-H T-cell response was dramatically hampered in mice exposed to Ad5 prior to vaccination (FIG. 10). These results demonstrate that Ad35-based vectors can efficiently induce anti-measles immunity. Furthermore, Ad35ΔE3.MV-H-mediated anti-measles IgG and T-cell response was not impaired by the presence of anti-Ad5 immunity, thus strengthening the rationale to exploit a vector based on an adenovirus against which the prevalence of neutralizing activity is low (worldwide).

The ELISPOT assay was performed as follows. The mouse fibroblast cell line 3T3, syngeneic to BALB/c mice, was used as target cell line to stimulate mouse effector T-cells. At day −3 before start of the ELISPOT assay, 3T3 cells were seeded at the density of $10^5$ cells/ml in DMEM medium, in 6-well plates, and allowed to attach to the well bottom during 5 hours of incubation at 37° C., 10% $CO_2$ atmosphere. Then, Ad vectors were added at moi of $10^5$ vp/cell. Used vectors were Ad5.empty, Ad35.empty, Ad5ΔE3.MV-H and Ad35ΔE3.MV-H. Uninfected 3T3 were reserved for negative controls. At day −1, multiscreen 96-well filtration plates (MAHA S45 10, Millipore) were pre-incubated with 0.5 μg/100 μl IFNγ antibody (Becton Dickinson) per well, at 4° C. overnight. The next day, wells were emptied, and blocked for 1 hour at 37° C. with culture medium Iscoves supplemented with 10% FBS. At day 0, mouse splenocytes were harvested from isolated spleen, and washed in Iscoves culture medium. Viable cells were counted by trypan blue exclusion, and cell suspension adjusted to $10^6$ cells/ml. These "effector" spleen cells were seeded at the density of $10^5$/100 μl/well, in the pre-coated ELISPOT plate. Target cells were harvested and resuspended in Iscoves culture medium and adjusted to $10^6$ cells/ml. 20 U/ml of rh. IL2 (Chiron) was added to target cell suspensions. Subsequently, 100 μl of target cells were added in each well containing the effector cells. ELISPOT plates were incubated overnight at 37° C., 10% $CO_2$. On day 1, plates were emptied and washed six times with PBS/0.05% TWEEN, and five times with water. Second antibody, biotin rat-anti-mouse IFNγ (Becton Dickinson), was added to each well in 100 μl of a 2.5 μg/ml PBS/0.05% TWEEN solution. Plates were incubated for 1 hour at 37° C., and washed six times with PBS/TWEEN. Extravidine-alkaline (Millipore) was diluted 1:2000 in PBS/0.05% TWEEN/1% BSA, and added 100 μl per well. Plates were incubated for 1 hour at RT. A tablet of BCIP-NBT (Millipore) was dissolved in 10 ml milliQ water, protected from light. Plates were washed three times with PBS/TWEEN and three times with PBS. The substrate BCIP-NBT solution was added to each well (100 μl/well), and incubated at RT. After approximately 10 minutes when spots became visible, reaction was stopped by the addition of tap water. Plates were rinsed in tap water, dried and analyzed in an AELVIS ELISPOT reader (CLB).

The ELISA assay was generally performed as follows. High affinity ELISA plates (Greiner) were coated with inactivated measles (provided by RIVM, The Netherlands) 1:25 diluted in $H_2O$ (50 μl per well). Plates were incubated under UV for 1 hour. Plates were washed and blocked with 200 μl PBS/1% BSA, for 1 hour at 37° C., 10% $CO_2$ atmosphere. Plates were washed four times with 200 μl PBS/0.05% TWEEN. In wells 2-12, 50 μl PBS were dispensed. In well 1, 25 μl serum and 75 μl PBS were added and serial dilutions were made by transferring 50 μl from wells 1 to 2, 2 to 3, etc., through wells 11; wells 12 were left without serum. Plates and serum were incubated for 1 hour at 37° C., 10% $CO_2$ atmosphere. Plates were washed four times with PBS/0.05% TWEEN 200 μl/well. To each well, 50 μl of IgG-HRP (Rockland), 1:1000 diluted in PBS, were added and incubated for 1 hour at 37° C., 10% $CO_2$ atmosphere. Plates were washed four times with 200 μl/well PBS/0.05% TWEEN. 100 μl/well ABTS substrate (Roche) was added, and incubated for 1 hour at 37° C., 10% $CO_2$ atmosphere. Samples were measured for Optical Density at a wavelength of 405 nm.

Example 5

Figure 11:
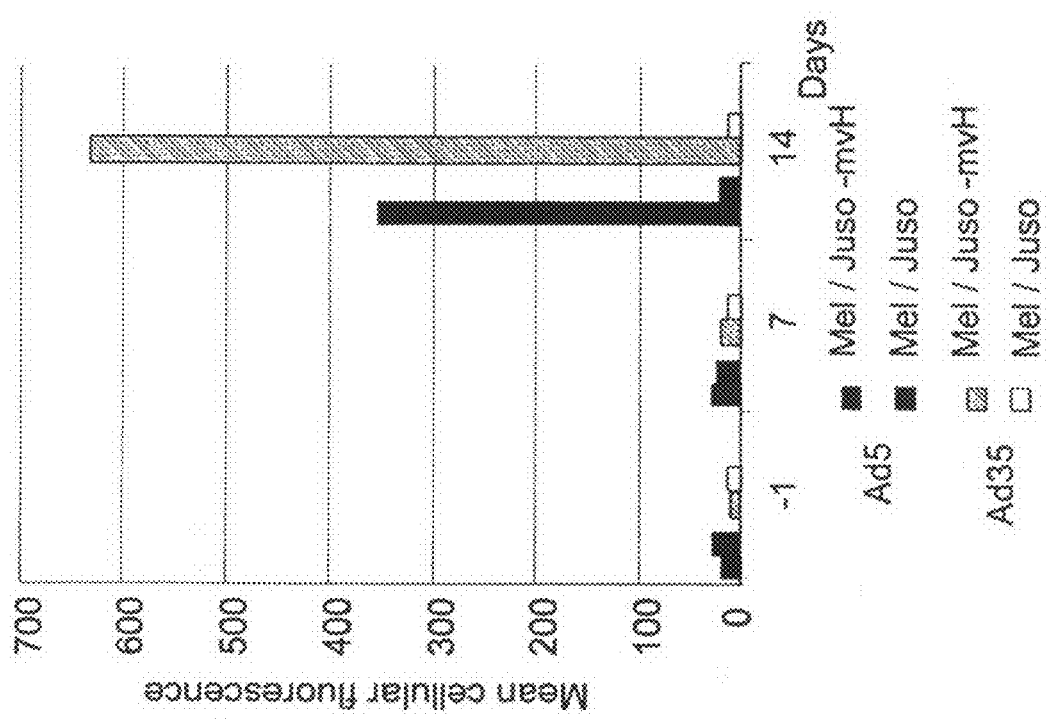
FIG. 11 shows the anti-measles antibody response in cynomolgus monkeys after Ad5.MV-H and Ad35.MV-H vaccination as measured by MV-H-specific immunofluorescence assay.

Ad35ΔE3.MV-H Versus Ad5ΔE3.MV-H-Mediated Anti-Measles Response in Cynomolgus Monkeys The potency of the Ad35 vaccine vector in a non-human primate model was investigated in an in vivo study using cynomolgus monkeys. At day 0, two monkeys were vaccinated by intra-muscular injection with $8 \times 10^{10}$ vp of either Ad35ΔE3.MV-H or Ad5ΔE3.MV-H. At day 7 and day 14 post-vaccination, animal sera were collected to be analyzed for the presence of anti-measles IgG using the MV-H-specific immunofluorescence test as described herein. As shown in FIG. 11, both monkeys developed a relevant anti-measles antibody titer as measured on day 14 post-injection with mean cellular fluorescence values of 352 (Ad5 vaccinated monkey) and 626 (Ad35 vaccinated monkey), therefore demonstrating the potency of the Ad35-based vector in a side-by-side comparison with the Ad5-based vector.

Example 6

Figure 12:
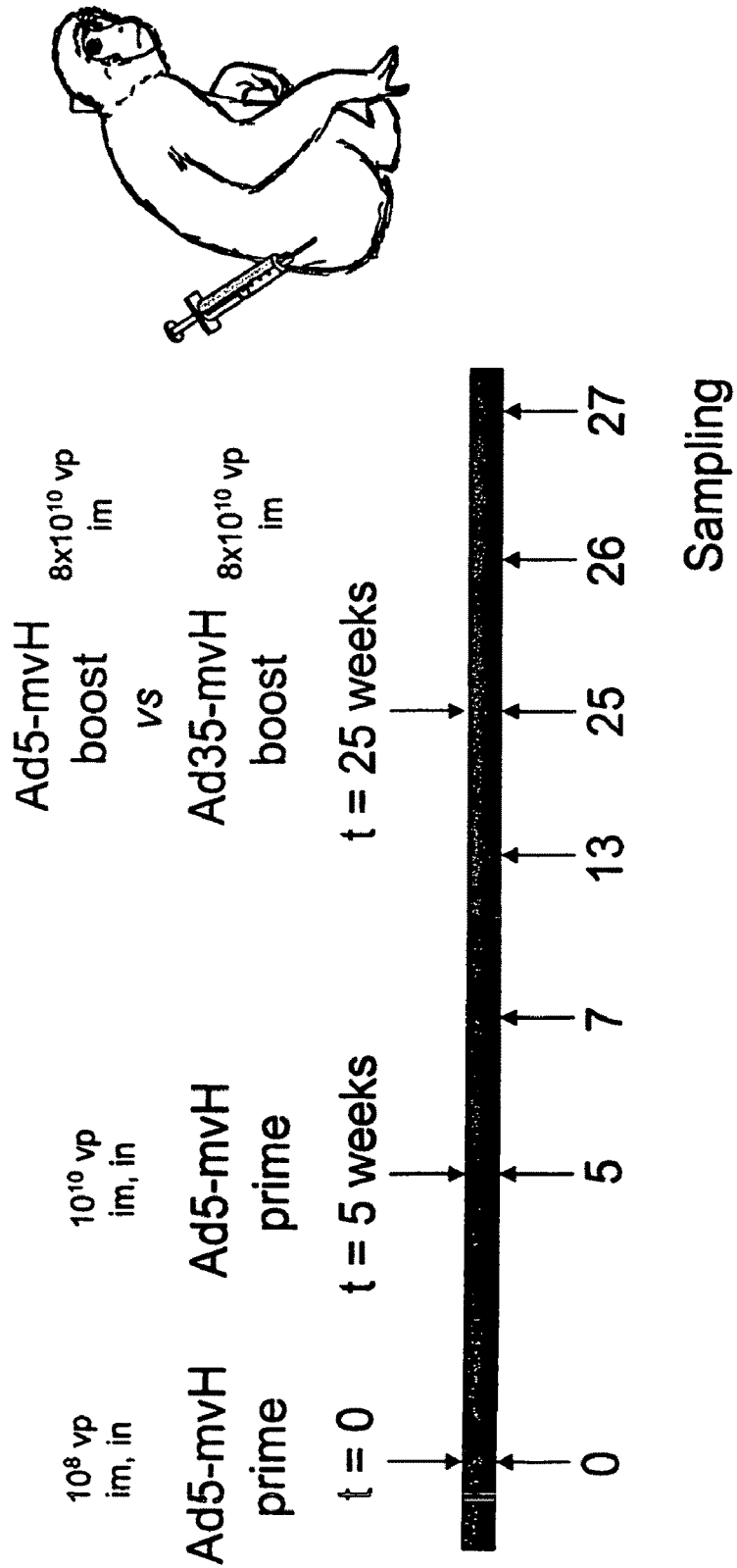
FIG. 12 is a table showing immunization schedule and time points for blood sampling for the in vivo study in cynomolgus monkeys.
Figure 13:
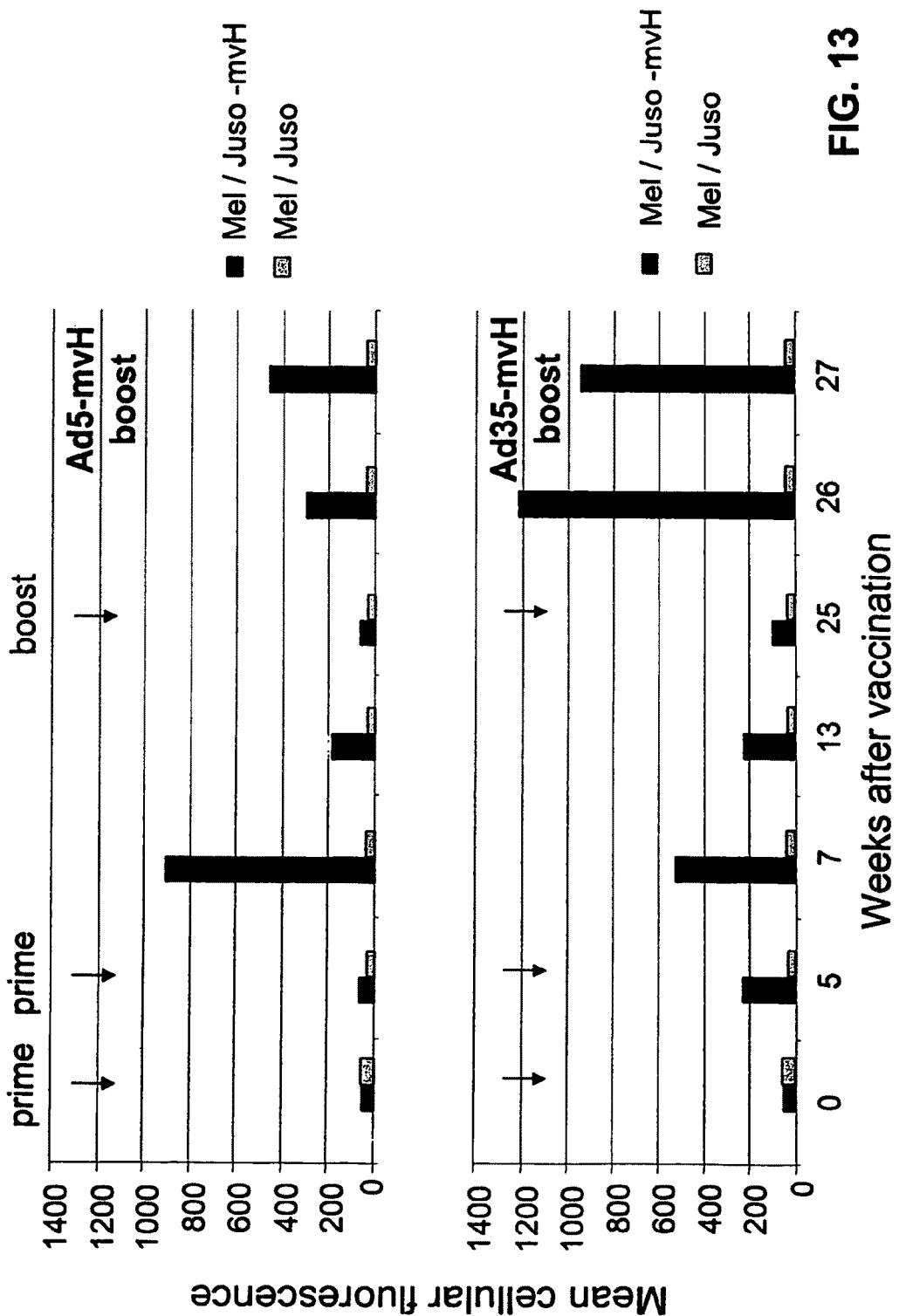
FIG. 13 shows the anti-measles antibody response in cynomolgus monkeys after Ad5.MV-H prime and Ad5.MV-H or Ad35.MV-H boost vaccination as measured by MV-H-specific immunofluorescence assay.

Ad35ΔE3.MV-H Versus Ad5ΔE3.MV-H Anti-Measles Boost Activity in Cynomolgus Monkeys Primed with Ad5ΔE3.MV-H Vaccine The capacity of Ad35ΔE3.MV-H vector to boost measles immunity in cynomolgus monkeys primed with Ad5ΔE3.MV-H vector was investigated. The vaccination regimen was as follows: at week 0 and week 5, two monkeys were primed with Ad5ΔE3.MV-H by intra-muscular injection of $10^8$ vp (at week 0) and $10^{10}$ vp (at week 5). At week 25, the animals received a booster vaccination with an intra-muscular injection of $8 \times 10^{10}$ vp of either Ad5ΔE3.MV-H or Ad35ΔE3.MV-H. Time course of the experiment showing time points of blood sampling and vaccination schedule is depicted in FIG. 12. Animal sera were analyzed for the presence of anti-MV-H antibodies using the MV-H-specific immunofluorescence test as described herein. As shown in FIG. 13, relevant anti-measles immunity was induced in the two vaccinated monkeys. However, the combination Ad5 prime/Ad35 boost gave rise to the highest immuno response thus indicating the advantage offered by a prime/boost mixed-modality.

The MV-H-specific immunofluorescence test was performed as described below. Pre-established Mel/Juso cell lines stably expressing the MV-H protein were used. Incubation of these cells with serum allows binding of antibodies to MV-H (parental Mel/Juso cells serve as control). After excess serum is removed, antibodies bound to MV-H are detected using fluorescent-labeled antibodies specific for IgG and flow cytometry. The assay was generally performed as follows:

Mel/Juso cells stably expressing MV-H as well as the parental cells were seeded in 96-well V-bottom plates at the concentration of $10^5$ cells/well in 90 µl PBS supplemented with 3% bovine serum (P3F). Plasma samples were heat-inactivated at 56° C. and diluted 1:10 in P3F. 10 µl of pre-diluted plasma was added to the cells and incubated at 4° C. for 1 hour. Then, cells were washed and subsequently incubated with anti-human IgG conjugated with FITC (DAKO) diluted in 100 µl P3F. After 1 hour at 4° C., cells were washed, resuspended in 200 µl PBS and finally measured on the FACScan.

Example 7

Comparison of Recombinant Ad5 Versus Ad35 as Vaccine Vectors and Efficacy of Prime/Boost Regimens with Different Serotypes Ad Vectors in Monkeys Ad5 vectors have been demonstrated to induce effective anti-immunodeficiency-virus immunity (Shiver et al. 2002). A side-by-side comparison between Ad5 and Ad35 vectors is designed to investigate the ability to induce immunity and protection against immunodeficiency virus in rhesus monkeys. In addition, the efficacy of prime/boost regimens with different Ad vectors serotypes is evaluated. The study enrolls 24 rhesus monkeys distributed in four experimental groups of six monkeys each. Animals are immunized by intra-muscular injection of $10^{11}$-$10^{12}$ of recombinant Ad5ΔE3 or Ad35ΔE3 viral vectors carrying either the SIVmac239 gag gene (Ad5-SIVgag or Ad35-SIVgag) or no transgene (Ad5-empty or Ad35-empty). Immunization is carried out as follows: monkeys belonging to group 1 are vaccinated with Ad5-SIVgag at month 0 (prime) and month 6 (boost). Similarly, monkeys of group 2 are vaccinated with Ad35-SIVgag at month 0 (prime) and month 6 (boost). Monkeys of group 3 are vaccinated with Ad5-SIVgag at month 0 (prime) and with Ad35-SIVgag at month 6 (boost). Finally, monkeys of group 4 (control group) are vaccinated with Ad5-empty at month 0 (prime) and Ad35-empty at month 6 (boost). Cellular and humoral responses are monitored with immunological assays well known to persons skilled in the art. To evaluate efficacy of the immunity, three months after the last vaccination, animals are challenged with 50 MD50 SHIV-89.6p virus (Beth Israel Deaconess Medical Center).

While attenuation of SHIV-89.6p virus infection in Ad5-SIVgag vaccine recipients is predicted (Shiver et al. 2002), vaccine regimens based on Ad35 alone or Ad5/Ad35 combinations are expected to be superior or at least comparable in efficacy as compared to regimens based solely on Ad5. In contrast to the findings in mice (Example 9) showing that Ad35 is less potent than Ad5 in naïve mice, it is expected that Ad35 would elicit at least a comparable immune response in monkeys as would be found with Ad5, because the receptor-binding and/or receptor-recognition is expected to be better in monkeys than in mice (see the discussion about the CAR and CD46 receptors in Example 9).

Example 8

Effect of Pre-Existing Ad5 Immunity on Immunogenicity of Ad35 Vaccine Vector in Monkeys The ability of Ad35 to induce immunity and protection against immunodeficiency virus in rhesus monkeys in the presence of Ad5 pre-existing antibodies is tested. Furthermore, the efficacy of prime/boost regimens with different Ad vectors serotypes is evaluated.

This study enrolls 18 monkeys distributed in three experimental groups of six monkeys each. All animals are pre-immunized at months 0 and 2 with $10^{11}$-$10^{12}$ vp of Ad5-empty by intra-muscular injection. At month 4 (prime), monkeys of groups 1 and 3 are injected with $10^{11}$-$10^{12}$ vp of Ad5-SIVgag, whereas monkeys of group 2 receive $10^{11}$-$10^{12}$ vp of Ad35-SIVgag. At month 10, monkeys are boosted with $10^{11}$-$10^{12}$ vp of Ad5-SIVgag (group 1) or Ad35-SIVgag (groups 2 and 3). Cellular and humoral responses are monitored with immunological assays well known to those skilled in the art. To evaluate efficacy of the immunity, three months after the last vaccination, animals are challenged with MD50 SHIV-89.6p virus. It is expected that pre-existing immunity towards Ad5 viruses would elicit a negative effect to a subsequent recombinant Ad5 administration and thus would give less protection against a SHIV challenge, while a subsequent recombinant Ad35 administration would not be hindered by the pre-existing immunity that was raised to the Ad5 viruses and therefore give rise to a proper protection against a SHIV challenge.

Example 9

Effect of Pre-Existing Immunity on Immunogenicity of the Ad35-SIVgag Vaccine Vector in Mice Six to eight week-old C57/BL6 or Balb/c mice were purchased from Charles River Laboratories (Wilmington, Mass.). For recombinant Ad5 and Ad35 virus immunizations, mice were injected intramuscularly (i.m.) with $10^8$ or $10^{10}$ vp replication-incompetent E1-deleted Ad5 or Ad35 expressing SIVmac239 Gag (SIVgag) in 100 µl sterile PBS in the quadriceps muscles. For DNA immunizations, mice were injected i.m. with 50 µg plasmid VRC-4307 expressing SIVmac239 Gag-Pol-Nef (Vaccine Research Center, National Institutes of Health) in 100 µl sterile PBS. For rMVA immunizations, mice were injected i.p. with $10^8$ pfu rMVA-T338 expressing SIVmac239 Gag in 100 µl sterile PBS (Therion Biologics). Recombinant MVA is generally administered i.p., although other routes may be used as well. To induce active anti-Ad5 immunity, mice were pre-immunized either once or twice separated by a four-week interval i.m. with $10^{10}$ vp Ad5-Empty containing no insert in 100 µl sterile PBS.

Gag-specific cellular immune responses were assessed by interferon-γ (IFN-γ) ELISPOT assays using murine splenocytes in response to individual Gag epitope peptides or a pool of overlapping 15 amino acid peptides covering the entire SIVmac239 Gag protein. 96-well multi-screen plates (Millipore) coated overnight with 100 µl/well of 10 µg/ml rat anti-mouse IFN-γ (Pharmingen) in PBS were washed three times with endotoxin-free Dulbecco's PBS (Life Technologies) containing 0.25% TWEEN-20 and blocked with PBS containing 5% FBS for 2 hours at 37° C. The plates were washed three times with Dulbecco's PBS containing 0.25% TWEEN-20, rinsed with RPMI 1640 containing 10% FBS, and incubated in triplicate with $2\times10^5$ or $5\times10^5$ splenocytes per well in a 100 µl reaction volume containing 1 µg/ml peptide. For studies utilizing the Gag peptide pool, each peptide in the pool was present at 1 µg/ml. Following an 18-hour incubation, the plates were washed nine times with Dulbecco's PBS containing 0.25% TWEEN-20 and once with distilled water. The plates were then incubated for 2 hours with 75 µl/well of 5 µg/ml biotinylated rat anti-mouse IFN-γ (Pharmingen), washed six times with Coulter Wash (Coulter Corporation), and incubated for 2 hours with a 1:500 dilution of streptavidin-AP (Southern Biotechnology Associates). Following five washes with Coulter Wash and once with PBS, the plates were developed with NBT/BCIP chromogen (Pierce), stopped by washing with tap water, air dried, and read using an ELISPOT reader (Hitech Instruments). For depletion studies, splenocytes were incubated with magnetic microbeads coated with anti-CD4 (L3T4) or anti-CD8 (Ly-2) mAbs (Miltenyi Biotec) and separated using MiniMACS columns prior to performing the ELISPOT assay. Cell depletions were approximately 95-98% efficient.

A direct ELISA-measured serum anti-Gag antibody titers from immunized mice. 96-well plates coated overnight with 100 µl/well of 1 µg/ml recombinant SIV-gag protein (Intracel) in PBS were blocked for 2 hours with PBS containing 2% BSA and 0.05% TWEEN-20. Sera were then added in serial dilutions and incubated for 1 hour. The plates were washed three times with PBS containing 0.05% TWEEN-20 and incubated for 1 hour with a 1:2000 dilution of a peroxidase-conjugated affinity-purified rabbit anti-mouse secondary antibody (Jackson Laboratories). The plates were then washed three times, developed with TMB (KPL), stopped with 1% HCl, and analyzed at 450 nm with a Dynatech MR5000ELISA plate reader.

Ad5- or Ad35-specific cellular immune responses were assessed by IFN-γ ELISPOT assays using murine splenocytes from C57/BL6 mice in response to Ad5- or Ad35-infected syngeneic BLK CL.4 stimulator cells (ATCC TIB-81; Vogels et al. 2003). BLK CL.4 cells were plated at a density of $1\times10^6$ cells per well in a 6-well plate and infected with E1-deleted Ad5-Empty or Ad35-Empty at a multiplicity of infection (moi) of $2\times10^4$ for three days. ELISPOT assays using splenocytes from immunized C57/BL6 mice were then performed as described above using $5\times10^5$ splenocytes and $1\times10^5$ Ad-infected BLK CL.4 stimulator cells per well in place of peptide antigens. For negative controls, splenocytes were incubated with uninfected BLK CL.4 cells or media alone.

Ad5- or Ad35-specific neutralizing antibody (NAb) responses were assessed by luciferase-based virus neutralization assays essentially as described (Vogels et al. 2003). A549 cells were plated at a density of $1\times10^4$ cells per well in 96-well plates. Recombinant Ad5-Luciferase or Ad35-Luciferase reporter constructs were then added at an moi of 500 with two-fold serial dilutions of serum in 200 µl reaction volumes. Following a 24-hour incubation, luciferase activity in the cells was measured using the Steady-Glo Luciferase Reagent System (Promega). 90% neutralization titers were defined as the maximum serum dilution that neutralized 90% of luciferase activity.

Statistical analyses were performed with GraphPad Prism version 2.01 (GraphPad Software, Inc., 1996). Comparisons of mean ELISPOT responses among groups of mice were performed by two-tailed t tests for two groups of animals or by analyses of variance (ANOVA) for more than two groups. Bonferroni adjustments were included when appropriate to account for multiple comparisons. In all cases, p-values of less than 0.05 were considered significant.

Comparison Between Immunogenicity of Ad5-SIVgag and Ad35-SIVgag in Naïve Mice.

Figure 14:
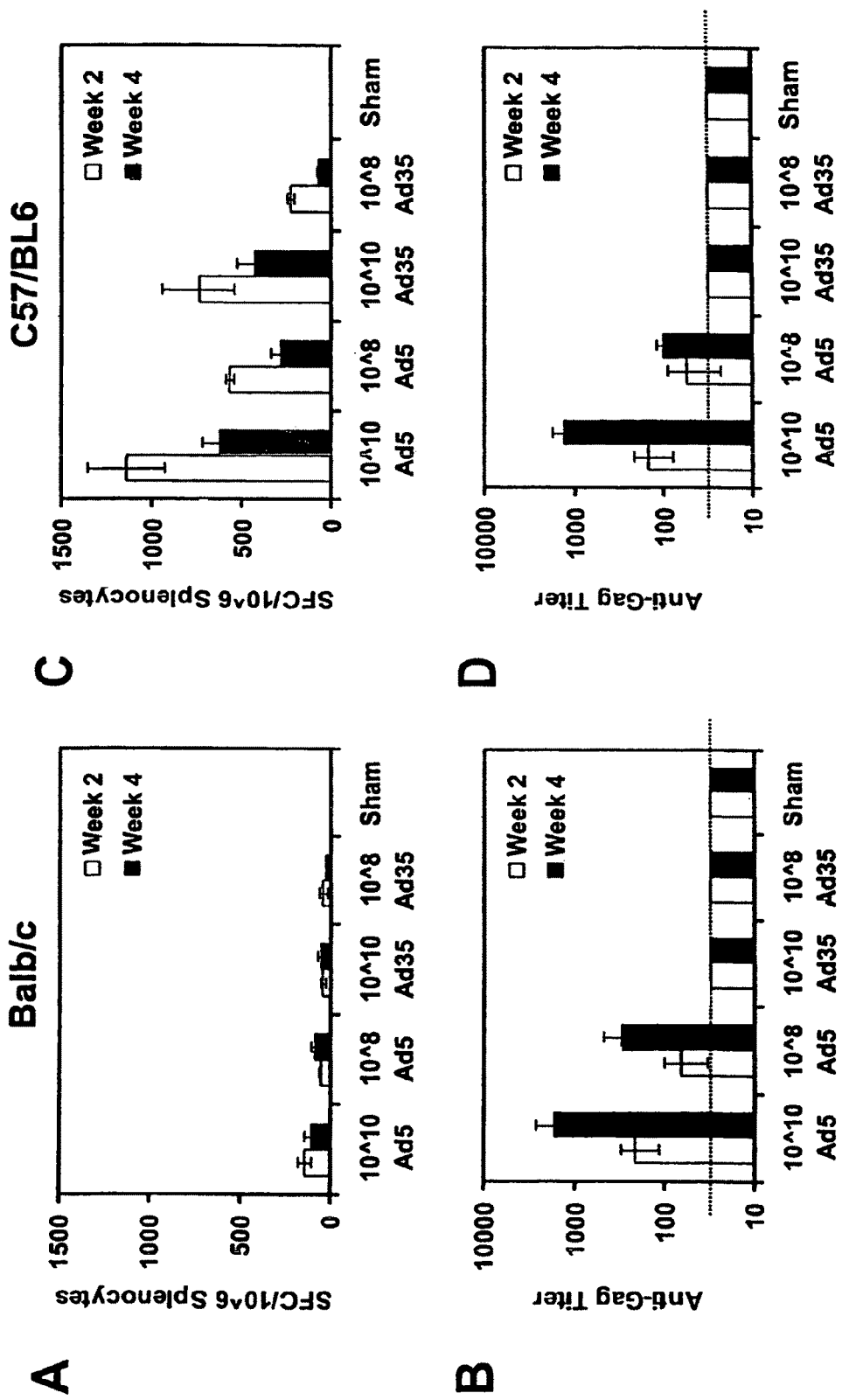
FIG. 14 depicts SIV-gag-specific cellular and humoral responses in naïve mice using Ad5-SIVgag and Ad35-SIV-gag-recombinant viruses.

Groups of Balb/c and C57/BL6 mice (N=4/group) were immunized once i.m. with $10^{10}$ vp or $10^8$ vp of each vector. Vaccine-elicited cellular immune responses were assessed by ELISPOT assays using a pool of 15 amino acid peptides overlapping by 11 amino acids covering the entire SIV Gag protein. Gag-specific ELISAs assessed vaccine-elicited humoral immune responses. As shown in FIG. 14, both Ad5-SIVgag and Ad35-SIVgag elicited only marginal Gag-specific cellular immune responses in Balb/c mice. In contrast, both vectors elicited rapid and potent cellular immune responses by two weeks following vaccination in C57/BL6 mice. The difference between the mice strains is most likely explained by restrictions of the peptide exposure capabilities of the MHC class 1 molecules in both strains. This is an antigen-specific feature. ELISPOT responses elicited by Ad35-SIVgag were consistently lower than those elicited by Ad5-SIVgag, particularly at the lower dose of $10^8$ vp. High titer anti-Gag antibody responses were elicited by Ad5-SIVgag in both Balb/c and C57/BL6 mice. In contrast, no anti-Gag antibody responses were detected following immunization with Ad35-SIVgag. Thus, Ad35-SIVgag elicited lower cellular and humoral immune responses as compared with Ad5-SIVgag in naïve mice. A reason for this finding may be the difference in receptor-binding and/or -recognition in mice as compared to humans (see below).

Mapping $D^b$-Restricted T-Lymphocyte Epitopes within SIV Gag.

Figure 15:
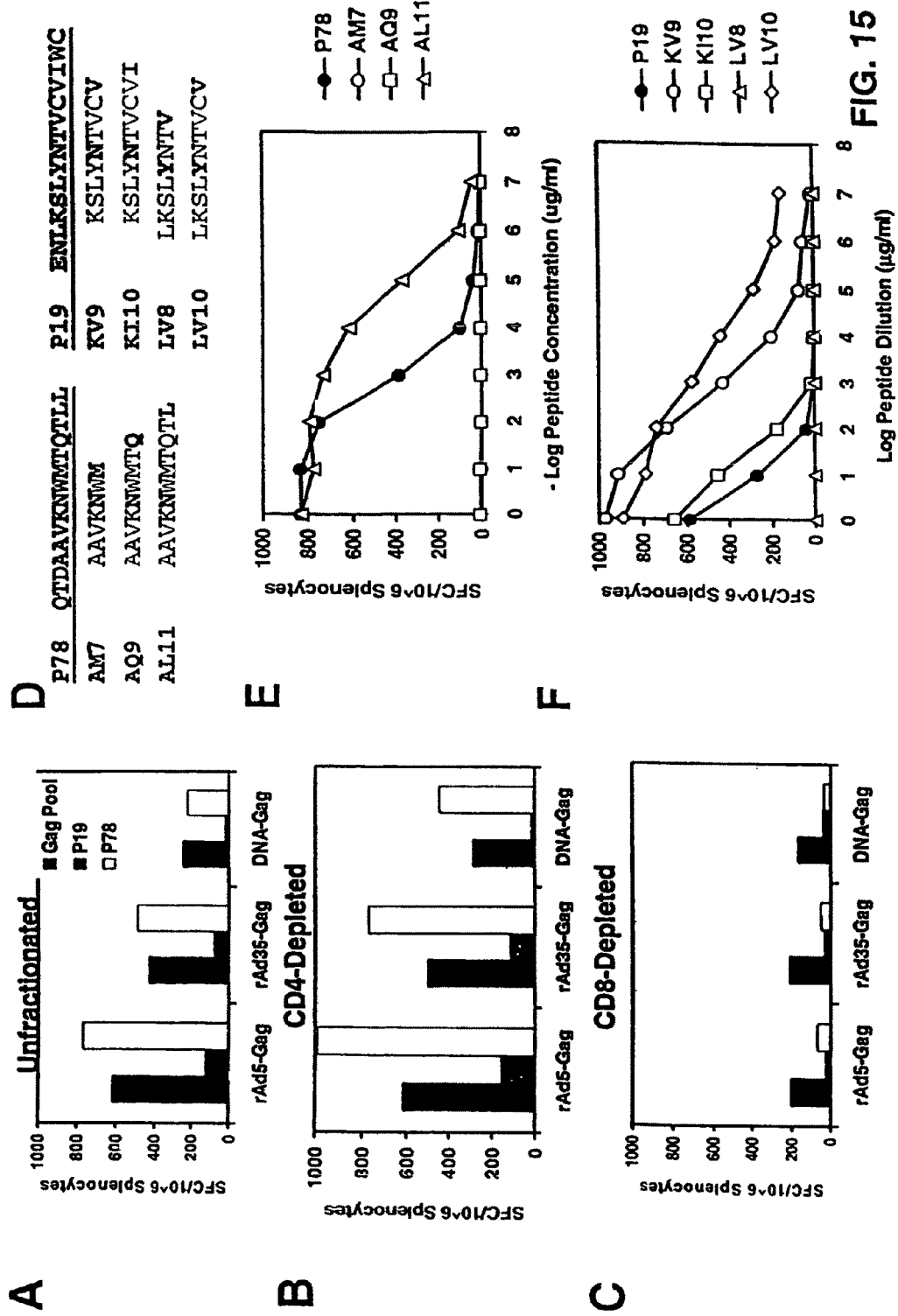
FIG. 15 shows the mapping of $D^b$-restricted and $K^b$-restricted T-lymphocyte epitopes within SIV-gag using C57/BL6 mice. P78 is SEQ ID NO:1; AM7 is SEQ ID NO:2; AQ9 is SEQ ID NO:3; AL11 is SEQ ID NO:4; P19 is SEQ ID NO:5; KV9 is SEQ ID NO:6; KI10 is SEQ ID NO:7; LV8 is SEQ ID NO:8; LV10 is SEQ ID NO:9.

The rapid emergence of high frequency Gag-specific cellular immune responses in C57/BL6 mice (FIG. 14, Panel C) suggested the presence of immunodominant $D^b$- or $K^b$-restricted CD8$^+$ T-lymphocyte epitopes. Therefore a matrix-based ELISPOT approach was utilized to identify candidate epitopes within SIV-Gag. As depicted in FIG. 15, Panels A-C, C57/BL6 mice immunized with $10^{10}$ vp recombinant Ad5, $10^{10}$ vp recombinant Ad35, or 50 µg plasmid DNA expressing SIV-Gag developed an immunodominant cellular immune response to the 15 amino acid P78 peptide (QTDAAVKN-WMTQTLL; SEQ ID NO:1) and a subdominant response to the P19 peptide (ENLKSLYNTVCVIWC; SEQ ID NO:5). ELISPOT assays utilizing splenocytes depleted of CD4$^+$ or CD8$^+$ T-lymphocytes demonstrated that both P78 and P19 were in fact CD8$^+$ T-lymphocyte epitopes.

Next, these epitopes based on the peptide-binding motifs of $D^b$ (asparagine at position 5 and hydrophobic carboxy-terminus) and $K^b$ (tyrosine at position 5 and hydrophobic carboxy-terminus) were fine-mapped. As shown in FIG. 15, Panels D-F, candidate optimal peptides were assessed at log dilutions from 1 µg/ml to 100 µg/ml in peptide-specific ELISPOT assays. A $D^b$-restricted immunodominant AL11 (AAVKN-WMTQTL; SEQ ID NO:4) epitope within P78 and a $D^b$-restricted subdominant KV9 (KSLYNTVCV; SEQ ID NO:6) epitope within P19 were identified. These CD8$^+$ T-lymphocyte epitopes elicited ELISPOT responses when utilized at concentrations of 1 pg/ml and were confirmed by functional chromium-release cytotoxicity assays using peptide-pulsed EL4 cells as well as Ltk cells transfected with $D^b$, but not Ltk cells transfected with $K^b$, as targets. The LV10 peptide was similarly investigated as a potential $K^b$-restricted epitope, but this peptide could not be confirmed in cytotoxicity assays using Ltk cells transfected with $K^b$ as targets, suggesting that its reactivity in ELISPOT assays may reflect KV9 contaminant peptide within the LV10 preparation.

Ad5-Specific and Ad35-Specific NAb Titers in Humans.

Figure 16:
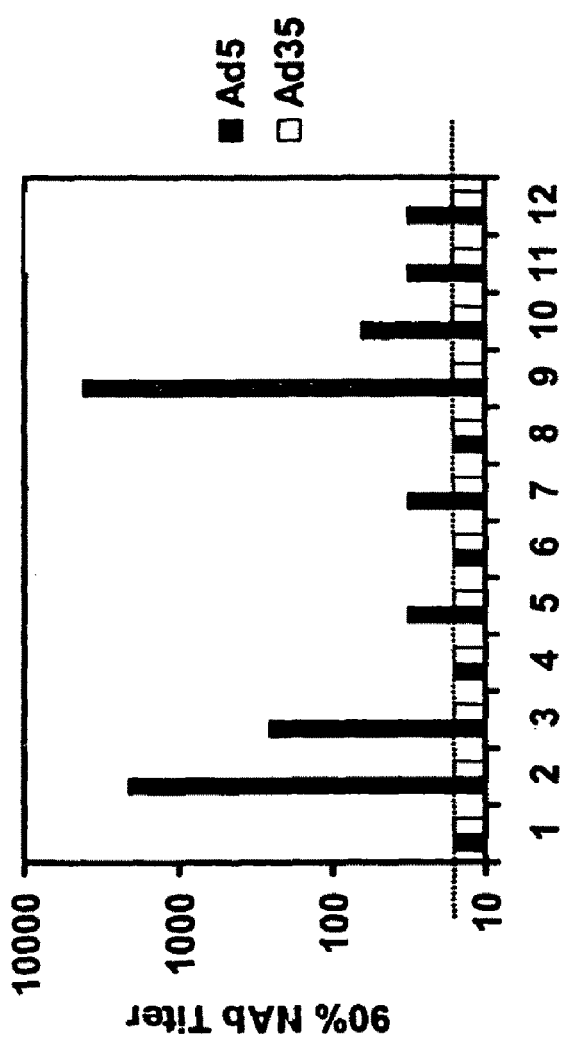
FIG. 16 shows Ad5-specific and Ad35-specific Nab titers in humans.

Next, 12 human serum samples for NAb titers to Ad5 and Ad35 were assessed. 90% NAb titers were defined as the maximal serum dilution that inhibited rAd5-Luciferase or rAd35-Luciferase infectivity of A549 cells by 90%. As shown in FIG. 16, eight of twelve samples (67%) exhibited Ad5-specific NAb titers of 32 or higher. In addition, two of twelve samples (17%) had Ad5-specific NAb titers of 2048 or higher. None of these samples had detectable Ad35-specific NAb titers (<16). These data are consistent with previous observations regarding the high seroprevalence of Ad5 and the low seroprevalence of Ad35 (Vogels et al. 2003). Positive controls were sera from mice immunized with Ad5 or Ad35.

Immunogenicity of Ad5-SIVgag and Ad35-SIVgag in Mice with Anti-Ad5 Immunity.

Figure 17:
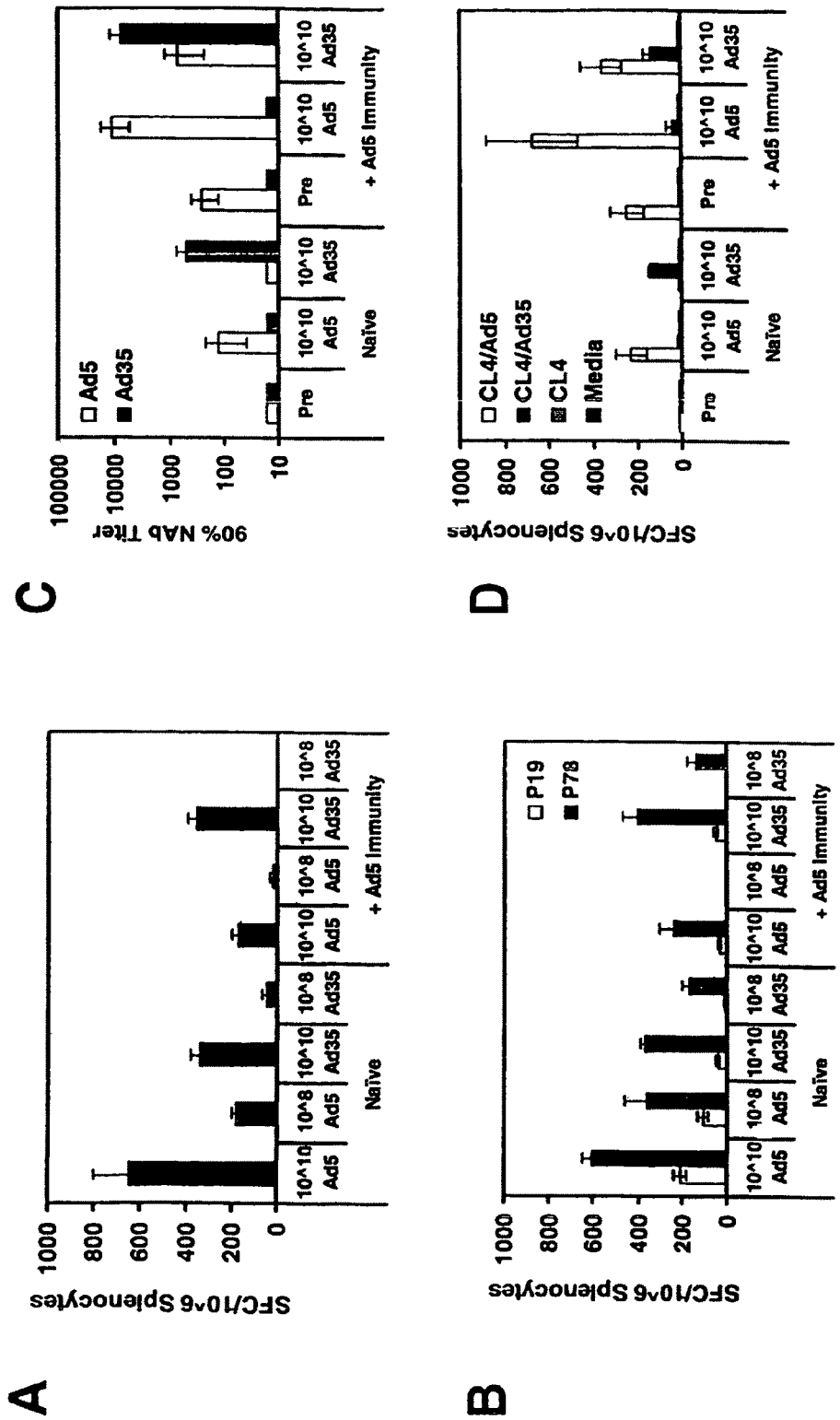
FIG. 17 depicts humoral and cellular immune responses to Ad5-SIVgag and Ad35-SIVgag in mice pre-immunized with one shot of Ad5-Empty.

The impact of anti-Ad5 immunity on cellular immune responses elicited by Ad5-SIVgag and Ad35-SIVgag was determined. To model anti-Ad5 immunity, C57/BL6 mice were pre-immunized once with $10^{10}$ vp rAd5-Empty at four weeks prior to immunization. As shown in FIG. 17, Panel C, mice pre-immunized with Ad5-Empty developed mean Ad5-specific neutralizing antibody (NAb) titers of 128 but no detectable Ad35-specific NAb titers (<16). These NAb titers were comparable with those typically found in humans (FIG. 16). Ad-specific T-lymphocyte responses in these mice were assessed by virus-specific ELISPOT assays using splenocytes stimulated with Ad5- or Ad35-infected syngeneic BLK/CL.4 cells. As shown in FIG. 17, Panel D, mice pre-immunized with Ad5-Empty developed Ad5-specific ELISPOT responses of 250 SFC/$10^6$ splenocytes but no detectable Ad35-specific ELISPOT responses (<25 SFC/$10^6$ splenocytes).

Groups of naïve mice or mice with anti-Ad5 immunity (N=4/group) were then immunized with $10^{10}$ vp or $10^8$ vp Ad5-SIVgag or Ad35-SIVgag. Four weeks following immunization, vaccine-elicited cellular immune responses were assessed by Gag pooled peptide and epitope-specific ELISPOT assays. As shown in FIG. 17, Panels A and B, Gag-specific and epitope-specific cellular immune responses elicited by $10^{10}$ vp Ad5-SIVgag were blunted by 75% in mice with anti-Ad5 immunity as compared with naïve mice. Cellular immune responses elicited by $10^8$ vp Ad5-SIVgag were completely abrogated in mice with anti-Ad5 immunity. In contrast, responses elicited by Ad35-SIVgag were not substantially reduced in mice with anti-Ad5 immunity and were higher than those elicited by Ad5-SIVgag (p<0.05 comparing pooled peptide ELISPOT responses using two-tailed t tests).

Vector-specific humoral and cellular immune responses were also assessed in these groups of mice. As shown in FIG. 17, Panel C, naïve mice immunized with Ad5-SIVgag or Ad35-SIVgag developed Ad serotype-specific NAb responses. As expected, mice pre-immunized with Ad5-Empty generated potent, anamnestic (secondary) Ad5-specific NAb responses following Ad5-SIVgag immunization. Interestingly, mice pre-immunized with Ad5-Empty also generated potent, anamnestic Ad35-specific NAb responses following Ad35-SIVgag immunization. These responses were >10-fold higher than the Ad35-specific NAb responses generated in naïve mice following the same Ad35-SIVgag immunization, suggesting that pre-immunization with Ad5-Empty may have primed for low levels of cross-reactive Ad5/Ad35 responses. As shown in FIG. 17, Panel D, naïve mice immunized with Ad5-SIVgag or Ad35-SIVgag developed Ad serotype-specific ELISPOT responses, and mice pre-immunized with Ad5-Empty generated higher Ad5-specific ELISPOT responses following Ad5-SIVgag immunization.

Figure 18:
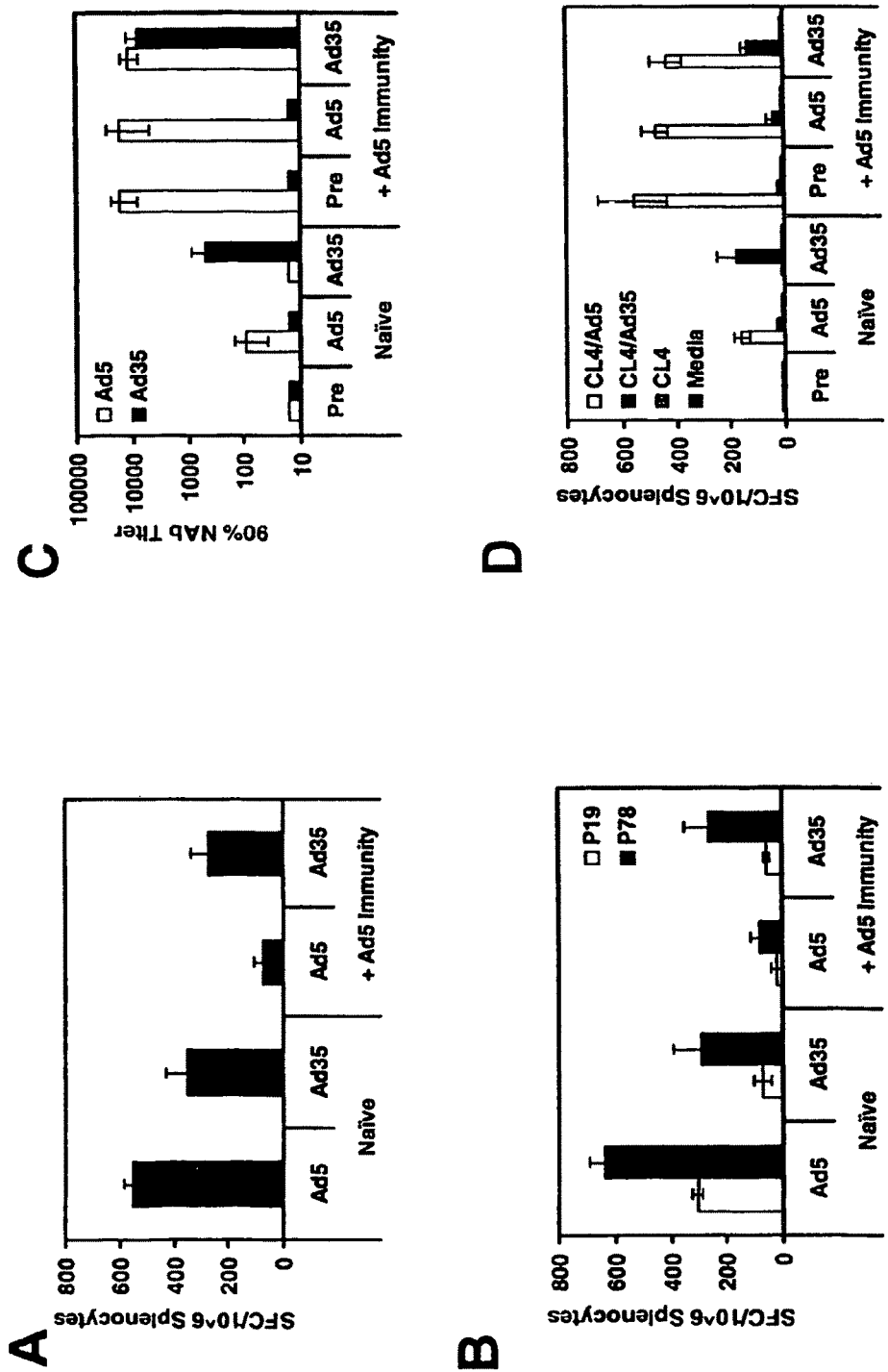
FIG. 18 depicts humoral and cellular immune responses to Ad5-SIVgag and Ad35-SIVgag in mice pre-immunized with two shots of Ad5-Empty.

Immunogenicity of Ad5-SIVgag and Ad35-SIVgag in Mice with High Levels of Anti-Ad5 Immunity Next, the ability of high levels of anti-Ad5 immunity to suppress cellular immune responses elicited by Ad5-SIVgag and Ad35-SIVgag was assessed. Mice were pre-immunized twice with $10^{10}$ vp Ad5-Empty at eight weeks and four weeks prior to immunization. As shown in FIG. 18, Panel C, these mice developed mean Ad5-specific NAb titers of 16,384 but no detectable Ad35-specific NAb titers (<16). As shown in FIG. 18, Panel D, these mice also developed high frequency Ad5-specific ELISPOT responses of 560 SFC/$10^6$ splenocytes but no detectable Ad35-specific ELISPOT responses (<25 SFC/$10^6$ splenocytes). Thus, pre-immunization of mice with two doses of Ad5-Empty generated >10-fold higher Ad5-specific NAb titers and >2-fold higher Ad5-specific ELISPOT responses as compared with pre-immunization of mice with one dose of Ad5-Empty.

Groups of naïve mice or mice with high levels of anti-Ad5 immunity (N=4/group) were then immunized with $10^{10}$ vp Ad5-SIVgag or Ad35-SIVgag. Four weeks following immunization, Gag-specific cellular immune responses were assessed. As shown in FIG. 18, Panels A and B, high levels of anti-Ad5 immunity abrogated Gag-specific and epitope-specific ELISPOT responses elicited by $10^{10}$ vp Ad5-SIVgag by >90%, whereas ELISPOT responses elicited by $10^{10}$ vp Ad35-SIVgag were at most marginally reduced. Thus, in mice with high levels of anti-Ad5 immunity, Ad35-SIVgag was substantially more immunogenic than Ad5-SIVgag (p<0.001 comparing pooled peptide and peptide-specific ELISPOT responses using two-tailed t tests). As shown in FIG. 18, Panels C and D, Ad5-specific NAb responses and Ad5-specific ELISPOT responses in mice with high levels of anti-Ad5 immunity were not further increased following Ad5-SIVgag immunization. These data suggest that the Ad5-SIVgag vaccine vector was rapidly neutralized before eliciting substantial antigen-specific or vector-specific immune responses in these mice.

Immunogenicity of Heterologous Prime/Boost Regimens in Naïve Mice.

Figure 19:
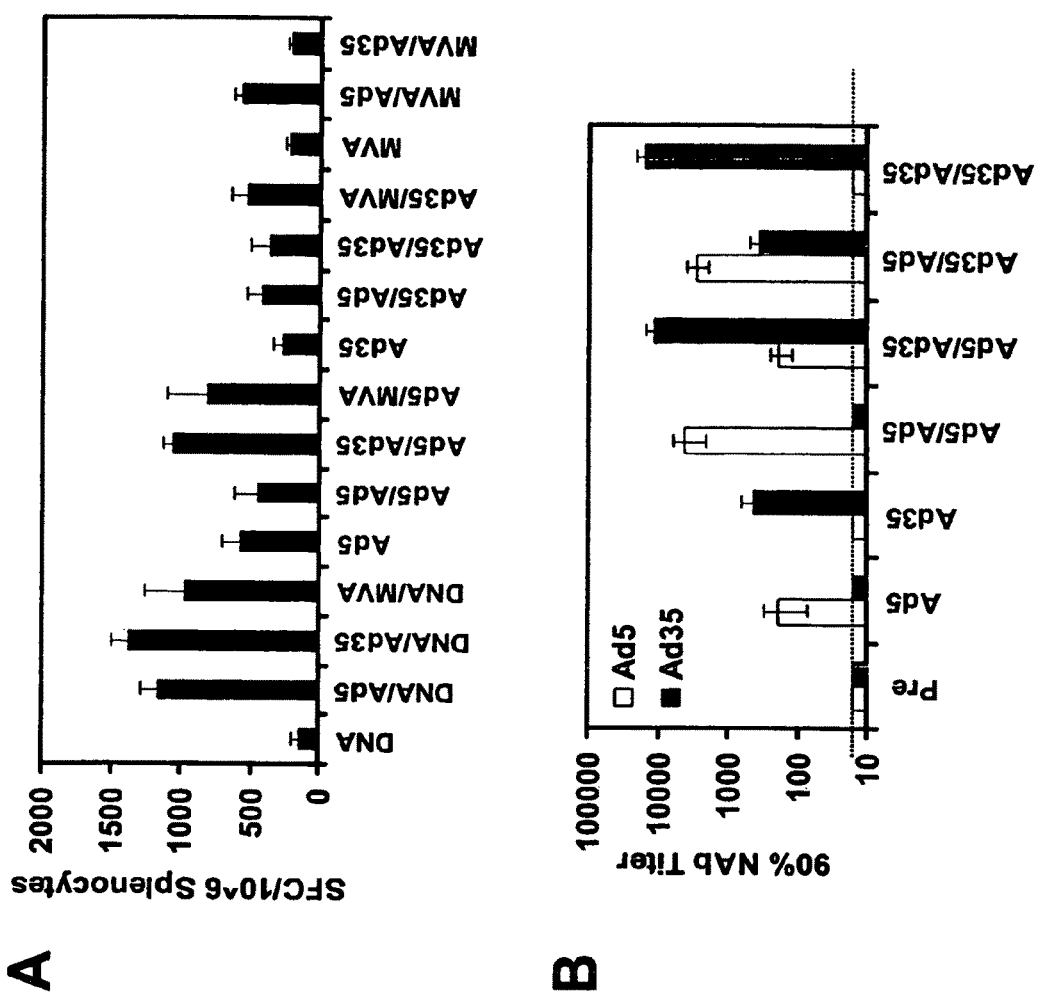
FIG. 19 shows immune responses upon several heterologous prime/boost regimens in naïve mice.

Next, the immunogenicity of several heterologous prime/boost regimens in naïve C57/BL6 mice was assessed. Groups of mice (N=4/group) were primed with either 50 pg plasmid DNA, $10^{10}$ vp recombinant Ad5, $10^{10}$ vp recombinant Ad35, or $10^8$ pfu recombinant MVA all expressing Sly-Gag. Mice were then boosted at week 4 with either $10^{10}$ vp recombinant Ad5, $10^{10}$ vp recombinant Ad35, or $10^8$ pfu recombinant MVA and sacrificed at week 8 for immunologic assays. As shown in FIG. 19, Panel A, plasmid DNA expressing SIV-Gag primed low frequency Gag-specific cellular immune responses. These responses were boosted effectively and comparably by Ad5-SIVgag, Ad35-SIVgag, and rMVA-Gag. In contrast, Ad5-SIVgag primed higher levels of Gag-specific cellular immune responses, but these responses were not significantly boosted by a second administration of Ad5-SIVgag, presumably as a result of anti-Ad5 immunity. Importantly, responses primed by Ad5-SIVgag were boosted effectively by Ad35-SIVgag. These data demonstrate that Ad35-SIVgag is efficient at boosting responses primed by DNA-Gag or Ad5-SIVgag. These data further suggest that prime/boost regimens utilizing heterologous adenovirus vectors can elicit potent immune responses comparable in magnitude to those elicited by DNA prime-viral vector boost regimens.

The Ad35-SIVgag and rMVA-Gag vectors primed moderate levels of Gag-specific cellular immune responses. Interestingly, the recombinant Ad5 prime-recombinant Ad35 boost regimen was substantially more immunogenic than the recombinant Ad35 prime-recombinant Ad5 boost regimen. Moreover, the recombinant Ad5 prime-recombinant MVA boost regimen was slightly more immunogenic than the recombinant MVA prime-recombinant Ad5 boost regimen. These results suggest that the order of vector administration may be important to achieve optimal immunogenicity. Thus, the more potent priming vector is preferably, but not necessarily, used to prime the response and the more potent boosting vector is preferably, but not necessarily, used to boost the response when two recombinant viral vectors are utilized in prime/boost regimens. It is to be understood that this effect may be antigen specific. For one application applying a certain antigen, one serotype may be the more potent prime or boost vector, while this may be different in another application applying another antigen. The invention therefore also relates to methods for addressing what vector is the more potent vector during priming or boosting, using different antigens.

As shown in FIG. 19, Panel B, mice primed with Ad5-SIVgag and boosted with Ad35-SIVgag developed >10-fold higher Ad35-specific NAbs as compared with naïve mice primed with Ad35-SIVgag. Similarly, mice primed with Ad35-SIVgag and boosted with Ad5-SIVgag developed >10-fold higher Ad5-specific NAbs as compared with naïve mice primed with Ad5-SIVgag. These data suggest that either low levels of cross-reactive NAbs (titers<16) or helper T-lymphocyte responses were primed by each Ad vector and resulted in anamnestic responses following administration of the heterologous Ad vector. In a subsequent administration it would therefore be preferred to use another vector (which is heterologous to the previous) to obtain a sufficiently high immune response. This would, for instance, be the case for vaccination situations in which several boosts are required or in cases wherein several different antigens are to be delivered over time.

Immunogenicity of Heterologous Prime/Boost Regimens in Mice with Anti-Ad5 Immunity.

Figure 20:
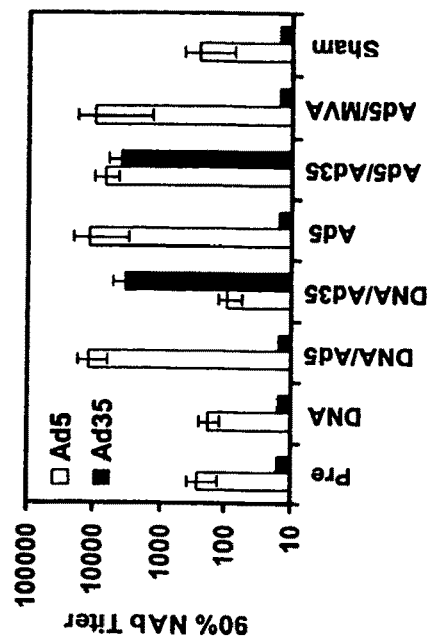
FIG. 20 shows immune responses upon several heterologous prime/boost regimens in Ad5-Empty pre-immunized mice.
Figure 20:
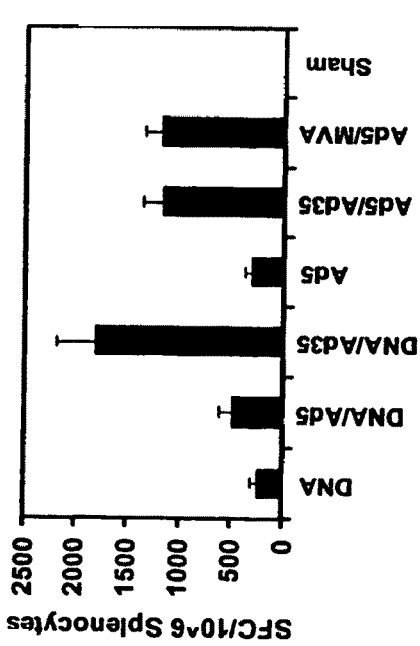
Figure 20:
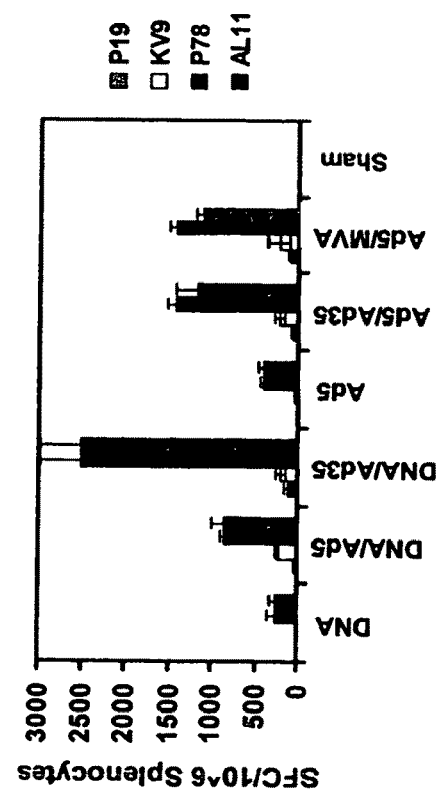

Since the majority of humans have pre-existing anti-Ad5 immunity, it is important to assess candidate heterologous prime/boost regimens in animals with anti-Ad5 immunity. Therefore, the immunogenicity of various prime/boost regimens in C57/BL6 mice that were pre-immunized once with $10^{10}$ vp rAd5-Empty at 4 weeks prior to primary immunization were determined. These mice had Ad5-specific NAb titers of 128-256 at the time of primary immunization (FIG. 20, Panel C). Groups of mice (N=4/group) were primed at week 0 with 50 µg DNA or $10^{10}$ vp recombinant Ad5 expressing SIV-Gag and then boosted at week 4 with $10^{10}$ vp recombinant Ad5, $10^{10}$ vp recombinant Ad35, or $10^8$ pfu recombinant MVA expressing SIV-Gag. Mice were sacrificed at week 8 for immunologic assays.

As shown in FIG. 20, Panels A and B, the DNA prime-recombinant Ad35 boost regimen elicited higher ELISPOT responses than the recombinant Ad5 prime-recombinant Ad35 boost or the recombinant Ad5 prime-recombinant MVA boost regimens (p<0.01) and markedly higher ELISPOT responses than the DNA prime-recombinant Ad5 boost regimen in these mice (p<0.001 comparing pooled peptide and dominant epitope-specific ELISPOT responses among groups of mice using ANOVA with Bonferroni adjustments to account for multiple comparisons). Thus, in mice with anti-Ad5 immunity, the DNA prime-recombinant Ad35 boost regimen elicited the highest frequency ELISPOT responses among these various regimens with Gag pooled peptide responses of >1500 SFC/$10^6$ splenocytes and P78- and AL11-specific responses of >2500 SFC/$10^6$ splenocytes.

Thus, it was shown that anti-Ad5 immunity markedly blunted the immunogenicity of recombinant Ad5-SIVgag. In contrast, even high levels of anti-Ad5 immunity did not substantially reduce the immunogenicity of recombinant Ad35-SIVgag in mice. In particular, in mice with anti-Ad5 NAb titers comparable with those typically found in humans, cellular immune responses elicited by Ad35-SIVgag were higher than those elicited by Ad5-SIVgag.

In naïve mice, however, Ad35-SIVgag elicited substantially lower cellular and humoral immune responses than did Ad5-SIVgag. These differences in immunogenicity are consistent with previous observations that Ad35-mediated transgene expression was several-fold lower than Ad5-mediated transgene expression in mouse muscle (Vogels et al. 2003). In addition, Ad5 interacts with the Coxsackievirus and Adenovirus Receptor (CAR) on the surface of cells with its long and flexible fiber protein. In contrast, the Ad35 fiber protein is shorter and more rigid than the Ad5 fiber, and its receptor is distinct from CAR. It was recently shown that B-group adenoviruses recognize the CD46 protein on the cell surface (Gagger et al. 2003; Segerman et al. 2003). As a result, Ad5 and Ad35 (and Ad11, being a subgroup B virus) exhibit different cellular tropisms. For example, Ad35 infects human dendritic cells, smooth muscle cells, and synoviocytes more efficiently than Ad5. Moreover, Ad5 and Ad35 have different intracellular trafficking pathways and escape endosomes at different stages (Shayakhmetov et al. 2003). These differences in attachment and intracellular trafficking likely account in part for the differences in immunogenicity observed with Ad5-SIVgag and Ad35-SIVgag. At present, it is not clear why the differences in Gag-specific humoral immune responses between Ad5-SIVgag and Ad35-SIVgag were far more striking than the differences in Gag-specific cellular immune responses between these two vectors. It is possible that a higher threshold of antigen is needed to generate antibody responses as compared with T-lymphocyte responses in this system.

The heterologous prime/boost experiments demonstrated potent Ad-specific NAb responses in mice following priming and boosting with heterologous Ad vectors. It is possible that cross-reactive NAb responses below the limit of detection (titers<16) were elicited by each Ad vector and were recalled following administration of the heterologous Ad vector. An alternate possibility is that cross-reactive helper T-lymphocyte responses were elicited by each Ad vector and led to robust NAb responses following administration of the heterologous Ad vector. Regardless, the immunogenicity of Ad35-SIVgag was not substantially blunted in mice with anti-Ad5 immunity despite the rapid evolution of high titer anti-Ad35 NAb responses. These data show that anti-vector NAb responses present at the time of immunization may be more important than those that develop following immunization in determining their potential suppressive effects on vaccine immunogenicity.

The heterologous prime/boost studies further demonstrated that recombinant Ad35 vectors efficiently boosted cellular immune responses primed by plasmid DNA and Ad5 vaccines in mice both with and without anti-Ad5 immunity. In mice with anti-Ad5 immunity, the DNA prime-recombinant Ad35 boost regimen was significantly more immunogenic than the DNA prime-recombinant Ad5 boost, recombinant Ad5 prime-recombinant MVA boost, and recombinant Ad5 prime-recombinant Ad35 boost regimens. It appears that Ad35-SIVgag may be less effective than Ad5-SIVgag at priming immune responses in mice but at least as effective at boosting immune responses, although it cannot be excluded that this "better boost" effect is antigen specific.

Example 10

Construction of a Plasmid-Based System to Generate Ad11 Recombinant Viruses

In order to construct the Ad11 adapter plasmid pAdApt11 the necessary Ad11 sequences were PCR-amplified from wild-type Ad11 viral DNA and combined with the expression cassette containing a promoter, polylinker and poly-adenylation signal taken from pAdAptp35IP1 (described in detail in WO 00/70071).

Wild-type Ad11 viruses (RIVM, The Netherlands) were propagated on PER.C6™ cells and DNA was isolated from 300 µl of purified virus (1.5×$10^{12}$ vp/ml) using phenol/chloroform extraction, ethanol precipitation and ethanol (70%) wash procedures known to the person skilled in the art and generally as described in WO 00/70071. The entire Ad11 sequence was obtained from a shotgun library generated from randomly sheared DNA that was blunt-ended with the Klenow enzyme (New England Biolabs). Blunt-ended fragments (1-3 kb in length) were purified from a low-melting point agarose gel. The shotgun library was constructed after ligation of these purified size fractionated DNA fragments into the SmaI site of the pUC19 cloning vector and amplified on competent XL1-Blue MRF' bacteria (Stratagene). After library amplification transformed bacteria were plated on LB-agar plates containing ampicillin, X-gal and IPTG. An array of clones in 96-well plates covering the Ad11 genome 8 times was used to generate the entire sequence. DNA sequencing was performed using Big Dye Terminator chemistry, with AmpliTaq FS DNA polymerase using Puc forward or reverse sequencing primers. Reactions were analyzed on ABI3100 and ABI3700 sequencers. In total there were 687 sequencing reads obtained which were assembled into the final contig using the Phred-Phrap software package. The resulting contig covers the entire Ad11 genome, being 34,794 base pairs in length (WO 02/53759).

The Ad11 left Inverted Terminal Repeat (left ITR or lITR) and packaging sequence (corresponding to wt-Ad11 sequence 1-464) was PCR-amplified from wt-Ad11 DNA template using primers 35F1 and 35R2 (for reference to the sequence of these primers, see WO 00/70071). PCR-amplification introduces a PacI site at the 5' end and an AvrII site at the 3' end of the amplified product. For the amplification reactions Pwo DNA polymerase enzyme (Roche) was used according to manufacturer's instructions, DMSO was added to a final concentration of 3% and 0.6 mM of both forward and reverse primers were used. The amplification program was set as follows: 2 minutes at 94° C., 30 cycles of 30 seconds at 94° C., 30 seconds at 60° C. and 1 minute at 72° C.; followed by one final extension of 8 minutes at 68° C. The amplified DNA product was purified using the Qiaquick PCR purification kit (Qiagen) according to the manufacturer's instructions. The fragment was then cloned into the SrfI site of the pre-digested pPCRScript.Amp(SK+) cloning vector (Stratagene) and grown in DH5α-competent (max. efficiency) bacteria (Invitrogen). The resulting plasmid was named pPCRScript.lITR and was analyzed by restriction enzyme digestions using BssHII, AccI and AvrII/PacI. One positive clone, with the insert in the correct orientation, was selected, grown and digested sequentially with AvrII and SacII. The clones with correct orientation yielded a 439 bp fragment after digestion with AccI. The double-digested vector was recovered from agarose gel and purified using the Qiaquick gel extraction kit (Qiagen) and used in further cloning procedures (see below).

Next, the part of the Ad11 genome downstream of the E1 region and corresponding to wt-Ad11 sequence 3400 to 4670, was generated. This region harbors the sequence mediating homologous recombination and generation of recombinant Ad11 viruses when used with a cosmid carrying the Ad11 genome from the pIX coding region towards the right ITR (rITR). The entire 1.27 kb fragment was generated with PCR-amplification using wt-Ad11 DNA as a template using the primers 35F3 and 35R4 (for reference to the sequence of the applied primers, see WO 00/70071). PCR-amplification introduces a BglII site at the 5' end and a PacI site at the 3' end of the sequence. PCR procedures were performed as described above. The amplified DNA product was purified using the Qiaquick PCR purification kit. The purified fragment was then cloned into the SrfI site of pre-digested and gel-purified pPCRScript.Amp(SK+) cloning vector, using methods known to persons skilled in the art. The resulting plasmid was named pPCRScript.overlap and further digested with BglII and SacII-restriction enzymes. The resulting 1.27 kb BglII-SacII fragment that represents the overlapping Ad11 DNA was isolated over agarose gel.

Figure 21:
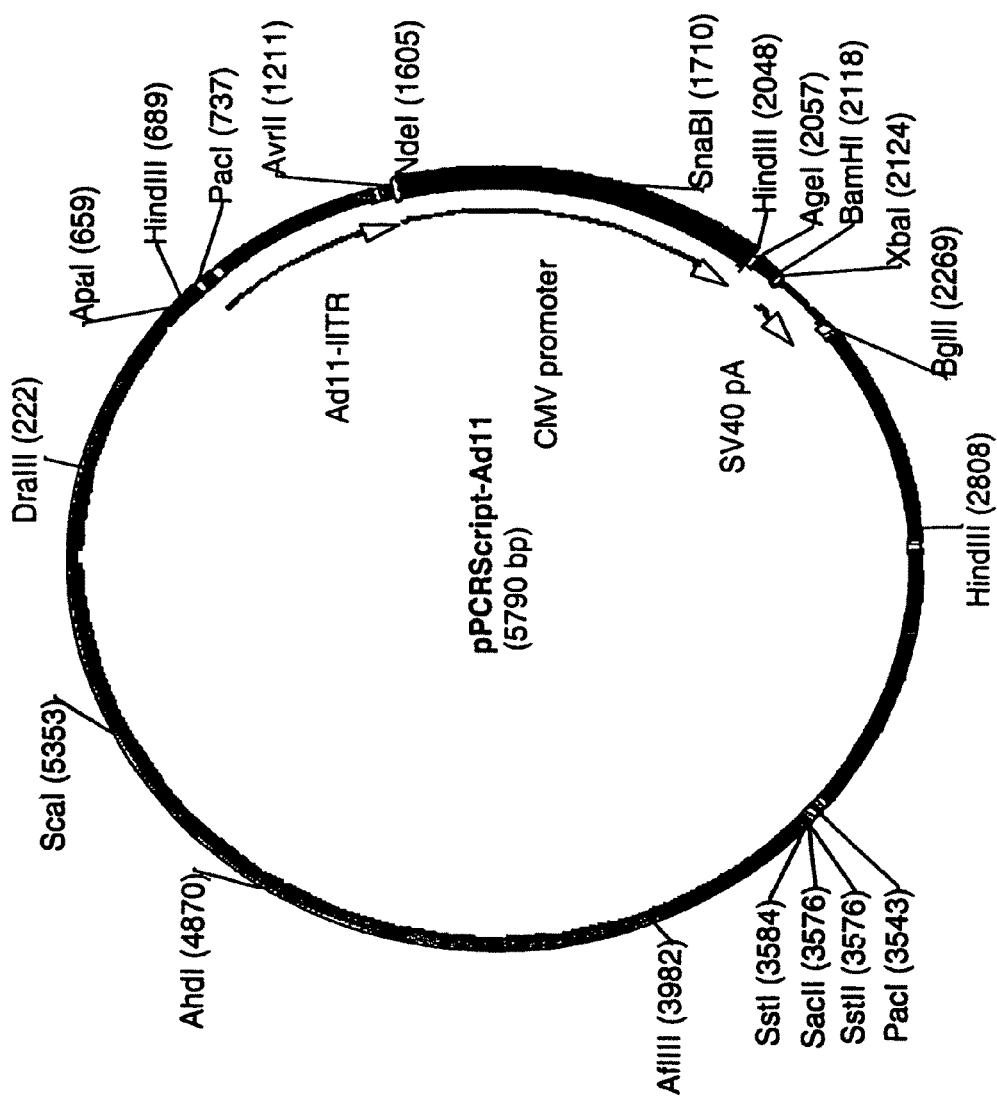
FIG. 21 is a map of pPCRScript-Ad11.
Figure 22:
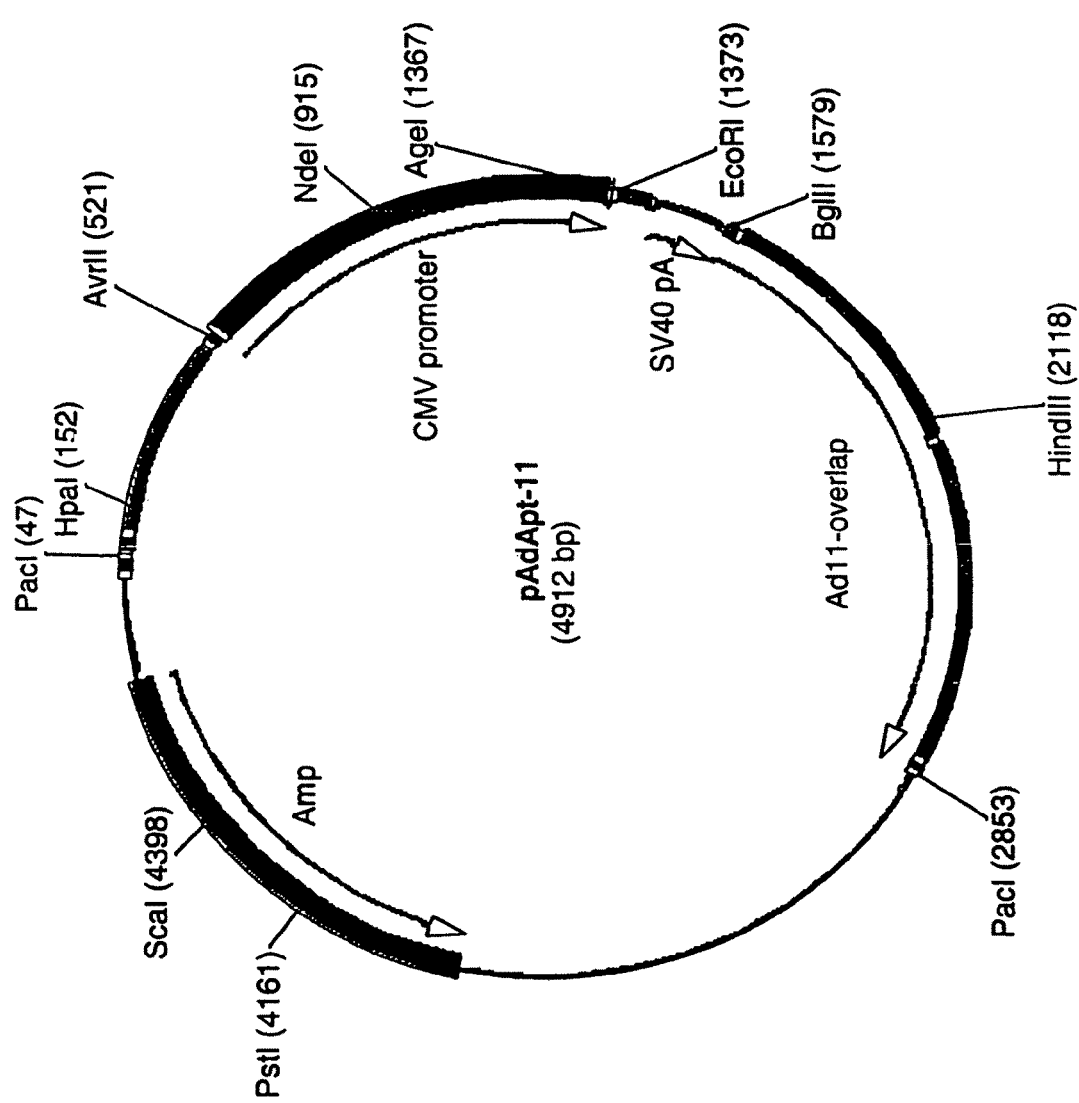
FIG. 22 is a map of pAdApt11.

Plasmid pAdApt35IP1 (WO 00/70071) was digested with A AvrII and BglII-restriction enzymes. The 4.34 kb AvrII-BglII fragment, representing the CMV promoter, the multiple cloning site and the SV40 poly(A) tail was isolated and purified. This AvrII-BglII fragment, the isolated BglII-SacII fragment from pPCRScript.overlap (see above) and the isolated SacII-AvrII-digested pPCRScript.lITR (see above) were cloned together in a three-point ligation procedure using methods known to persons skilled in the art. The resulting plasmid was named pPCRScript-Ad11 (FIG. 21). Subsequently, pPCRScript-Ad11 was digested with PacI-restriction enzyme and the resulting 2.8 kb fragment was isolated over agarose gel. This 2.8 kb fragment was then cloned into the vector fragment of pAdApt35IP1 following digestion with PacI and isolation from gel. The resulting vector was named pAdApt11 (FIG. 22).

Figure 23:
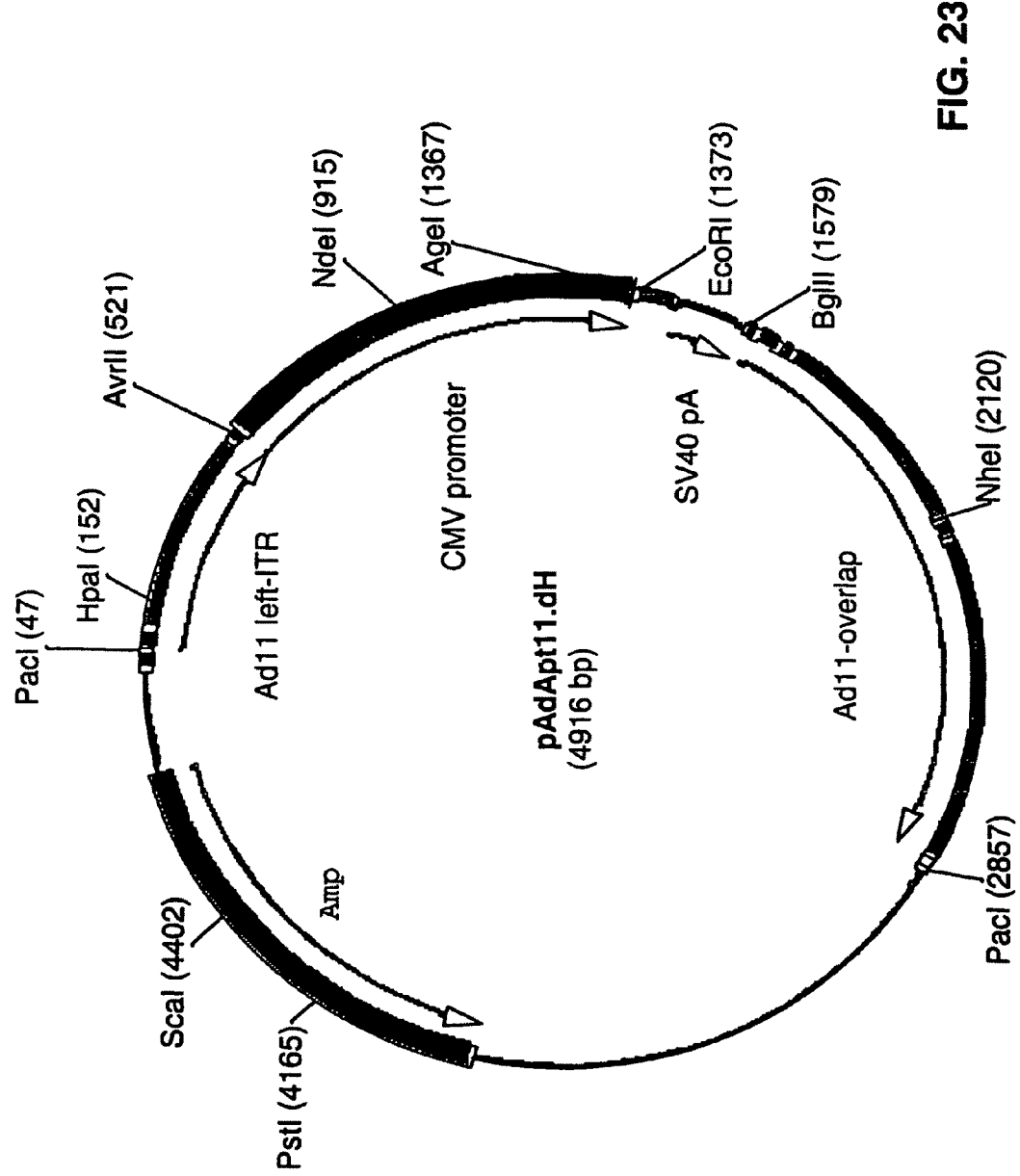
FIG. 23 is a map of pAdApt11.dH.

Except for a HindIII site in the polylinker, pAdApt11 contained a second HindIII site at position 3934 (calculated from the Ad11 genome) in the overlap sequence that is required for homologous recombination. In order to have a unique HindIII site in the polylinker, the second HindIII site was eliminated. For this, pAdApt11 was partially digested with HindIII. The protruding HindIII ends were filled-in with dNTPs using Klenow enzyme. The partially digested vector was re-circularized and transformed into DH5α-competent bacteria. The resulting construct was named pAdApt11.dH (FIG. 23).

The part of the Ad11 genome downstream of the E1 region, lacking the pIX promoter and corresponding to wt-Ad11 sequence 3466 to 4668, was also generated. This region of the genome also harbors an overlapping part of the Ad11 genome for proper homologous recombination and generation of recombinant Ad11 viruses when used with a cosmid carrying the rest of the Ad11 genome towards the right ITR (rITR). First, a 1.2 kb fragment (nucleotides 3465-4668) was PCR-amplified using pAdApt11.dH as a template with the primers pIX11Fmfe (5'-CTC TCT CAA TTG TCT GTC TTG CAG CTG TCA TG-3' SEQ ID NO:10) and 35R4 (for reference to the sequence of the 35R4 primer, see WO 00/70071). The PCR-amplification introduces an MfeI site at the 5' end of the fragment. An ApaI site is internally present in the amplified product.

For the PCR 2.5 U of Pfu DNA polymerase enzyme (Promega) was used, while the following PCR program was applied: 3 minutes at 94° C.; 5 cycles of 30 seconds at 94° C., 30 seconds at 56° C. and 2 minutes at 72° C.; 25 cycles of 30 seconds at 94° C., 30 seconds at 60° C., 2 minutes at 72° C.; and one single final extension of 8 minutes at 68° C. The amplified DNA product was purified using the Qiaquick PCR purification kit (Qiagen) and fragments were then cloned into the SrfI site of a pre-digested pPCRScript.Amp(SK+) cloning vector. The resulting plasmid was designated pPCRScript.overlap.dPr and subsequently digested with MfeI and ApaI. This MfeI-ApaI-restriction fragment was recovered from an agarose gel.

Figure 24:
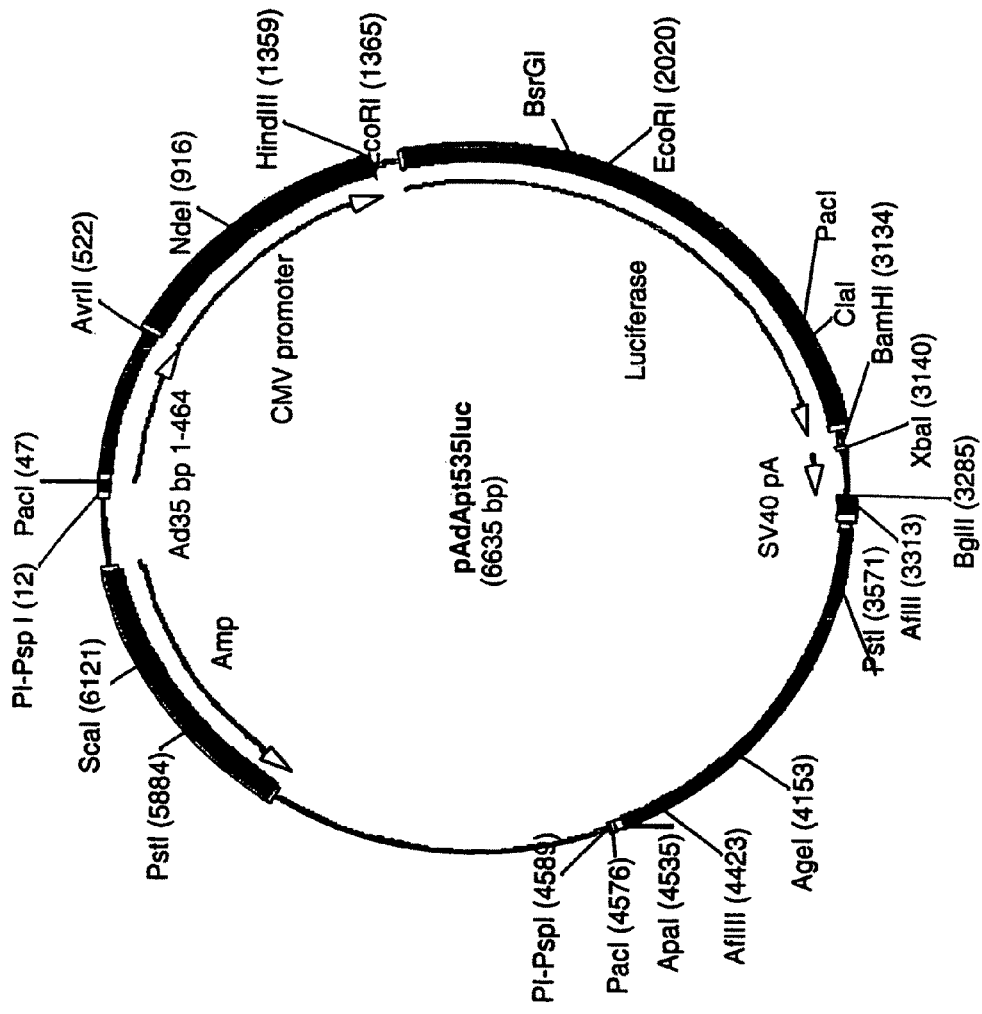
FIG. 24 is a map of pAdApt535.Luc.
Figure 25:
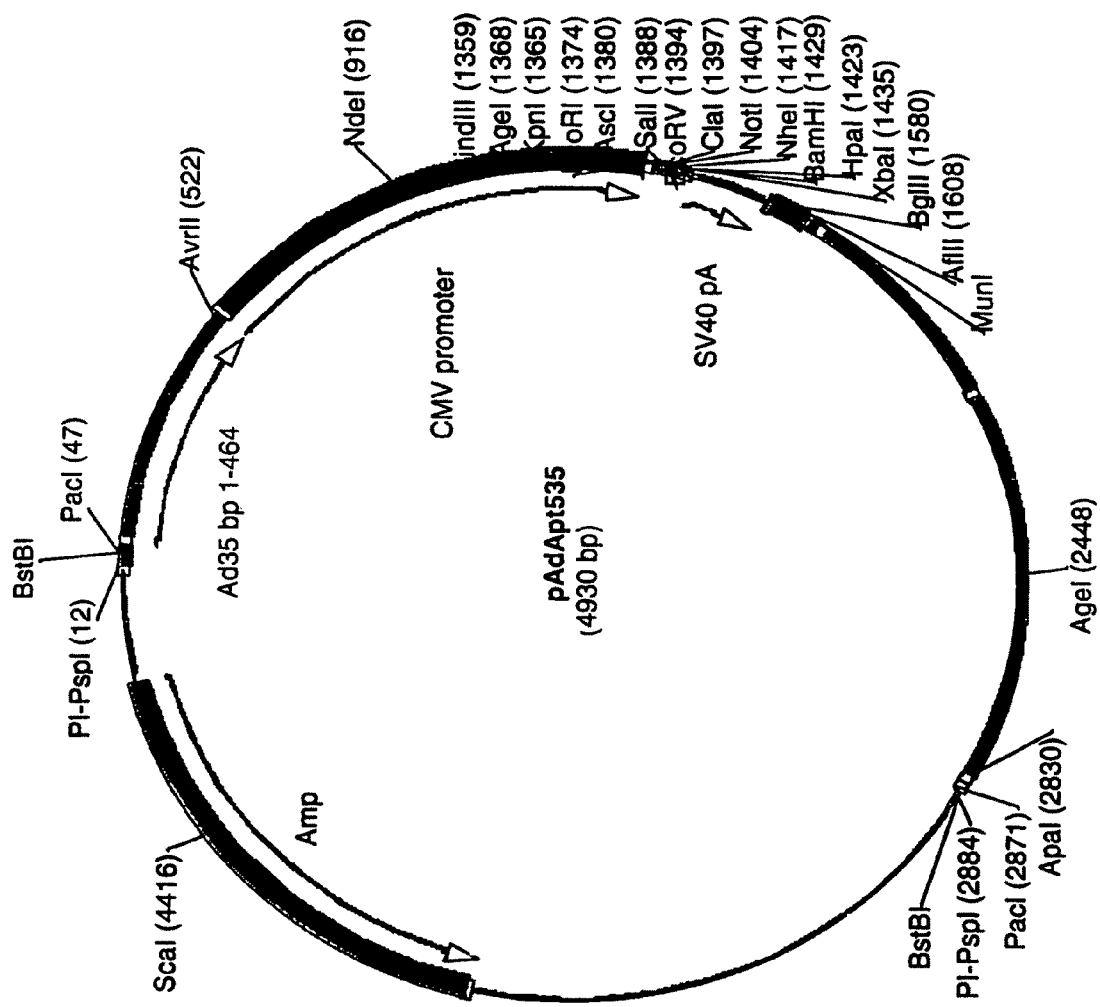
FIG. 25 is a map of pAdApt535.

A first 101 bp PCR fragment containing the Ad5 pIX promoter (nucleotides 1509-1610 was generated with the primers SV40 for (5'-CAA TGT ATC TTA TCA TGT CTA G-3' SEQ ID NO:11) and pIX5Rmfe (5'-CTC TCT CAA TTG CAG ATA CAA AAC TAC ATA AGA CC-3' SEQ ID NO:12). The reaction was done with Pwo DNA polymerase according to manufacturer's instructions but with 3% DMSO in the final mix. pAdApt (see WO 00/70071) was used as a template. The program was set as follows: 2 minutes at 94° C.; 30 cycles of: 30 seconds at 94° C., 30 seconds at 52° C. and 30 seconds at 72° C.; followed by 8 minutes at 72° C. The resulting PCR fragment contains the 3' end of the SV40 polyadenylation signal from pAdApt and the Ad5-pIX promoter region as present in GenBank Accession number M73260 from nucleotide 3511 to nucleotide 3586 and an MfeI site at the 3' end. A second PCR fragment was generated as described above but with primers pIX35Fmfe (5'-CTC TCT CAA TTG TCT GTC TTG CAG CTG TCA TG-3' SEQ ID NO:13) and 35R4. pAdApt35IP1 was used as a template, the annealing was set at 58° C. for 30 seconds and the elongation of the PCR program was set at 72° C. for 90 seconds. This PCR procedure amplifies Ad35 sequences from nucleotide 3467 to nucleotide 4669 (sequence numbering as in WO 00/70071) and adds an MfeI site to the 5' end. Both PCR fragments were digested with MfeI and purified using the Qiagen PCR purification kit (Qiagen). Approximate equimolar amounts of the two fragments were used in a ligation reaction. Following an incubation of two hours with ligase enzyme in the correct buffers, at room temperature, the mixture was loaded on an agarose gel and the DNA fragments of 1.4 kb length were isolated with the Geneclean II kit (BIO101, Inc). The purified DNA was used in a PCR amplification reaction with primers SV40 and 35R4. The PCR was done as described above with an annealing temperature of 52° C. and an elongation time of 90 seconds. The resulting product was isolated from gel using the Qiagen gel extraction kit and digested with AgeI and BglII. The resulting 0.86 kb fragment containing the complete 100 nucleotide pIX promoter form Ad5, the MfeI site and the pIX ORF (fragment MfeI-AgeI, including the ATG start site) from Ad35, but without a poly(A) sequence, was isolated from gel using the Geneclean II kit.

pAdApt35.Luc (described in WO 00/70071) was also digested with BglII and AgeI and the 5.8 kb vector was isolated from gel using the Geneclean II kit as described above. This fragment was ligated with the isolated 0.86 kb BglII-AgeI fragment containing the Ad5-Ad35 chimeric pIX promoter, to result in a plasmid named pAdApt535.Luc (FIG. 24).

pAdApt535.Luc was subsequently digested with BglII and ApaI and the 1.2 kb insert was purified from gel. pAdApt35IP1 was also digested with BglII and ApaI and the 3.6-kb vector fragment was isolated as above. Ligation of the 1.2 kb BglII-ApaI insert from pAdApt535.Luc and the 3.6 kb BglII-ApaI-digested vector resulted in pAdApt535 (FIG. 25). Thus, pAdApt535 is an Ad35 adapter plasmid containing part of the Ad5-pIX promoter sequence but is otherwise identical to Ad35 adapter plasmid pAdApt35IP1 (see WO 00/70071). pAdApt535 was then digested with MfeI and ApaI. The digested vector was recovered from an agarose gel using Geneclean II.

Figure 26:
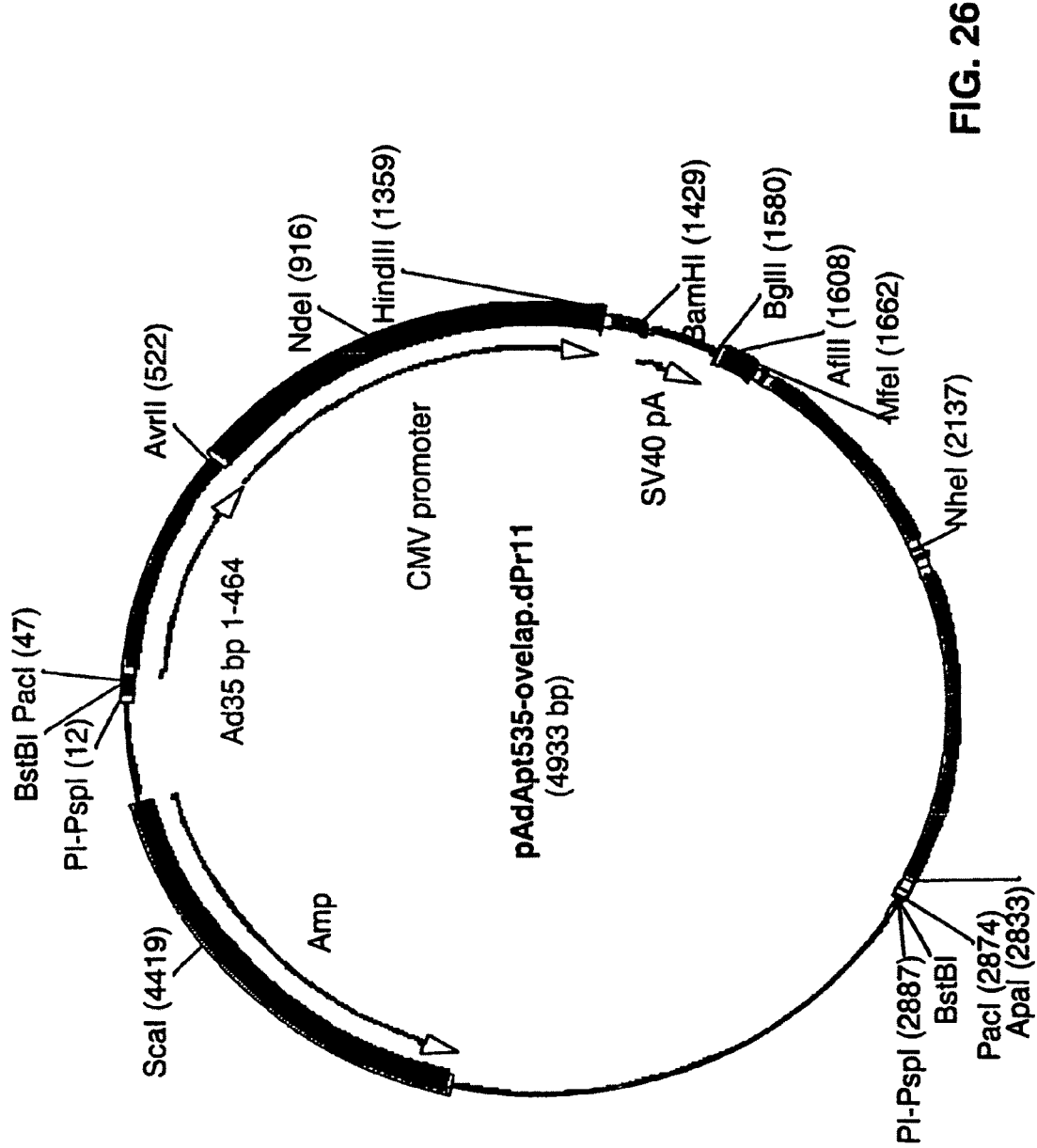
FIG. 26 is a map of pAdApt535.overlap.dPr11.

The MfeI-ApaI fragment of pPCRScript.overlap.dPr (described above) was cloned into an MfeI-ApaI-digested pAdApt535 vector (see above), using general molecular biology methodology. The resulting vector was named pAdApt535.Overlap.dPr11 (FIG. 26). This vector contains the left ITR of Ad35, an expression cassette and contains the Ad11 overlap region lacking the original Ad11 pIX promoter. The pIX promoter from Ad11 has been exchanged for the Ad5-pIX promoter. The reason for constructing such plasmid was that it served as an in-between construct through which part of the Ad11 overlap (containing the Ad5-pIX promoter: the EcoNI-BglII fragment) was used to generate pAdApt511. The whole overlap (ApaI-BglII fragment) was used to generate pAdApt511.dH (see below).

pAdApt535.Overlap.dPr11 was digested with ApaI and gel-purified. Linear vector DNA was then digested with BglII. The insert (1253 bp) was gel-purified. Another digestion was performed on the same plasmid with EcoNI and BglII generating a 389 bp insert which was also gel-purified.

Figure 27:
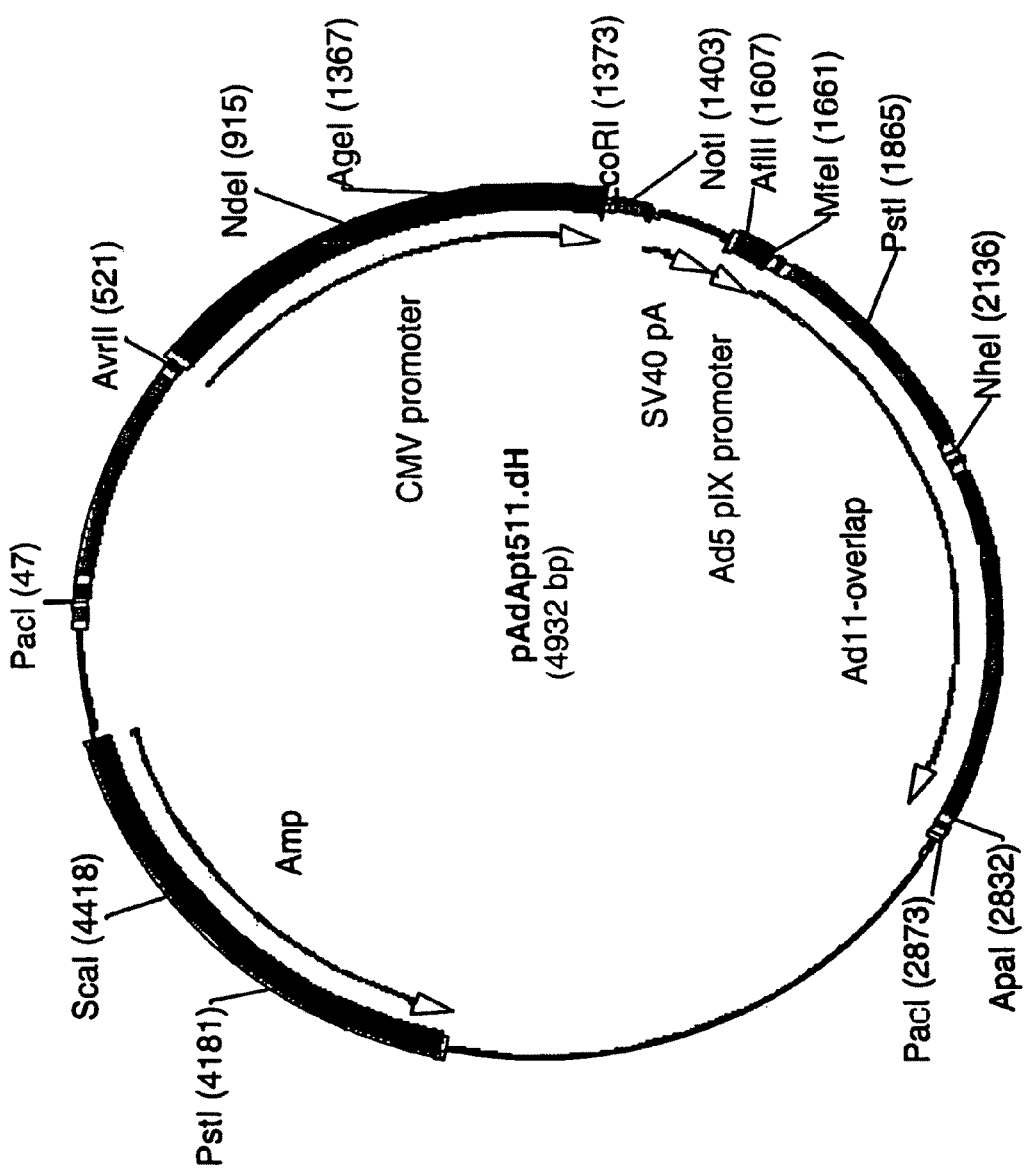
FIG. 27 is a map of pAdApt511.dH.
Figure 28:
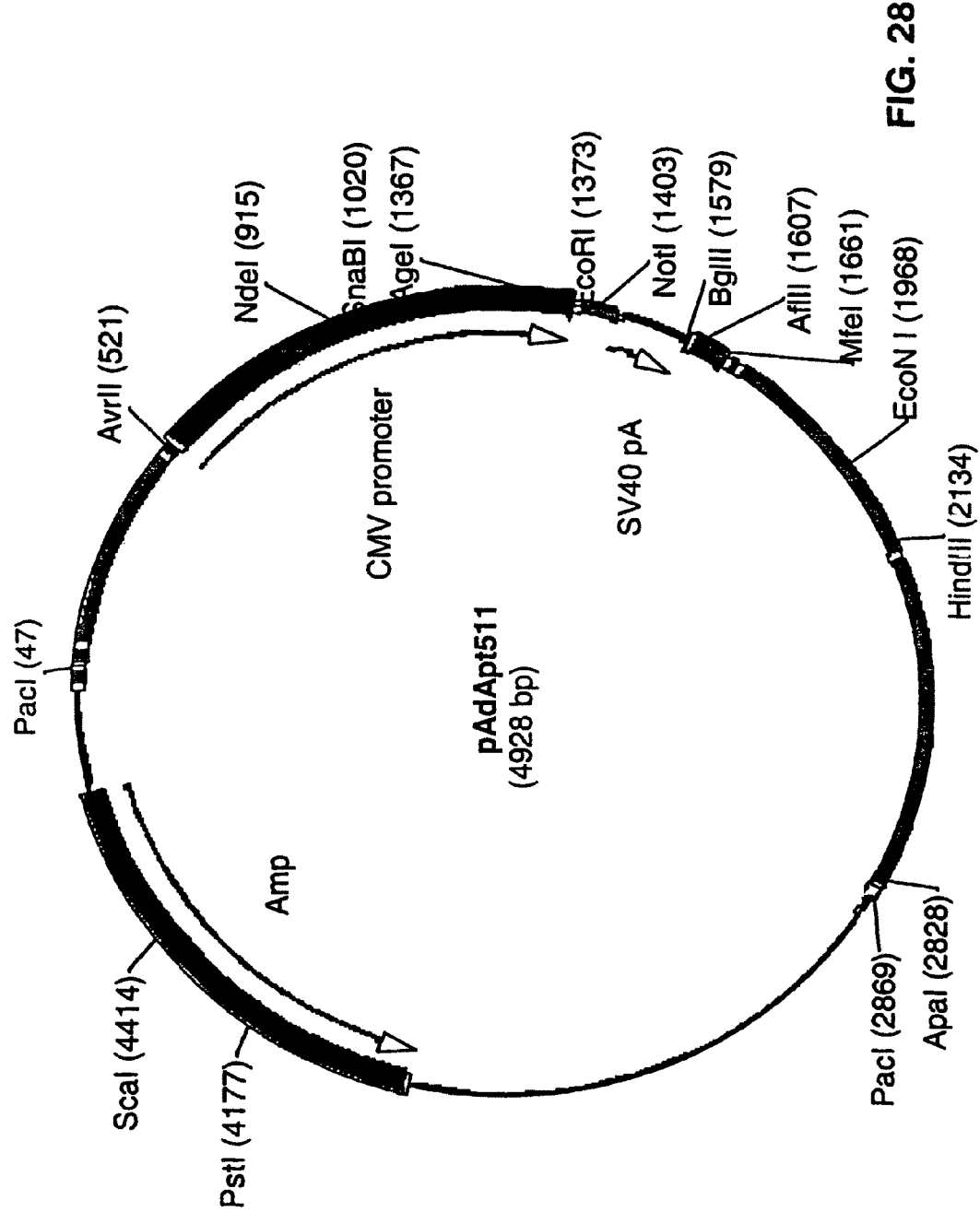
FIG. 28 is a map of pAdApt511.

Plasmid pAdApt11.dH was digested with ApaI-BglII, and another aliquot of the same plasmid was digested with EcoNI-BglII. The ApaI-BglII insert (1249 bp) from pAdApt535-overlap.dPr11 was ligated into the ApaI-BglII-digested pAdApt11.dH vector resulting in pAdApt511.dH (FIG. 27), while the EcoNI and BglII insert (389 bp) from pAdApt535-overlap.dPr was cloned into the EcoNI and BglII-digested pAdApt11 vector resulting in pAdApt511 (FIG. 28).

Generation of Ad11-Based Cosmid Clones

To obtain the Ad11 sequences corresponding to positions 3400 to 6770 of the Ad11 genome, a PCR amplification was carried out using Pwo DNA polymerase and wt-Ad11 DNA as a template with primers 35F5 and 35R6 (for reference to the primer sequences, see WO 00/70071). This PCR-amplification introduces a NotI site at the 5' end of the amplified product. The amplification program was set as follows: 2 minutes at 94° C.; 30 cycles of: 30 seconds at 94° C., 30 seconds at 65° C., 1 minute 45 seconds at 72° C.; 8 minutes at 68° C. The amplified DNA product was purified using the Qiaquick PCR purification kit (Qiagen). This 3.3 kb fragment was then cloned into an SrfI-digested pPCRScript.Amp (SK+). The resulting plasmid was named pPCRScript.pIX and contains the pIX gene and promoter of Ad11. Next, the plasmid was digested with NotI and NdeI. This NotI-NdeI-restriction fragment was gel-purified.

To generate a fragment containing the Ad11 genomic sequences from nucleotide 33095 to 34794 (including the right ITR), another PCR amplification was performed using Pwo DNA polymerase and wt-Ad11 DNA as a template and with 35F7 and 35R8 primers (for reference to the sequence of the primers, see WO 00/70071). This PCR-amplification introduces a NotI site at the 3' end of the amplified product. The amplification program was set as follows: 3 minutes at 94° C.; 5 cycles of: 30 seconds at 94° C., 45 seconds at 40° C., 2 minutes 45 seconds at 72° C.; 25 cycles of: 30 seconds at 94° C., 30 seconds at 60° C. and 2 minutes 45 seconds at 72° C.; 8 minutes at 68° C. The amplified DNA product (1.7 kb) was purified using the Qiaquick PCR purification kit and cloned into an SrfI-digested pPCRScript.Amp(SK+), resulting in a plasmid named pPCRScript.rITR. This plasmid was subsequently digested with NotI and NdeI, resulting in a 1.7 kb fragment that was recovered from an agarose gel using Geneclean II.

Figure 29:
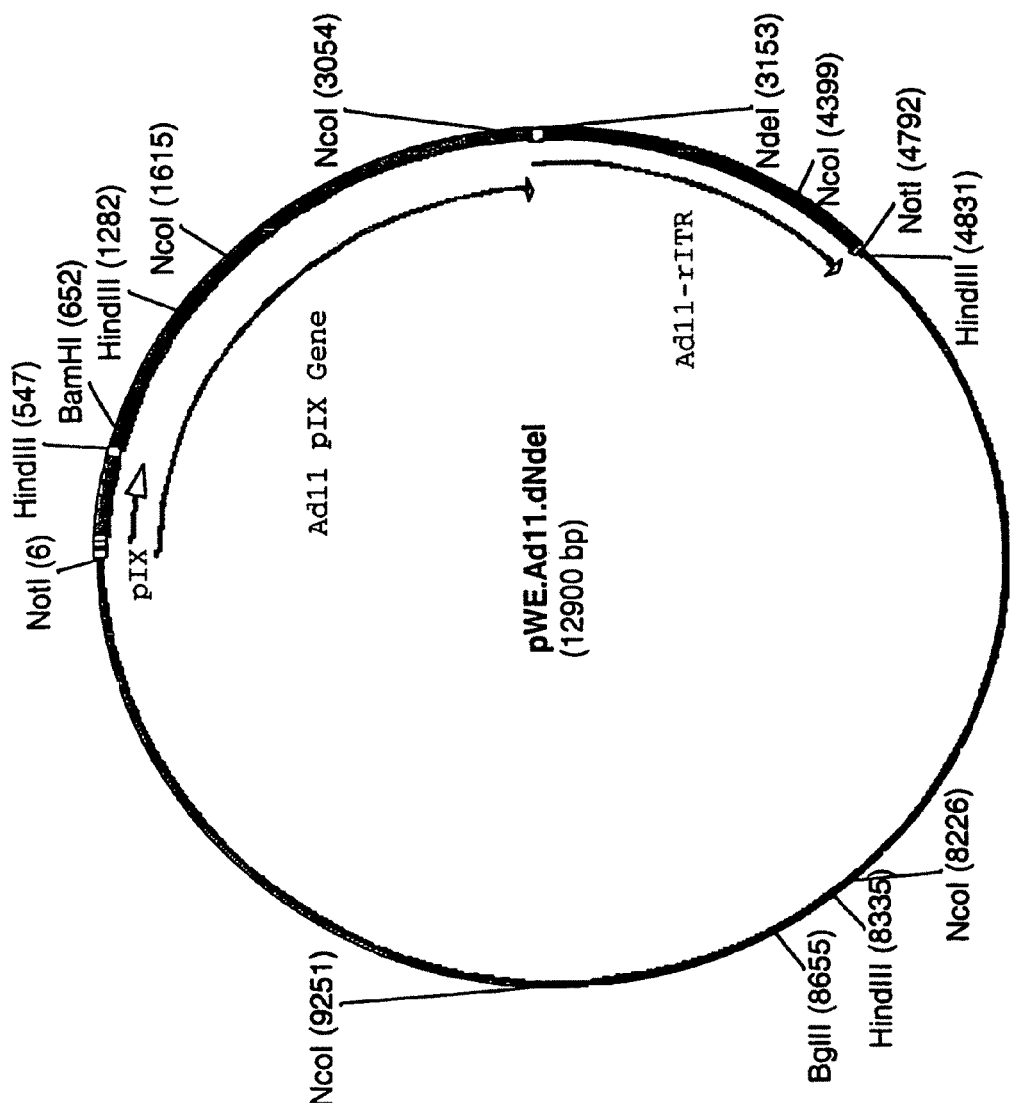
FIG. 29 is a map of pWE.Ad11.dNdeI.

To generate a vector containing the pIX promoter region of Ad11 as well as the rITR of Ad11, first cosmid vector pWE15 (Clontech Laboratories, Inc.) was digested with NotI, dephosphorylated using Calf Intestinal Phosphatase (New England Biolabs) and purified from gel using Geneclean II. Then, the NotI-NdeI fragment from pPCRScript.pIX and the NotI-NdeI fragment from pPCRScript.rITR were simultaneously ligated in a three-point ligation procedure into the NotI-digested cosmid pWE15, using methods generally applied by persons skilled in the art. The ligation mixture was transformed into STBL2-competent bacterial cells. After restriction analyses with NcoI and NdeI/HindIII-restriction enzymes, it turned out that there were no vectors having the insert in the correct orientation, but in contrast the insert was present in the antisense orientation (rITR-pIX). To obtain a construct containing the insert in the desired orientation, the NotI fragment NotI-rITR-pIX-NotI was cut from the wrong-orientation vector, purified over gel and cloned into a fresh pWE15 vector digested with NotI. Restriction analyses on DNA mini-preparations (Qiaprep spin miniprep kit) with HindIII yielded constructs that harbored inserts in the correct orientation (NotI-pIX-rITR-NotI). The resulting vector was named pWE.Ad11.dNdeI (FIG. 29), wherein dNdeI refers to the deletion of the 26.6 kb NdeI fragment, not to the NdeI site.

Sequences starting just downstream of the Ad11 pIX promoter region were PCR-amplified with pfu polymerase. The region that is amplified here corresponds to nucleotide 3480 to 4658. Two separate templates were used: pWE.Ad11.dNdeI FIG. 29) and pAdApt11.dH (FIG. 23). Both templates were used in amplifications using the same primer pair: Ad11pIXcos(2) (5'-CTG CTG GAC GTC GCG GCC GCG TCA TGA GTG GAA ACG CTT C-3' SEQ ID NO:14) and 35R3 (for reference to the sequence of 35R3, see WO 00/70071). PCR introduced an AatII site at the 5' site of the fragment while an AgeI site was internally present within the sequence. The amplification program was set as follows: 3 minutes at 94° C.; 5 cycles of: 30 seconds at 94° C., 30 seconds at 56° C., 2 minutes at 72° C.; 25 cycles of: 30 seconds at 94° C., 30 seconds at 60° C., 2 minutes at 72° C.; 8 minutes at 68° C. The amplified DNA products (1.2 kb) were purified using the Qiaquick PCR purification kit. Both the 1.2 kb fragment obtained after PCR on pWE.Ad11.dNdeI as well as the 1.2 kb fragment obtained after PCR on pAdApt.11.dH, were cloned separately into SrfI-digested pPCRScript.Amp(SK+). The resulting plasmids were named pPCRScript.pIX.dPr and pPCRScript.pIX.dH.dPr, respectively. Both constructs were digested with AatII and AgeI. The AatII-AgeI-restriction fragments represent a part of the pIX-ORF start with the ATG at position 3483, to position 4658. The fragments just start downstream of the pIX promoter and have the AgeI-restriction site at position 4245. The AatII-restriction site is incorporated at the 5' end of the sense primer and after AatII/AgeI digestion, a 762 bp fragment is generated. Both fragments were gel-purified.

Figure 30:
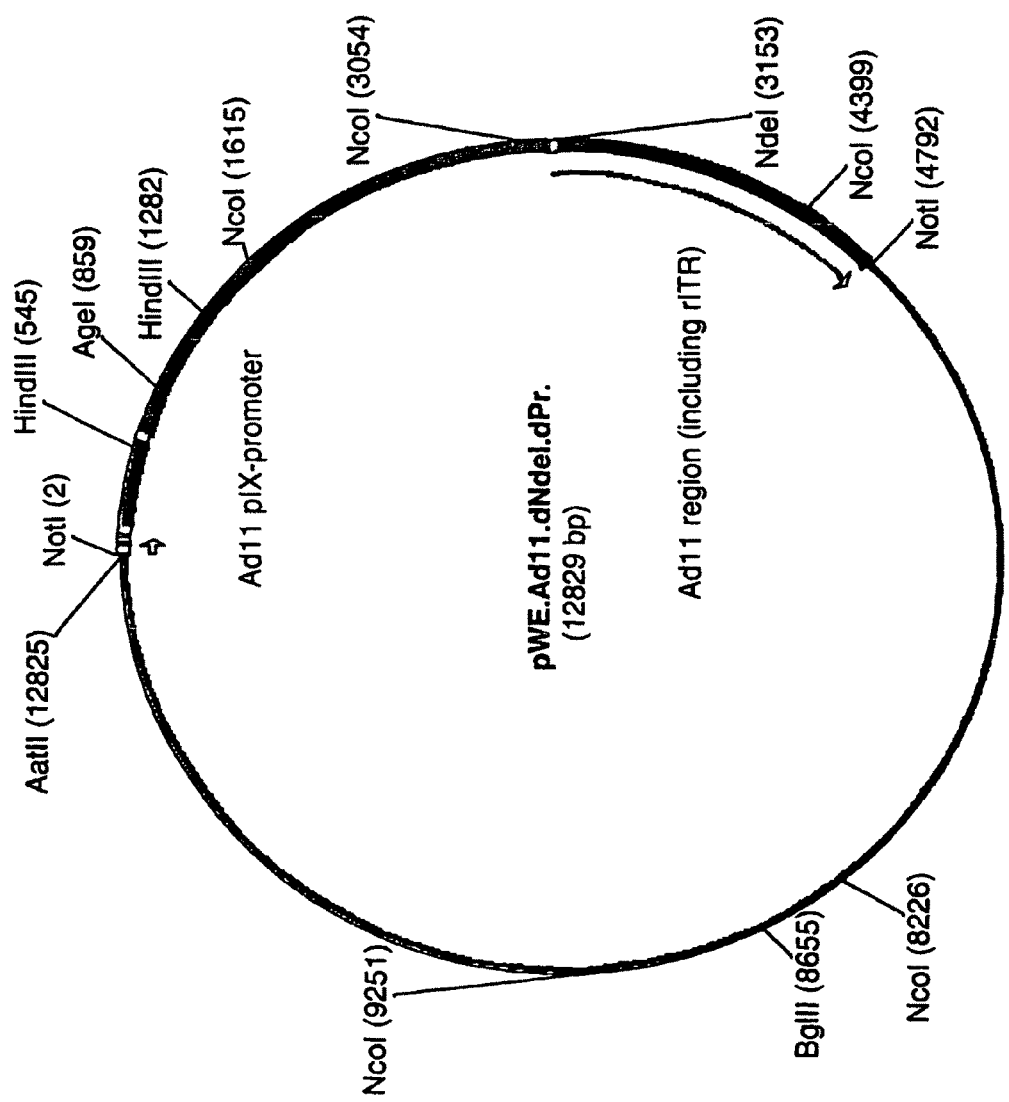
FIG. 30 is a map of pWE.Ad11.dNdeI.dPr.
Figure 31:
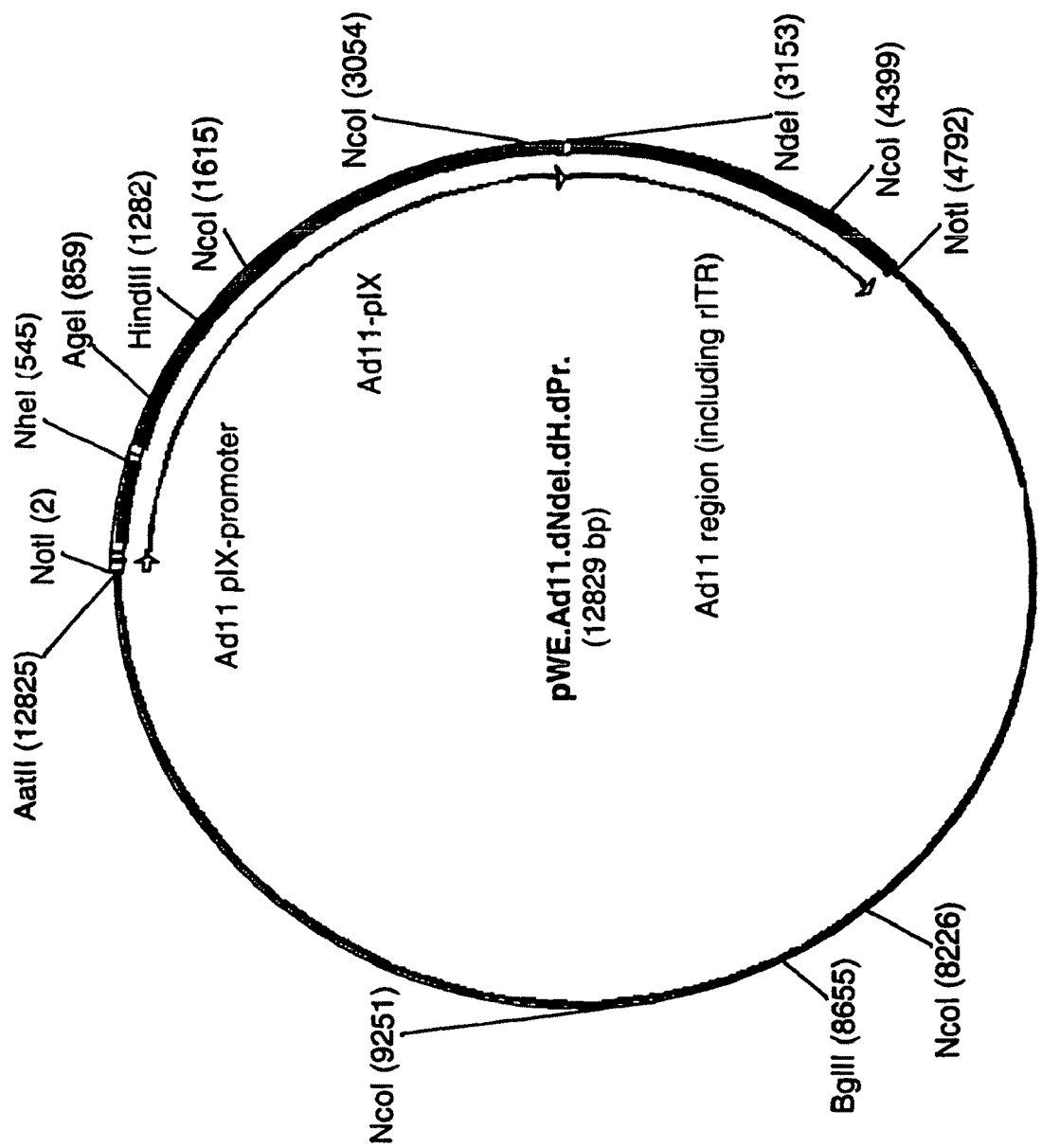
FIG. 31 is a map of pWE.Ad11.dNdeI.dH.dPr.

The vector pWE.Ad11.dNdeI was digested with AatII and AgeI and gel-purified. Subsequently, the AatII-AgeI fragment from pPCRScript.pIX.dPr was cloned into the AatII-AgeI-digested pWE.Ad11.dNdeI vector resulting in pWE.Ad11.dNde.dPr (FIG. 30). Moreover, the AatII-AgeI fragment from pPCRScript.pIX.dH.dPr was also cloned into AatII-AgeI-digested pWE.Ad11.dNdeI, which resulted in pWE.Ad11.dNdeI.dH.dPr (FIG. 31). pWE.Ad11.dNdeI.dPR and pWE.Ad11.dNdeI.dH.dPr are constructs that have the same sequences as pWE.Ad11.dNdeI but lack the pIX promoter region. The reason for taking this out is the following. In Ad35 it seems that there is an increase in transgene stability if the Ad5 pIX promoter is used instead of the original Ad35 pIX promoter (see co-pending application PCT/NL02/00281). Since Ad11 is closely related to Ad35 based on amino acid and nucleotide homology, it was reasoned that the pIX promoter from Ad5 would also be beneficial to the transgene if Ad11 would be used as a backbone. For this, also Ad11 constructs were generated harboring the pIX promoter from Ad5. It is not desirable to have the pIX promoter in the overlap between the adapter plasmid and the cosmid when homologous recombination is applied in for instance eukaryotic cells during complementation and generation of the virus. Whenever one changes something in the pIX promoter of the adapter, one would be obliged to make the same change in the cosmid vector in order to maintain the sequence homology and to provide proper homologous recombination. Thus, it is more efficient if the promoter region is not part of the overlap, and only present in the adapter plasmid (plasmids are easier to handle than cosmids). This is the reason that the Ad11 pIX promoter is removed from the cosmid.

In pWE.Ad11.dNdeI.dPr, the original HindIII site is still present at position 3934 located in the pIX region of Ad11. This site has been changed into a NheI site in pWE.Ad11.dNdeI.dH.dPr.

Both cosmid vectors pWE.Ad11.dNdeI.dPr and pWE.Ad11.dNdeI.dH.dPr were digested with NdeI and gel-purified. DNA was isolated from wild-type Ad11 viral particles and digested with NdeI-yielding fragments of 1.63 kb, 6.54 kb and 26.63 kb, respectively. The largest NdeI fragment (26.63 kb) was purified from low-melting point agarose gel (1%) using agarose enzyme (Roche) according to the manufacturer's instructions. This fragment was ligated into both the NdeI-digested cosmid vectors (see above) and packaged using the λ packaging extracts (Stratagene) according to the manufacturer's protocol. After infection into STLB-2 bacteria, colonies were grown on plates and analyzed for the presence of the complete insert. Recombinant clones were analyzed by restriction enzyme digestion with NheI, HindIII, ScaI, ApaLI, BamHI and HpaI. The two cosmids that were generated after inserting the 26.6 kb (Ad11-NdeI) fragment in pWE.Ad11.dNdeI.dPr and pWE.Ad11.dNdeI.dH.dPr were named pWE.Ad11 COSMID and pWE.Ad11.dH COSMID, respectively.

Example 11

Validation of a Quantitative Adenovirus Neutralization Assay, Based on Luciferase-Transgene Detection Currently, different assays are being used to determine anti-adenovirus-neutralizing activity. As input virus either wild-type adenovirus (wt-Ad) or recombinant replication deficient Ad5 is used. With wt-Ad, cell lines that support replication are needed. The read-out is usually performed microscopically by scoring the adenovirus-mediated cytopathic effect (CPE) or automated by staining for cell viability. The results from such an "Adenovirus Replication Inhibition Assay" (ARIA) are highly dependent on the timing of read-out but usually take between four to eight days. In another assay, replication deficient Ad virus is used and inhibition of transgene expression is taken as a parameter for antiviral-neutralizing activity. For such an "Adenovirus Transgene Expression Inhibition Assay" (ATEIA), recombinant adenoviruses carrying the LacZ, GFP or luciferase encoding genes as reporter can principally be used. This wide range of available assays, none of which is validated, renders published results of different studies difficult to interpret and compare, and thus shows a need for standardization.

Here, a head-to-head comparison of different protocols used to date to determine anti-Ad5-neutralizing activity is described. Based on accuracy, robustness, simplicity, and sensitivity, a neutralization assay based on recombinant Ad5-carrying luciferase is proposed as read-out inhibition of luciferase transgene expression.

Human Sera and IgG

Serum samples were derived from healthy adult volunteers in Belgium. The samples were screened for antibodies present against wt-Ad as described in Pauwels et al. (1988). Samples from 18 Ad5-seropositive donors were pooled and samples from five Ad5-seronegative were pooled. As a positive control, the "National Institute for Biological Standards and Controls (NIBSC, UK) second international standard anti-measles serum, human and second international standard anti-poliovirus serum, types 1, 2, and 3" was used. IgG was purified from human serum pools with the use of Mab Trap Kit according to the manufacturer's protocol (Amersham Pharmacia Biotech).

Cells and Viruses

A549 human lung carcinoma cells were grown in Dulbecco's modified Eagle's medium (DMEM) supplemented with 10% fetal bovine serum (FBS) and 1% penicillin/streptomycin. Adenoviral vectors used were wt-Ad5, Ad5.Luc, Ad35.Luc, Ad5.GFP, Ad5.LacZ. Briefly, virus produced on T175 triple-layer tissue culture flasks was purified with a two-step CsCl purification protocol. After purification, virus was aliquoted and stored at −80° C. Virus titer expressed in virus particles (vp) per milliliter was determined by HPLC.

Virus Titration

For each cell-line used the infectious titer of the virus was determined. A virus serial doubling dilution in medium ranging from 400,000 vp/cell to 5 vp/cell, was added to $1\times10^4$ cells/well in a 96-well plate (Greiner). After an incubation of 24 hours at 37° C. and 10% $CO_2$, the medium was aspirated, and 100 μl PBS followed by 100 μl Steady-Glo Luciferase Assay System Reagent (Promega) was added to each well. After an incubation of 15 minutes at room temperature, 100 μl of each well was transferred to a Black and White isoplate (Perkin Elmer) and luminescence counts measured on the 1450 Microbeta Trilux. The amount of vp/cells corresponding to upper values within the linear range of luciferase activity is used for further experiments (500 vp/cell for Ad5 and Ad35 on A549 cells).

Adenovirus Neutralization Assay

Sera were heat inactivated at 56° C. for 60 minutes, before a serial doubling dilution was performed in a 96-well tissue culture plate. The dilutions covered the range from 12.5 μl to 6 nl serum in a volume of 50 μl DMEM (eventually resulting in dilutions from 1/16 to 1/32,768 in an end volume of 200 μl). No serum was added to the negative controls, which resulted in the maximum luciferase activity. This value is used to calculate the 90% and 50% neutralization values. To every well, 50 μl of virus solution was added with a multiplicity of infection (MOI) that was determined by the virus titration. A cell suspension was made of $1\times10^5$ A549 cells/ml and 100 μl was added to every well. Plates were incubated for 24 hours at 37° C. and 10% $CO_2$ before read-out.

Neutralization Assay Read-Outs

The replication rate of wild-type adenovirus (using PER.C6 cells) was scored by measuring cell viability and by using an MTT staining, as described previously (Pauwels et al. 1988). The read-out for adenoviruses carrying luciferase is described above. For experiments using adenoviruses carrying GFP, medium was aspirated, 100 μl PBS added and fluorescent levels were measured in a fluorescent plate reader (Fluoroskan Ascent FL Labsystems) using wavelengths of 485 nm (excitation) and 527 nm (emission). For experiments using adenoviruses carrying LacZ, the medium was aspirated and cells were fixed with 1% formaldehyde, 0.2% glutaraldehyde in PBS for 10 minutes at room temperature. After washing the cells twice with PBS, the cells were incubated at 37° C. in a 2.5 mM X-gal (5-bromo-4-chloro-3-indolyl-β-galactosidase, Invitrogen, Grand Island, N.Y.) reaction mixture containing 5 mM $K_4Fe(CN)_6$, 5 mM $K_3Fe(CN)_6$ and 2 mM magnesium chloride in PBS. After 4 hours of incubation, plates were measured on an ELISA plate-reader (Bio-Tek Instruments Inc., Power Wave 340) at 495 nm. The 90% (or 50%) inhibition serum titer is corresponding to 10% of the maximum control value (no serum), interpolated in the serum dilution range.

Quantification of Adenoviral Genomes Per Cell by Q-PCR

Total DNA was isolated from infected A549 cells with the DNeasy tissue kit (Qiagen, Germany). The Q-PCR protocol is derived from Klein et al. (1999). CMV promoter was used as target sequence, which is present in all recombinant adenoviruses used in this study. The primers and probe used in this study were CMV-F353 (5'-CAT CTA CGT ATT AGT CAT CGC TAT TAC CA-3' SEQ ID NO:15), CMV-R446 (5'-TGG AAA TCC CCG TGA GTC A-3' SEQ ID NO:16) and probe CMV-2 (5'-VIC ACC GCT ATC CAC GCC CAT TGA TGT TAMRA-3' SEQ ID NO:17). A second pair of oligonucleotides and a probe recognizing 18S rDNA was added to the reaction to make determination of virus particles per cell possible (Klein et al. 2000). As standard for determination of the adenoviral genomes and number of cells present, the CMV promoter containing plasmid pAdApt35IP1 and human genomic DNA were used respectively. Amplification was performed in an ABI Prism 7700 sequence detection system (Perkin-Elmer).

Figure 32:
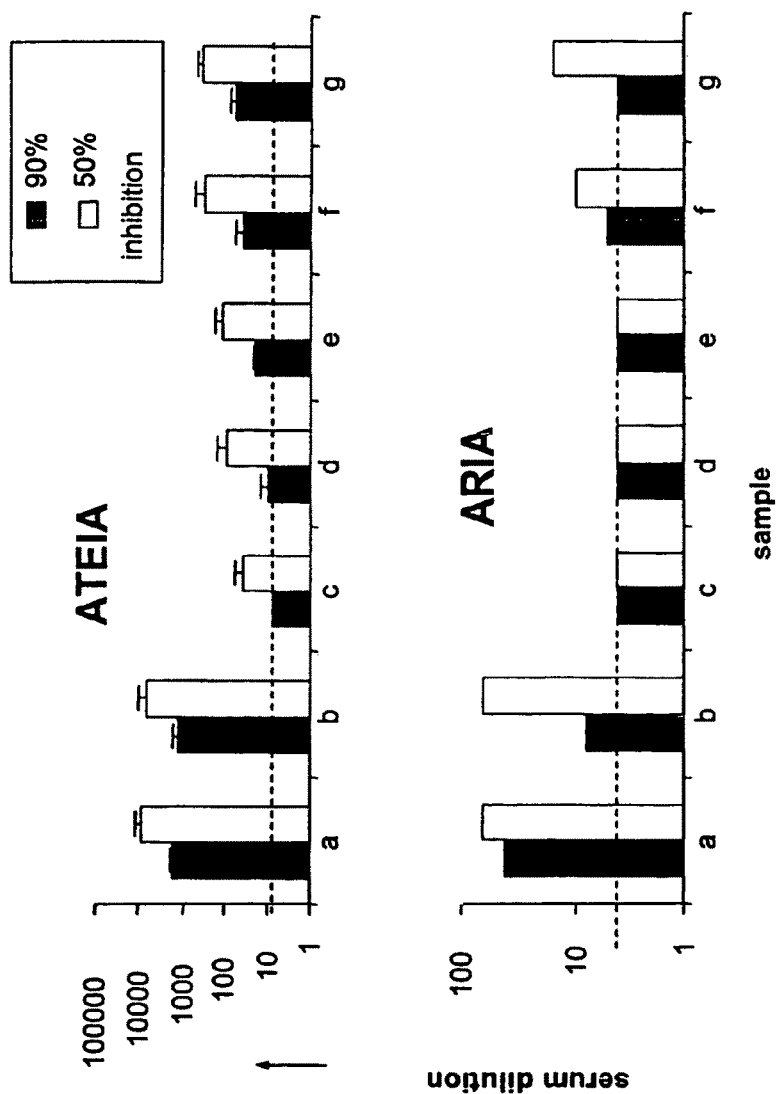
FIG. 32 is a comparison between an ARIA and an ATEIA assay.

To compare the ARIA and the ATEIA assays, a small panel of human serum samples was tested for anti-Ad5 antibody titers by ARIA, and in parallel with the ATEIA. The results, shown in FIG. 32, indicate that the ATEIA is more sensitive than the ARIA. Furthermore, neutralizing activity titers (50% and 90%) correlated better in the ATEIA than in the ARIA. Thus, based on sensitivity, a lower amount of serum required and significantly shorter time needed until read-out, the ATEIA is preferred.

Figure 33:
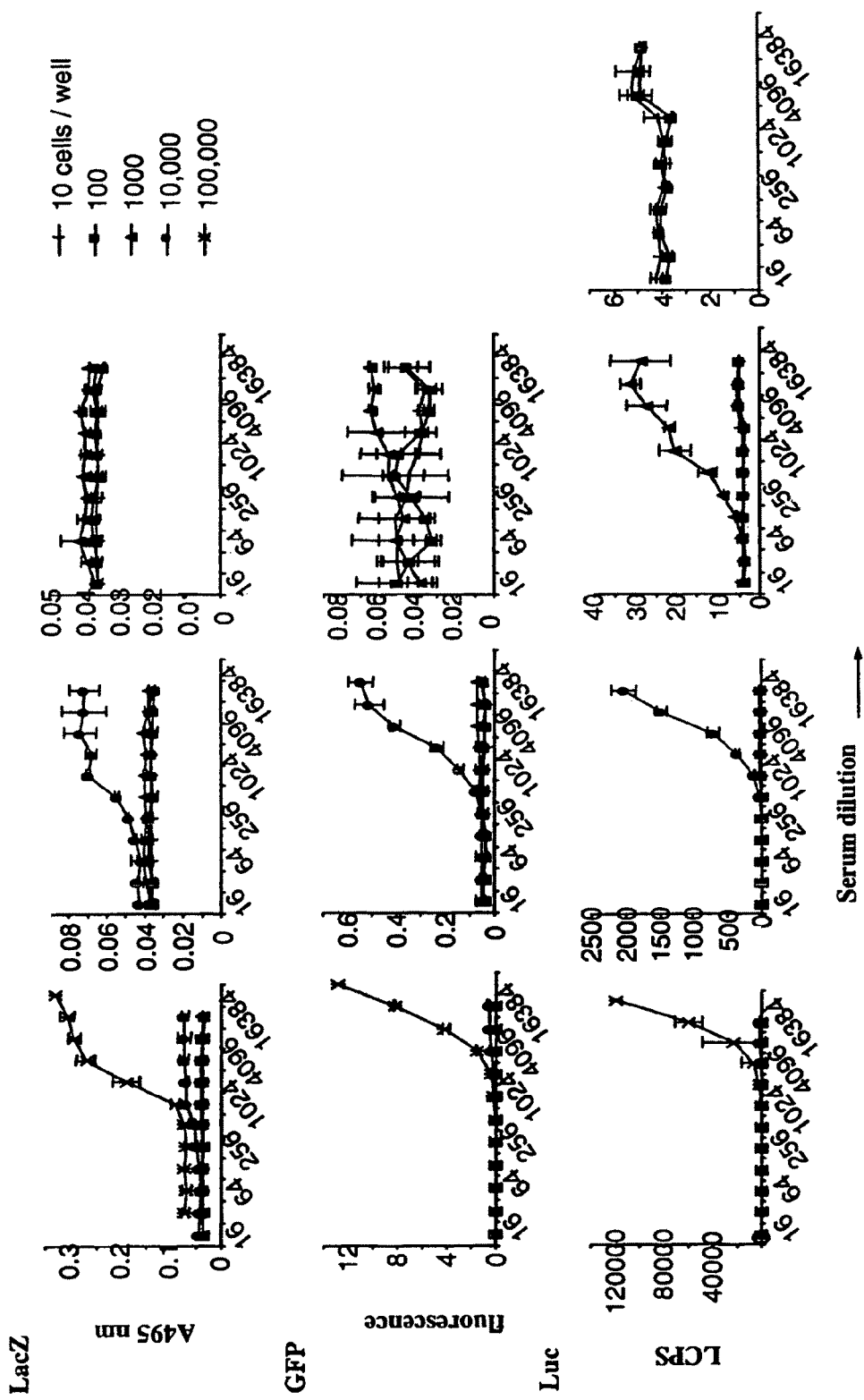
FIG. 33 shows different transgene activities using diluted numbers of cells per well in a titration assay.

One important parameter dictating the usefulness of this assay is the possibility to use small volumes of serum for high-through-put analyses. Hereto, the detection limit was determined by testing three different transgenes and their corresponding read-out system in combination with low cell numbers ($10^1$ to $10^5$ cells/well). For high-through-put purposes, cells infected with Ad5.LacZ were measured by optical density measurement, which proved successful in that obtained results are representative for the transduction inhibition as measured by counting infected cells using a microscope. From the results obtained (FIG. 33), it could be concluded that with LacZ and GFP, neutralizing antibodies can be detected only when $10^4$ cells/well were seeded, even when the new read-out method for Ad5.LacZ is used as described. In contrast, luciferase activity could still be detected when using $10^3$ cells/well. Moreover, these results showed that when more cells per well seeded, the assay becomes more sensitive.

The assay is intended to determine the inhibition of virus infection by measuring luciferase activity. To determine whether serum decreased actual virus entry into target cells, and to exclude that high serum concentrations killed target cells, thereby diminishing transgene expression, transgene detection (measurement of luciferase activity) was combined with cellular adenovirus genome detection (by Q-PCR). Simultaneous detection of the number of virus copies of Ad5 and Ad35 per cell and luciferase activity showed that transgene expression was correlated with Adenovirus genomes per cell, and that high serum concentrations both decreased luciferase and cellular adenovirus copies by its neutralizing activity (FIGS. 34B and 34C). Serum does not interfere with Q-PCR results, as the positive controls with Ad35 are positive throughout the serum dilution. These results show that neutralization takes place mainly extra-cellularly, not after virus entry in cellular vesicles, and that the assay specifically measures inhibition of virus infection, but not secondary effects of serum.

Figure 34A:
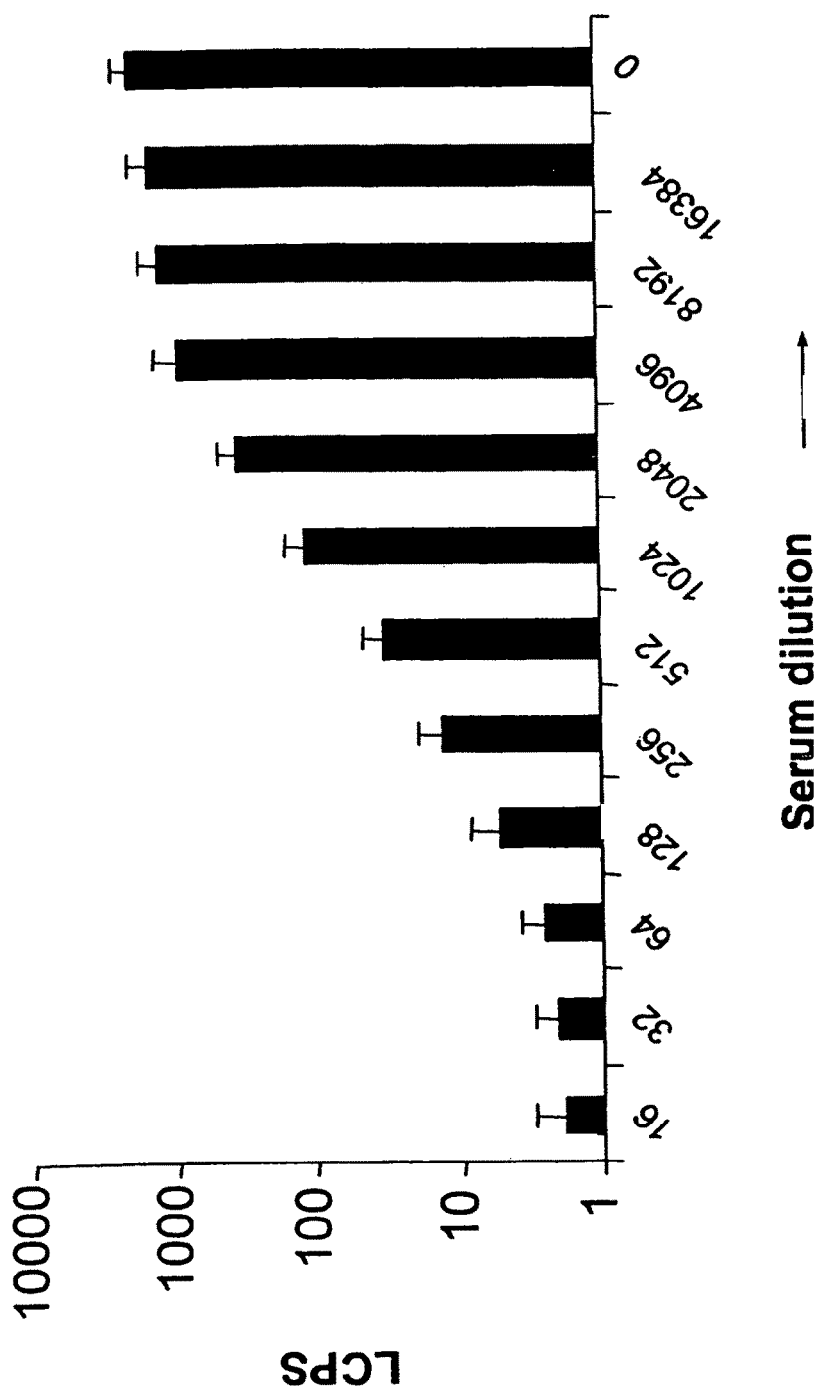
Figure 34D:
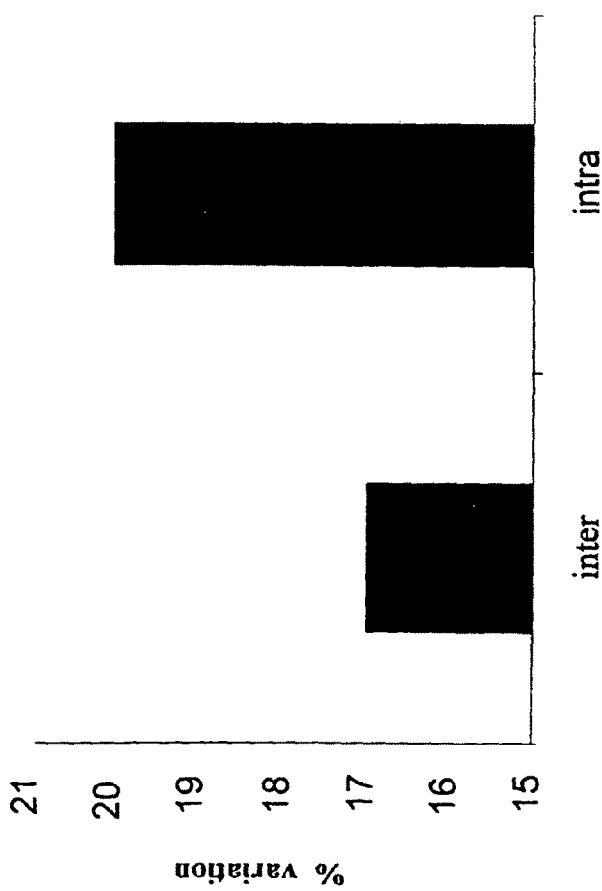

To validate the luciferase-based ATEIA, the assay was performed independently for five times in duplicate to assess precision and reproducibility (FIG. 34A). Given the low standard deviations it was concluded that the assay is well reproducible. Inter-assay variation was calculated by transforming the standard deviation of five repetitive measurements into percentages. In this experiment the serum dilution needed for 90% neutralization is 1260±220. In percentages this is a variation of 17% (FIG. 34D). Intra-assay variation, the standard deviation within one assay gave a serum dilution of 1390±274 for 90% neutralization. This is a variation of 20% (FIG. 34D). These data show that the assay is well reproducible with acceptable standard deviations.

Naturally, validation of an assay requires the presence of a standard positive control serum, one that is sufficiently characterized and readily available. One such standard could be the second "International Standard for anti-measles and anti-poliovirus human serum, types 1, 2, and 3," obtained from NIBSC (National Institute for Biological Standards and Control) provided that this serum neutralizes Ad5. For this purpose the standard serum was tested and it was found that indeed it contains neutralizing antibodies against recombinant Ad5. This positive control serum was titered with ATEIA on neutralizing activity for 1/2550 (50%) and 1/625 (90%) respectively.

To determine the robustness of the luciferase-based ATEIA, several factors were investigated that may influence the outcome of the assay. One factor may be the used cell line. The luciferase neutralization assay was performed standard on A549 cells as this cell line is highly susceptible to adenovirus infection of both Ad5 and Ad35. For several cell-lines including 3T3 (mouse fibroblasts), C2C12 (mouse myoblasts), human and murine dendritic cells, Ad5- and Ad35-neutralizing activity of Ad5-positive serum (either human or mouse) was tested. As all cells have a different infectious titer, this was established first for both viruses. This showed that the maximum luciferase activity varies among different cells, as it is receptor dependent. This somewhat influences the 90% and 50% neutralization values. However, each cell line showed that the Ad5-positive serum neutralized Ad5 and did not neutralize Ad35 (data not shown), indicating the relative flexibility of the assay in the use of cell lines.

Furthermore the effect of the sequence of events was tested, i.e., whether A549 cells should be attached to the wells bottom before exposure to serum and virus, or whether cells can be added after serum and virus are mixed. But no difference was observed (data not shown). Therefore the cells can be added after diluting serum and adding virus particles, which is easier and faster. Moreover, it was tested if there is an effect of the incubation time of serum and virus before cells are added. The incubation of serum and virus was varied from 0.5 to 60 minutes, but no differences in results were found.

Figure 35:
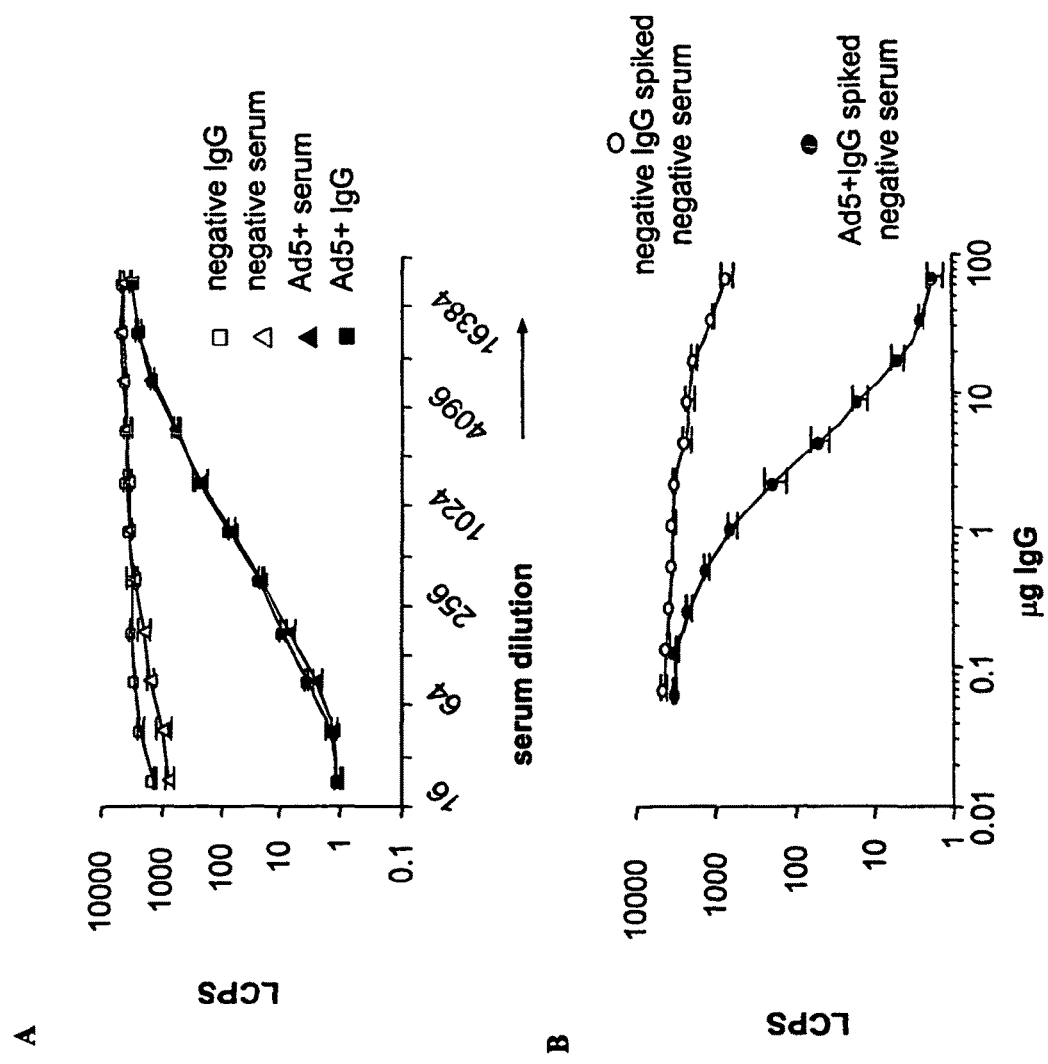
FIG. 35 shows the neutralization capacity of Ad5-positive and -negative serum +/−spiking of IgG isolated from Ad5-positive serum.

To demonstrate that the neutralizing effect of serum is mediated through antibodies, the assay was performed with isolated IgG. IgG isolation was confirmed by gel-electrophoresis and Coomassie blue staining (data not shown). FIG. 35, Panel A, shows the neutralization capacity of Ad5-positive and -negative serum from which the IgG was isolated and the neutralizing activity of the isolated IgG fractions. The Ad5-positive serum and its isolated IgG show neutralization, whereas the Ad5-negative serum and its isolated IgG do not show neutralization. In FIG. 35, Panel B, negative serum is spiked with IgG isolated from Ad5-positive serum and with IgG isolated from Ad5-negative serum. For 90% neutralization, 1.5 µg IgG is required. This demonstrates that neutralization activity can be transferred from a positive to a negative serum sample through IgG antibodies.

REFERENCES

D'Ambrosio E. et al. (1982) Neutralizing antibodies against 33 human adenoviruses in normal children in Rome. *J. Hyg.* (Lond) 89:155-161.

De Swart R. L. et al. (1998) Measles virus fusion protein- and hemagglutinin-transfected cell lines are a sensitive tool for the detection of specific antibodies by a FACS-measured immunofluorescence assay. *J. Virol. Meth.* 71:35-44.

Gaggar A. et al. (2003) CD46 is a cellular receptor for group B adenoviruses. *Nat. Med.* Oct. 19. (Epub ahead of print).

Hsu K.-H. L. et al. (1992) Immunogenicity of recombinant adenovirus-respiratory syncytial virus vaccines with adenovirus types 4, 5, and 7 vectors in dogs and a chimpanzee. *J. Infectious Diseases* 166:769-775.

Kass-Eisler A. et al. (1996) Circumventing the immune response to adenovirus-mediated gene therapy. *Gene Ther.* 3:154-162.

Klein D. et al. (2000) Accurate estimation of transduction efficiency necessitates a multiplex real-time PCR. *Gene Therapy* 7:458-463.

Lubeck M. D. et al. (1997) Long-term protection of chimpanzees against high-dose HIV-1 challenge induced by immunization. *Nature Med.* 3:651-658.

Mack C. A. et al. (1997) Circumvention of anti-adenovirus neutralizing immunity by administration of an adenoviral vector of an alternate serotype. *Hum. Gene Ther.* 8:99-109.

Mastrangeli A. et al. (1996) "Sero-switch" adenovirus-mediated in vivo gene transfer: circumvention of anti-adenovirus humoral immune defenses against repeat adenovirus vector administration by changing the adenovirus serotype. *Hum. Gene Ther.* 7:79-87.

Moffatt S. et al. (2000) Circumvention of vector-specific neutralizing antibody response by alternating use of human and non-human adenoviruses: Implications in gene therapy. *Virology* 272:159-167.

Parks R. J. et al. (1999) Use of helper-dependent adenoviral vectors of alternative serotypes permits repeat vector administration. *Gene Therapy* 6:1565-1573.

Pauwels R. et al. (1988) Rapid and automated tetrazolium-based colorimetric assay for the detection of anti-HIV compounds. *J. Virol. Methods* 20:309-321.

Roy S. et al. (1998) Circumvention of immunity to the adenovirus major coat protein hexon. *J. Virol.* 72:6875-6879.

Segerman A. et al. (2003) Adenovirus type 11 uses CD46 as a cellular receptor. *J. Virol.* 17:9183-9191.

Shayakhmetov D. M. et al. (2003) The interaction between the fiber knob domain and the cellular attachment receptor determines the intracellular trafficking route of adenoviruses. *J. Virol.* 77:3712-3723.

Shiver J. W. et al. (2002) Replication-incompetent adenoviral vaccine vector elicits effective anti-immunodeficiency-virus immunity. *Nature* 415:331-335.

Vogels R. et al. (2003) Replication-deficient human adenovirus type 35 vectors for gene transfer and vaccination: efficient human cell interaction and bypass of preexisting adenovirus immunity. *J. Virol.* 77:8263-8271.

What is claimed is:

1. A method for determining a titer of neutralizing antibodies directed against adenoviruses in a human- or animal-derived blood sample, the method comprising:
   obtaining a serum sample of the human or animal;
   culturing host cells which can be infected with a recombinant adenovirus;
   admixing the serum sample, the host cell culture and the recombinant adenovirus, wherein the recombinant adenovirus comprises a transgene encoding luciferase;
   incubating the admixture for about 24 hours;
   determining the activity of luciferase in the admixture; and
   comparing the activity of luciferase in the admixture to a serum-free control, thereby determining the titer of neutralizing antibodies in the blood sample;
   wherein the titer of neutralizing antibodies is determinable with 1000 host cells.

2. The method according to claim 1, wherein the determined activity of luciferase is compared to a standard value.

3. The method according to claim 1, wherein the host cells comprise A549 cells.

4. The method according to claim 1, wherein the serum sample is a diluted sample.

5. The method according to claim 1, wherein the serum sample is human serum or a dilution thereof.

6. The method of claim 1, the method further comprising determining the number of viral genomes per cell.

7. A high-throughput method for determining a titer of neutralizing antibodies directed against adenoviruses in a human- or animal-derived blood sample, the method comprising:
   obtaining a serum sample of said human or animal;
   culturing host cells which can be infected with a recombinant adenovirus;
   admixing the serum sample, the host cell culture and recombinant adenovirus, wherein the recombinant adenovirus comprises a transgene encoding luciferase;
   incubating the admixture for about 24 hours;
   determining the activity of luciferase in the admixture; and
   comparing the activity of luciferase in the admixture to a serum-free control, thereby determining the titer of neutralizing antibodies in the serum sample;
   wherein 1000 host cells are sufficient to determine the titer of neutralizing antibodies.

8. A method for determining the relative titers of neutralizing antibodies directed against adenoviruses of different serotypes in a human- or animal-derived blood sample, the method comprising:
   obtaining a serum sample of said human or animal;
   providing cultured host cells which can be infected by recombinant adenovirus of a first serotype and a second serotype;

admixing a first portion of the serum sample, a first portion of the cultured host cells and a recombinant adenovirus of the first serotype to form a first admixture, wherein the recombinant adenovirus of the first serotype comprises a transgene encoding luciferase;

admixing a second portion of the serum sample, a second portion of the cultured host cells and a recombinant adenovirus of the second serotype to form a second admixture, wherein the recombinant adenovirus of the second serotype comprises a transgene encoding luciferase;

incubating the admixtures for about 24 hours;

determining the activity of luciferase in both the first and second admixtures; and comparing the luciferase activities in the first and second admixtures to a serum-free control, thereby determining the relative titers of neutralizing antibodies to adenoviruses of the first and second serotypes in the serum sample;

wherein 1000 host cells will provide a titer of neutralizing antibodies.

* * * * *

SEQUENCE LISTING

<160> NUMBER OF SEQ ID NOS: 17

<210> SEQ ID NO 1
<211> LENGTH: 15
<212> TYPE: PRT
<213> ORGANISM: Simian immunodeficiency virus

<400> SEQUENCE: 1

Gln Thr Asp Ala Ala Val Lys Asn Trp Met Thr Gln Thr Leu Leu
1               5                   10                  15

<210> SEQ ID NO 2
<211> LENGTH: 7
<212> TYPE: PRT
<213> ORGANISM: Simian immunodeficiency virus

<400> SEQUENCE: 2

Ala Ala Val Lys Asn Trp Met
1               5

<210> SEQ ID NO 3
<211> LENGTH: 9
<212> TYPE: PRT
<213> ORGANISM: Simian immunodeficiency virus

<400> SEQUENCE: 3

Ala Ala Val Lys Asn Trp Met Thr Gln
1               5

<210> SEQ ID NO 4
<211> LENGTH: 11
<212> TYPE: PRT
<213> ORGANISM: Simian immunodeficiency virus

<400> SEQUENCE: 4

Ala Ala Val Lys Asn Trp Met Thr Gln Thr Leu
1               5                   10

<210> SEQ ID NO 5
<211> LENGTH: 15
<212> TYPE: PRT
<213> ORGANISM: Simian immunodeficiency virus

<400> SEQUENCE: 5

Glu Asn Leu Lys Ser Leu Tyr Asn Thr Val Cys Val Ile Trp Cys
1               5                   10                  15

<210> SEQ ID NO 6
<211> LENGTH: 9
<212> TYPE: PRT
<213> ORGANISM: Simian immunodeficiency virus

<400> SEQUENCE: 6

Lys Ser Leu Tyr Asn Thr Val Cys Val
1               5

<210> SEQ ID NO 7
<211> LENGTH: 10
<212> TYPE: PRT
<213> ORGANISM: Simian immunodeficiency virus

<400> SEQUENCE: 7

Lys Ser Leu Tyr Asn Thr Val Cys Val Ile
1               5                   10

```
<210> SEQ ID NO 8
<211> LENGTH: 8
<212> TYPE: PRT
<213> ORGANISM: Simian immunodeficiency virus

<400> SEQUENCE: 8

Leu Lys Ser Leu Tyr Asn Thr Val
1               5

<210> SEQ ID NO 9
<211> LENGTH: 10
<212> TYPE: PRT
<213> ORGANISM: Simian immunodeficiency virus

<400> SEQUENCE: 9

Leu Lys Ser Leu Tyr Asn Thr Val Cys Val
1               5                   10

<210> SEQ ID NO 10
<211> LENGTH: 32
<212> TYPE: DNA
<213> ORGANISM: Artificial
<220> FEATURE:
<223> OTHER INFORMATION: Synthetic oligonucleotide pIX11Fmfe

<400> SEQUENCE: 10
ctctctcaat tgtctgtctt gcagctgtca tg                                 32

<210> SEQ ID NO 11
<211> LENGTH: 22
<212> TYPE: DNA
<213> ORGANISM: Artificial
<220> FEATURE:
<223> OTHER INFORMATION: Synthetic oligonucleotide SV40for

<400> SEQUENCE: 11
caatgtatct tatcatgtct ag                                            22

<210> SEQ ID NO 12
<211> LENGTH: 35
<212> TYPE: DNA
<213> ORGANISM: Artificial
<220> FEATURE:
<223> OTHER INFORMATION: Synthetic oligonucleotide pIX5Rmfe

<400> SEQUENCE: 12
ctctctcaat tgcagataca aaactacata agacc                              35

<210> SEQ ID NO 13
<211> LENGTH: 32
<212> TYPE: DNA
<213> ORGANISM: Artificial
<220> FEATURE:
<223> OTHER INFORMATION: Synthetic oligonucleotide pIX35Fmfe

<400> SEQUENCE: 13
ctctctcaat tgtctgtctt gcagctgtca tg                                 32

<210> SEQ ID NO 14
<211> LENGTH: 40
<212> TYPE: DNA
<213> ORGANISM: Artificial
<220> FEATURE:
<223> OTHER INFORMATION: Synthetic oligonucleotide Ad11pIXcos(2)

<400> SEQUENCE: 14
```

```
ctgctggacg tcgcggccgc gtcatgagtg gaaacgcttc                            40

<210> SEQ ID NO 15
<211> LENGTH: 29
<212> TYPE: DNA
<213> ORGANISM: Artificial
<220> FEATURE:
<223> OTHER INFORMATION: Synthetic oligonucleotide CMV-F353

<400> SEQUENCE: 15
catctacgta ttagtcatcg ctattacca                                        29

<210> SEQ ID NO 16
<211> LENGTH: 19
<212> TYPE: DNA
<213> ORGANISM: Artificial
<220> FEATURE:
<223> OTHER INFORMATION: Synthetic oligonucleotide CMV-R446

<400> SEQUENCE: 16
tggaaatccc cgtgagtca                                                   19

<210> SEQ ID NO 17
<211> LENGTH: 24
<212> TYPE: DNA
<213> ORGANISM: Artificial
<220> FEATURE:
<223> OTHER INFORMATION: Synthetic oligonucleotide probe CMV-2
<220> FEATURE:
<221> NAME/KEY: misc_feature
<222> LOCATION: (1)..(1)
<223> OTHER INFORMATION: VIC label attached
<220> FEATURE:
<221> NAME/KEY: misc_feature
<222> LOCATION: (24)..(24)
<223> OTHER INFORMATION: TAMRA label attached

<400> SEQUENCE: 17
accgctatcc acgcccattg atgt                                             24
```